(12) United States Patent
Knick et al.

(10) Patent No.: US 7,939,074 B2
(45) Date of Patent: May 10, 2011

(54) COMBINATION OF AN ANTI-EP-CAM ANTIBODY WITH A CHEMOTHERAPEUTIC AGENT

(75) Inventors: Vincent C. Knick, Durham, NC (US); Julie Beth Stimmel, Durham, NC (US); Linda M. Thurmond, Durham, NC (US)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 12/684,558

(22) Filed: Jan. 8, 2010

(65) Prior Publication Data
US 2010/0172903 A1 Jul. 8, 2010

Related U.S. Application Data

(63) Continuation of application No. 11/034,655, filed on Jan. 13, 2005, now Pat. No. 7,648,703, which is a continuation of application No. 10/031,355, filed as application No. PCT/EP99/05271 on Jul. 23, 1999, now abandoned.

(51) Int. Cl.
*A61K 39/395* (2006.01)

(52) U.S. Cl. .............. 424/141.1; 424/155.1; 424/156.1

(58) Field of Classification Search .................... None
See application file for complete search history.

(56) References Cited

FOREIGN PATENT DOCUMENTS

| EP | 0252741 A | 1/1988 |
|---|---|---|
| WO | WO 87/00462 | 1/1987 |
| WO | WO 92/07075 | 4/1992 |
| WO | 99/31140 | 6/1999 |
| WO | WO 99/31140 | 6/1999 |

OTHER PUBLICATIONS

Bebbington et al., "High-level expression of a recombinant antibody from myeloma cells using a glutamine synthetase gene as an amplifiable selectable marker," *Bio/Technology* 10:169-175 (Feb. 1992).
Bhuyan et al., "Lethality, DNA alkylation, and cell cycle effects of adozelesin (U-73975) on rodent and human cells," *Cancer Research* 52(2):5687-5692 (Oct. 1992).
Bleiberg, "Continuing the fight against advanced colorectal cancer: new and future treatment options," *Anti-Cancer Drugs* 9:1 18-28 (Jan. 1998).
Bokemeyer et al., "Current aspects of adjuvant and palliative chemotherapy in colorectal carcinoma!. Aktuelle Aspekte zur adjuvanten and palliativen Chemotherapie beim kolorektalen Karzinom," *Schweizerische Rundschau Fur Medizin Praxis* 86:39 1510-1516 (Sep. 1997).
Casillas et al., "Adjuvant therapy for colorectal cancer: present and future perspectives," *Diseases of the Colon and Rectum* 40:8 977-992 (Aug. 1997).
Chen et al., "Differences in inhibition of chromosome separation and $G_2$ arrest by DNA topoisomerase II inhibitors merbarone and VM-26," *Cancer Research* 55(7):1509-1516 (Apr. 1995).
Colcher et al., "A spectrum of monoclonal antibodies reactive human mammary tumor cells," *Proc. Natl. Acad. Sci. USA* 78(5):3199-3203 (May 1981).
Czuczman et al., "IgM monoclonal antibody JD118 recognizes an inducible antigen target for human-complement-mediated cytotoxicity against neoplastic B cells," *Cancer Immunology, Immunotherapy* 36(6):387-396 (1993).
Elias et al., "Monoclonal antibody KS1/4-methotrexate immunoconjugate studies in non-small cell lung carcinoma," *American Journal of Respiratory and Critical Care Medicine* 15:4 1114-1122 (Oct. 1994).
Ellis et al., "Engineered anti-CD38 monoclonal antibodies for immunotherapy of multiple myeloma," *The Journal of Immunology* 155:925-937 (1995).
Engelholm et al., "Effect of Melphalan on growth curves and cell cycle distribution of four human small cell carcinomas of the lung grown in nude mice," *Experimental Cell Biology* 54(3):138-148 (1986).
Erba et al., "Comparison of cell-cycle phase perturbations induced by the DNA-minor-groove alkylator tallimustine and by melphalan in the SW626 cell line," *International Journal of Cancer* 62(2):170-175 (Jul. 1995).
Fargion et al., "Heterogeneity of cell surface antigen expression of human small cell lung cancer detected by monoclonal antibodies," *Cancer Research* 46:2633-2638 (May 1986).
Fogler et al., "Enhanced cytotoxicity against colon carcinoma by combinations of noncompeting monoclonal antibodies to the 17-1A antigen," *Cancer Research* 48:6303-6308 (1988).
Greiner et al., "Enhanced expression of surface tumor-associated antigens on human breast and colon tumor cells after recombinant human leukocyte α-interferon treatment," *Cancer Research* 44:3208-3214 (Aug. 1984).
Greiner et al., "Intraperitoneal administration of interferon-gamma to carcinoma patients enhances expression of tumor-associated glycoprotein-72 and carcinoembryonic antigen on malignant ascites cells," *J. Clin Oncol* 10(5):735-746 (May 1992).
Haisma et al., "A monoclonal antibody-beta-glucuronidase conjugate as activator of the prodrug epirubicin-glucuronide for specific treatment of cancer," *British Journal of Cancer* 66:3 474-478 (Sep. 1992).
Herlyn et al., "Colorectal carcinoma-specific antigen: detection by means of monoclonal antibodies," *Proc. Natl. Acad. Sci. USA* 76(3):1438-1452 (Mar. 1979).
Herlyn et al., "CO 17-1A and related monoclonal antibodies: their production and characterization," *Hybridoma* 5(Suppl. 1):S3-S10 (1986).
Inaba et al., "Flow cytometric analysis of cell-killing actions of 5-fluorouracil in human colorectal cancer cells," *Oncology Research* 6(7):303-309 (1994).
Jones et al., "Replacing the complementarity-determining regions in a human antibody with those from a mouse," *Nature* 321:522 (May 1986).
Kallio et al., "Effects of the DNA topoisomerase II inhibitor merbarone in male mouse meiotic divisions in vivo: Cell cycle arrest and induction of aneuploidy," *Environmental & Molecular Mutagenesis* 29(1):16-27 (1997).

(Continued)

*Primary Examiner* — Sheela J Huff
(74) *Attorney, Agent, or Firm* — William Peter Long; William T. Han

(57) ABSTRACT

A combination of an anti-Ep-CAM antibody with a chemotherapeutic agent that is capable of arresting Ep-CAM antigen expressing cells in S or $G_2/M$.

6 Claims, 22 Drawing Sheets

OTHER PUBLICATIONS

Figure 1:
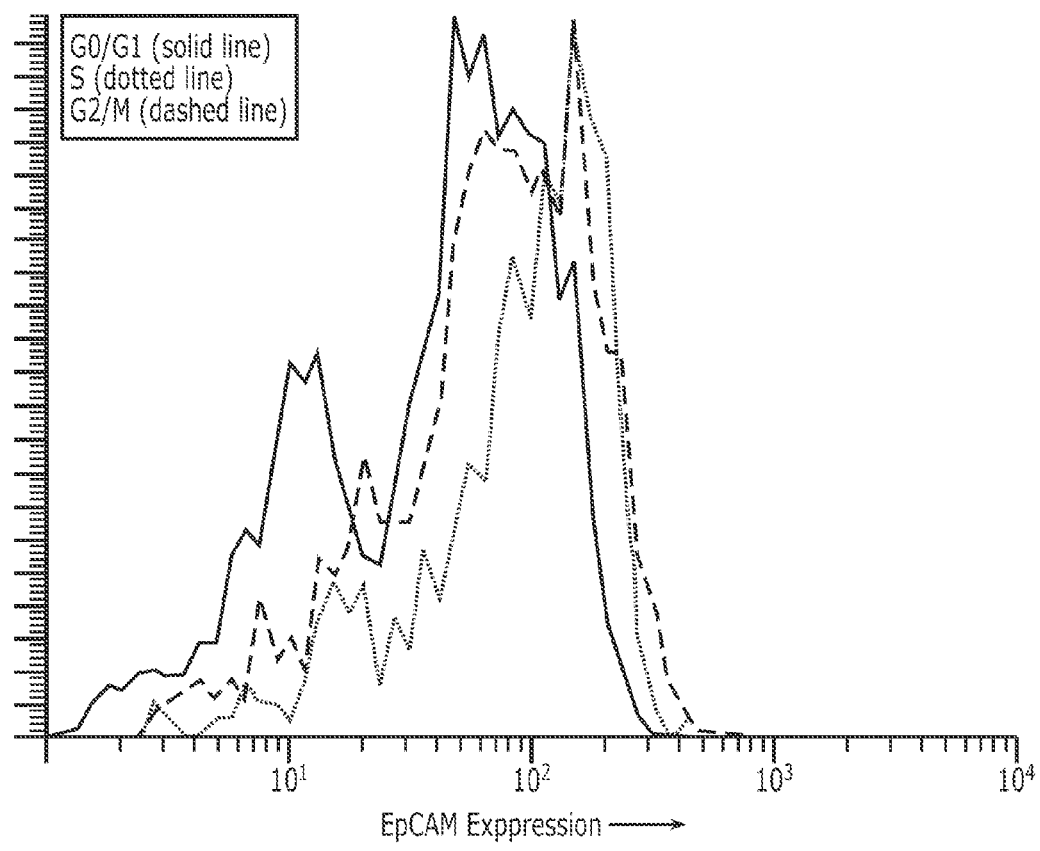

Kievit et al., "Determination of tumor-related factors of influence on the uptake of the monoclonal antibody 323/A3 in experimental human ovarian cancer," *International Journal of Cancer* 71:2 237-245 (Apr. 1997).

Klucar et al., "G2 cell cycle arrest and apoptosis are induced in Burkitt's lymphoma cells by the anticancer agent oracin," *FEBS Letters* 400(1):127-130 (Jan. 1997).

Laio et al., "Binding and functional properties of a mouse-human chimeric monoclonal antibody of the human IgG1 subclass with specificity for human carcinomas," *Human Antibody Hybridomas* 1(2):66-76 (1990).

Litvinow et al., "Ep-CAM: a human epithelial antigen is a homophilic cell-cell adhesion molecule," *J. Cell Biology* 125:437-446 (1994).

Okabe et al., "Monoclonal antibodies to surface antigens of small cell carcinoma of the lung," *Cancer Research* 44:5273-5278 (Nov. 1984).

Paul et al., "Treatment of advanced measurable or evaluable pancreatic carcinoma with 17-1A murine monoclonal antibody alone or in combination with 5-fluorouracil, adriamycin and mitomycin (FAM)," *Hybridoma* 5 Suppl:1 S171-S174 (Jul. 1986).

Reichmann et al., "Reshaping human antibodies for therapy," *Nature* 332:323-327 (Mar. 1988).

Riethmuller et al., "Monoclonal antibodies in the detection and therapy of micrometastatic epithelial cancers," *Curr. Opin. Immun.* 4:647-655 (1992).

Riethmuller et al., "Monoclonal antibodies in cancer therapy," *Curr. Opin. Immun.* 5:732-739 (1993).

Rojas et al., "Genotoxic effects of bistratene A on human lymphocytes," *Mutation Research* 367(3):169-175 (Mar. 1996).

Schwartzberg, "Chemotherapy plus PANOREX (17-1A monoclonal antibody) as adjuvant therapy for colon cancer: Ongoing studies," *Cancer Investigation* 17Suppl:1 32-34 (1999).

Song, "Expression of sarcoma-associated antigens p102 and p200 in human sarcoma cell lines," *Anticancer Research* 16(3A):1171-1175 (1996).

Stephens et al., "The construction of a highly efficient and versatile set of mammalian expression vectors," *Nucleic Acid Res.* 17(17):7110 (1989).

Tyle, "Iontophoretic devices for drug delivery," *Pharmaceutical Research* 3(6):318-326 (1986).

Verhoeyen et al., "Reshaping human antibodies: grafting an antilysozyme activity," *Science* 239:1534-1536 (Mar. 1988).

Watters et al., "Accumulation of HL-60 leukemia cells in G2/M and inhibition of cytokinesis caused by two marine compounds, bistratene A and cycloxazoline," *Cancer Chemotherapy & Pharmacology* 33(5):399-409 (1994).

Wei et al., "Expression of the surface antigen in human gastric cancer cells and the relation to cell cycles," *J of Oncology* 9(3):179-182 (1987) (Abstract).

Wulf et al., "A cell-surface apitope associated with liver-preferential metastasis detected by the new monoclonal antibody 3H4 in the murine tumor model ER 15-P," *J Cancer Research and Clinical Oncology* 122(8):476-482 (1996).

Ciardiello et al., Antitumor Activity of Sequential Treatment with Topotecan and Anti-epiderminal Growth Factor Receptor Monoclonal Antibody C225[1], Clinical Cancer Research 5:909-916 (Apr. 1999).

Goldenberg, Trastuzumab, a Recombinant DNA-Derived Humanized Monclonal Antibody, a Novel Agent for the Treatment of Metastatic Breast Cancer, Clinical Therapeutics 21(2):309-318 (1999).

Ishikawa et al., Antitumor Activities of a Novel Fluoropyrimidine, $N^4$-Pentyloxycarbonyl-5'-deoxy-5-fluorocytidine (Capecitabine), Biol. Pharm. Bull. 21(7):713-717 (1998).

Maloney et al., Monoclonal Antibody Therapy, Chapter 21, The Molecular Basis of Cancer, pp. 460-510 (1995).

Mendelsohn, Epidermal Growth Factor Receptor Inhibition by a Monoclonal Antibody as Anticancer Therapy, Clinical Cancer Research 3:2703-2707 (Dec. 1997).

Miwa et al., Design of a Novel Oral Fluoropyrimidine Carbamate, Capecitabine, which Generates 5-Fluorouracil Selectively in Tumours by Enzymes Concentrated in Human Liver and Cancer Tissue, Eur. J. of Cancer 34(8):1274-1281 (1998).

Murakami et al., Cell Cycle Regulation, Oncogenes, and Antineoplastic Drugs, Chapter 1, The Moelcular Basis of Cancer, pp. 3-17 (1995).

Pegram et al., Phase II Study of Receptor-Enhanced Chemosensitivity Using Recombinant Humanized Anti-p185$^{HER2/neu}$ Monoclonal Antibody Plus Cisplatin in Patients with HER2/neu-Overexpressing Metastatic Breast Cancer Refractory to Chemotherapy Treatment, J. Clin. Oncol 16:2659-2671 (1998).

Pegram et al., Inhibitory effects of combinations of Her-2/*neu* antibody and chemotherapeutic agents used for treatment of human breast cancers, Oncogene 18:2241-2251 (1999).

Pietras et al., Antibody to HER-2/*neu* receptor blocks DNA repair after cisplatin in human breast and ovarian cancer cells, Oncogene 9:1829-1838 (1994).

Punt, New Drugs in the Treatment of Colorectal Carcinoma, Cancer 83(4):679-689 (Aug. 15, 1998).

Cancer Principles & Practice Oncology, ed. DeVita, Jr. et al., Chapter 19 (Ratain) (1997).

Riethmüller, et al., Monoclonal Antibody Therapy for Resected Dukes C Colorectal Cancer: Seven-Year Outcome of a Multicenter Randomized Trial, J. Clin. Oncology 16:1788-1794 (1998).

Abstract #1385, Riethmüller, et al., Monoclonal Antibody (MAB) Adjuvant Therapy of Dukes C Colorectal Carcinoma 7-Year Update of a Prospective Randomized Trial, Proceedings of ASCO 15 (Mar. 1996).

Ross et al., The Her-2/*neu* Oncogene in Breast Cancer: Prognostic Factor, Predictive Factor, and Target for Therapy, Stem Cells 16:413-428 (1998).

Schneider-Gädicke and Riethmüller, Prevention of Manifest Metastasis with Monoclonal Antibodies: A Novel Approach to Immunotherapy of Solid Tumours, Eur. J. of Cancer 31A(7/8):1326-1330 (1995).

Scotto and Bertino, Chemotherapy Susceptibility and Resistance, The Molecular Basis of Cancer, eds. Mendelsohn, Howley, Israel, Liotto, 1995.

Tankanow, Docetaxel: A taxoid for the treatment of metastatic breast cancer, Am. J. Health-Syst Pharm. 55:1777-1791 (1998).

Molecular Biology of the Cell, $2^{nd}$ ed., eds Alberts et al., pp. 235-236 and 728 (1989).

Edwards, et al., "Monoclonal Antibody Identification and Characterization of a $M_r$ 43,000 Membrane Glycoprotein Associated with Human Breast Cancers[1]," *Cancer Research*, vol. 46, pp. 1306-1317, 1986.

Makower, et al., "A Pilot of Edrecolomab (Panorex, 17-1A Antibody) and Capecitabine in Patients with Advanced or Metastatic Adenocarcinoma," *Cancer Investigation*, vol. 21, No. 2, pp. 177-184, 2003.

Opposition Response from dfmp, dated Nov. 26, 2010, 20 pages.

Opposition Response from dfmp, Grounds of Appeal, dated Jul. 13, 2010, 25 pages.

Opposition Response from dfmp, dated Nov. 20, 2009, 11 pages.

Opposition Response from dfmp, $3^{rd}$ Party Observations, dated Feb. 4, 2009, 11 pages.

Opposition Response from Dehmel & Bettenhausen, dated Oct. 24, 2008, 17 pages.

Opposition Notice from Dehmel & Bettenhausen, dated Aug. 29, 2007, 22 pages.

GSK's Response to Opponent's Grounds of Appeal dated Jul. 13, 2010, dated Nov. 26, 2010, 8 pages.

GSK's Grounds of Appeal further to Notice of Appeal, dated Jul. 13, 2010, 13 pages.

GSK's Response to Summons dated Sep. 1, 2009, dated Nov. 20, 2009, 9 pages.

GSK's Response to Communication dated Oct. 12, 2007, dated Apr. 11, 2008, 20 pages.

Litvinow, et al., "Ep-CAM: A Human Epithelial Antigen is a Homophilic Cell-Cell Adhesion Molecule," *The Journal of Cell Biology*, vol. 125, No. 2, pp. 437-446, 1994 (D1).

Kievit, et al., "Addition of Cisplatin Improves Efficacy of $^{131}$I-Labeled Monoclonal Antibody 323/A3 in Experimental Human Ovarian Cancer," *Int. J. Radiation Oncology Biol. Phys.*, vol. 38, No. 2, pp. 419-428, 1997 (D2).

Schneider-Gädicke, et al., "Prevention of Manifest Metastasis with Monoclonal Antibodies: A Novel Approach to Immunotherapy of Solid Tumours," *European Journal of Cancer*, vol. 31A, Nos. 7/8, pp. 1326-1330, 1995 (D3).

Riethmüller, et al., "Monoclonal Antibody Therapy for Resected Dukes' C Colorectal Cancer: Seven-Year Outcome of a Multicenter Randomized Trial," *Journal of Clinical Oncology*, vol. 16, No. 5, pp. 1788-1794, 1998 (D4).

Paul, et al., "Treatment of Advanced Measurable or Evaluable Pancreatic Carcinoma with 17-1A Murine Monoclonal Antibody Alone or in Combination with 5-Fluorouracil, Adriamycin and Mitomycin (FAM)," *Hybridoma*, vol. 5, Suppl. 1, pp. S171-S174, 1986 (D5).

Lee S. Schwartzberg, "Chemotherapy Plus PANOREX (17-1A Monoclonal Antibody) as Adjuvant Therapy for Colon Cancer: Ongoing studies," *Cancer Investigation*, vol. 17, Suppl. 1, pp. 32-34, 1999. Meeting Info.: XVI Chemotherapy Foundation Symposium on Innovative Cancer Therapy for Tomorrow, New York City, New York, USA Nov. 11-13, 1998 Chemotherapy Foundation, XP000882015 (D6).

Riethmüller, et al., "Monoclonal Antibody (MAB) Adjuvant Therapy of Dukes C Colorectal Carcinoma: 7-Year Update of a Prospective Randomized Trial," *Proceedings of Asco*, vol. 15, p. 444, 1996 (D7), Abstract # 1385.

Inaba, et al., "Flow Cytometric Analysis of Cell-killing Actions of 5-Fluorouracil in Human Colorectal Cancer Cells," *Oncology Research*, vol. 6, No. 7, pp. 303-309, 1994 (D8).

Oxford Dictionary of Biochemistry and Molecular Biology, Oxford University Press, pp. 19, 118, 185, 188, 219, 240, 422, 481 and 635, 1997 (D10).

Molecular Biology of the Cell, 2nd edition, Garland Publishing, Inc., pp. 235, 236 and 728, 1989 (D11).

Römpp Chemie Lexikon, pp. 567, 839, 2737 and 2811, 1995 (D12).

Ernst Mutschler, Arzneimittel-wirkungen, Lehrbuch der Pharmakologie und Toxikologie, pp. 658 and 659, 1986 (D13).

Miwa, et al., "Design of a Novel Oral Fluoropyrimidine Carbarnate, Capecitabine, which Generates 5-Fluorouracil Selectively in Tumours by Enzymes Concentrated in Human Liver and Cancer Tissue," *European Journal of Cancer*, vol. 34, No. 8, pp. 1274-1281, 1998 (D14).

Ishikawa, et al., "Antitumor Activities of a Novel Fluoropyrimidine, $N^4$-Pentyloxycarbonyl-5'-deoxy-5-fluorocytidine (Capecitabine)," *Biol. Pharm. Bull.*, vol. 21, No. 7, pp. 713-717, 1998 (D15).

Cornelis J.A. Punt, "New Drugs in the Treatment of Colorectal Carcinoma", *Cancer*, vol. 83 No. 4, pp. 679-689, 1998 (D16).

Roberta M. Tankanow, "Docetaxel: A taxoid for the treatment of metastatic breast cancer," *Am. J. Health-Syst. Pharm*, vol. 55, pp. 1777-1791, 1998 (D18).

Mendelsohn, et al., "The Molecular Basis of Cancer," W.B. Saunders Co., pp. 3-17, 387-400, 460-479, 492,493, 499-510, 1995 (D19).

DeVita, et al., "Cancer—Principles & Practice of Oncology," Lippincott-Raven Publishers, pp. 375-498, 1997 (D20), (Chapter 19).

Ross, et al., "The HER-2/*neu* Oncogene in Breast Cancer: Prognostic Factor, Predictive Factor, and Target for Therapy," *Stem Cells*, vol. 16, pp. 413-428, 1998 (D21).

John Mendelsohn, "Epidermal Growth Factor Receptor Inhibition by a Monoclonal Antibody as Anticancer Therapy[1]," *Clinical Cancer Research*, vol. 3, pp. 2703-2707, 1997 (D22).

Martin M. Goldenberg, "Trastuzumab, a Recombinant DNA-Derived Humanized Monoclonal Antibody, a Novel Agent for the Treatment of Metastatic Breast Cancer," *Clinical Therapeutics*, vol. 21, No. 2, pp. 309-318, 1999 (D23).

Pietras, et al., "Antibody to HER-2/*neu* receptor blocks DNA repair after cisplatin in human breast and ovarian cancer cells," *Oncogene*, vol. 9, pp. 1829-1838, 1994 (D24).

Pegram, et al., "Inhibitory effects of combinations of HER-2/*neu* antibody and chemotherapeutic agents used for treatment of human breast cancers," *Oncogene*, vol. 18, pp. 2241-2251, 1999 (D25).

Pegram, et al., "Phase II Study of Receptor-Enhanced Chemosensitivity Using Recombinant Humanized Anti-p185$^{HER2/}$ *neu* Monoclonal Antibody Plus Cisplatin in Patients with HER2/*neu*-Overexpressing Metastatic Breast Cancer Refractory to Chemotherapy Treatment," *Journal of Clinical Oncology*, vol. 16, No. 8, pp. 2659-2671, 1998 (D26).

Ciardiello, et al., "Antitumor Activity of Sequential Treatment with Topotecan and Anti-Epidermal Growth Factor Receptor Monoclonal Antibody C225[1]," *Clinical Cancer Research*, vol. 5, pp. 909-916, 1999 (D27).

Flinn, et al., "Monoclonal antibodies and autologous stem cell transplantation for Lymphoma," *Bone Marrow Transplantation*, vol. 27, pp. 565-569, 2001 (D29).

Kipps, et al., "Importance of Immunoglobulin Isotype in Human Antibody-Dependent, Cell-Mediated Cytotoxicity Directed by Murine Monoclonal Antibodies," *J. Exp. Med.*, vol. 161, pp. 1-17, 1985 (D30).

Roitt, et al.,"Immunology 3rd edition", Mosby, 11 pages, 1993 (D31).

Janeway and Travers, "Immunologie", Spektrum, 10 pages, 1995 (D32). (Explanation of relevance provided in "Opposition" and "GSK" documents provided herewith).

Janeway and Travis, "Immunologie", 2. Auflage, Spektrum, 4 pages, 1997 (D33). (Explanation of relevance provided in "Opposition" and "GSK" documents provided herewith).

Kievit, et al, "Determination of Tumor-Related Factors of Influence on the Uptake of the Monoclonal Antibody 323/A3 in Experimental Human Overian Cancer," *Int. J. Cancer*, vol. 71, pp. 237-245, 1997 (D36).

Thurmond, et al., "Adenocarcinoma cells exposed in vitro to Navelbine or Taxol increase Ep-CAM expression through a novel mechanism," *Cancer Immunol. Immunother.*, vol. 52, pp. 429-437, 2003 (D37).

Packeisen, et al., "Detection of Surface Antigen 17-1A in Breast and Colorectal Cancer," *Hybridoma*, vol. 18, No. 1, pp. 37-40, 1999 (D38).

Edith A. Perez, "Paclitaxel in Breast Cancer," *The Oncologist*, vol. 3, pp. 373-389, 1998 (D39).

Giordano, et al., "Impact of a Scientific Presentation on Community Treatment Patterns for Primary Breast Cancer", *Journal of the National Cancer Institute*, vol. 98, No. 6, pp. 382-388, 2006 (D42).

Henderson, et al., "Improved Disease-Free (DFS) and Overall Survival (OS) from the Addition of Sequential Paclitaxel (T) but not from the Escalation of Doxorubicin (A) Dose Level in the Adjuvant Chemotherapy of Patients (PTS) with Node-Positive Primary Breast Cancer (BC) (Meeting Abstract)," *Proc. ASCO*, Abstract No. 390, 2 pages, 1998 (D43).

Abdullah, et al., "The role of monocytes and natural killer cells in mediating antibody-dependent lysis of colorectal tumour cells," *Cancer Immunol. Immunother.*, vol. 48, pp. 517-524, 1999 (D44).

Sheppard et al., "Effects of Paclitaxel on the Growth of Normal, Polyposis, and Cancerous Human Colonic Epithelial Cells," *Cancer*, vol. 85, No. 7, pp. 1454-1464, 1999 (D45).

Humanised 323/A3 (IgG$_1$) Kappa Light Chain Amino Acid Sequence SEQ ID NO: 11
The amino acid sequence of the humanized light chain of
323/A3 IgG$_1$, including leader peptide, is shown below.

```
  1    MGWSCIILFL  VATATGVHSD  IVMTQSPLSL  PVTPGEPASI
 41    SCRSSJBKKG  SNGITYLYWY  LQKPGQSPQL  LIYQMSNLAS
 81    GVPDRFSSSG  SGTDFTLKIS  RVEAEDVGVY  YCAQNLEIPR
121    TFGQGTKVEI  KRTVAAPSVF  IFPPSDEQLK  SGTASVVCLL
161    NNFYPREAKV  QWKVDNALQS  GNSQESVTEQ  DSKDSTYSLS
201    STLTLSKADY  EKHKVYACEV  THQGLSSPVT  KSFNRGEC
```

FIG. 6

Humanised 323/A3 (IgG$_1$) Heavy Chain Amino Acid Sequence
The final amino acid sequence of the humanized heavy chain
323/A3 IgG$_1$, including leader peptide, is shown below. SEQ ID NO: 12

```
  1    MGWSCIILFL  VATATGVHSQ  VQLVQSGPEV  KKPGASVKVS
 41    CKASGYTFTN  YGMNWVRQAP  GQGLEWMGWI  NTYTGEPTYG
 81    EDFKGRFAFS  LDTSASTAYM  ELSSLRSEDT  AVYFCARFGN
121    YVDYWGQGSL  VTVSSASTKG  PSVFPLASS   KSTSGGTAAL
161    GCLVKDYFPE  PVTVSWNSGA  LTSGVHTFPA  VLQSSGLYSL
201    SSVVTVPSSS  LGTQTYICNV  NHKPSNTKVD  KKVEPKSCDK
241    THTCPPCPAP  ELLGGPSVFL  FPPKPKDTLM  ISRTPEVTCV
281    VVDVSHEDPE  VKFNWYVDGV  EVHNAKTKPR  EEQYNSTYRV
321    VSVLTVLHQD  WLNGKEYKCK  VSNKALPAPI  EKTISKAKGQ
361    PREPQVYTLP  PSRDELTKNQ  VSLTCLVKGF  YPSDIAVEWE
401    SNGQPENNYK  TTPPVLDSDG  SFFLYSKLTV  DKSRWQQGNV
441    FSCSVMHEAL  HNHYTQKSLS  LSPGK
```

FIG. 7

Humanised 323/A3 (IgG$_{4cys}$) Kappa Light Chain Amino Acid Sequence SEQ ID NO: 13
The final amino acid sequence of the humanized light chain of
323/A3 IgG$_4$, including leader peptide, is shown below.

```
  1   MGWSCIILFL   VATATGVHSD   IVMTQSPLSL   PVTPGEPASI
 41   SCRSSKNLLH   SNGITYLYWY   LQKPGQSPQL   LIYQMSNLAS
 81   GVPDRFSSSG   SGTDFTLKIS   RVEAEDVGVY   YCAQNLEIPR
121   TFGQGTKVEI   KRTVAAPSVF   IFPPSDEQLK   SGTASVVCLL
161   NNFYPREAKV   QWKVDNALQS   GNSQESVTEQ   DSKDSTYSLS
201   STLTLSKADY   EKHKVYACEV   THQGLSSPVT   KSFNRGEC
```

FIG. 11

Humanised 323/A3 (IgG$_{4cys}$) Heavy Chain Amino Acid Sequence SEQ ID NO: 14
The final amino acid sequence of the humanized heavy chain
323/A3 IgG$_4$, including leader peptide, is shown below.

```
  1   MGWSCIILFL   VATATGVHSQ   VQLVQSGPEV   KKPGASVKVS
 41   CKASGYTFTN   YGMNWVRQAP   GQGLEWMGWI   NTYTGEPTYG
 81   EDFKGRFAFS   LDTSASTAYM   ELSSLRSEDT   AVYFCARFGN
121   YVDYWGQGSL   VTVSSASTKG   PSVFPLAPCS   RSTSESTAAL
161   GCLVKDYFPE   PVTVSWNSGA   LTSGVHTFPA   VLQSSGLYSL
201   SSVVTVPSSS   LGTKTYTCNV   DHKPSNTKVD   KRVESKYGPP
241   CPPCPAPEFA   GAPSVFLFPP   KPKDTLMISR   TPEVTCVVVD
281   VSQEDPEVQF   NWYVDGVEVH   NAKTKPREEQ   FNSTYRVVSV
321   LTVLHQDWLN   GKAYKCKVSN   KGLPSSIEKT   ISKAKGQPRE
361   PQVYTLPPSQ   EEMTKNQVSL   TCLVKGFYPS   DIAVEWESNG
401   QPENNYKTTP   PVLDSDGSFF   LYSRLTVDKS   RWQEGNVFSC
441   SVMHEALHNH   YTQKSLCLSL   GK
```

FIG. 12

Humanised 323/A3 (IgG$_{2cys}$) Kappa Light Chain Amino Acid Sequence SEQ ID NO: 15
The final amino acid sequence of the humanized light chain of
323/A3 IgG$_{2cys}$, including leader peptide, is shown below.

```
  1    MGWSCIILFL   VATATGVHSD   IVMTQSPLSL   PVTPGEPASI
 41    SCRSSKNLLH   SNGITYLYWY   LQKPGQSPQL   LIYQMSNLAS
 81    GVPDRFSSSG   SGTDFTLKIS   RVEAEDVGVY   YCAQNLEIPR
121    TFGQGTKVEI   KRTVAAPSVF   IFPPSDEQLK   SGTASVVCLL
161    NNFYPREAKV   QWKVDNALQS   GNSQESVTEQ   DSKDSTYSLS
201    STLTLSKADY   EKHKVYACEV   THQGLSSPVT   KSFNRGEC
```

FIG. 13

Humanised 323/A3 (IgG$_{2cys}$) Heavy Chain Amino Acid Sequence SEQ ID NO: 16
The final amino acid sequence of the humanized heavy chain of
323/A3 Ig2$_{cys4}$, including leader peptide, is shown below.

```
  1    MGWSCIILFL   VATATGVHSQ   VQLVQSGPEV   KKPGASVKVS
 41    CKASGYTFTN   YGMNWVRQAP   GQGLEWMGWI   NTYTGEPTYG
 81    EDFKGRFAFS   LDTSASTAYM   ELSSLRSEDT   AVYFCARFGN
121    YVDYWGQGSL   VTVSSASTKG   PSVFPLAPCS   RSTSESTAAL
161    GCLVKDYFPE   PVTVSWNSGA   LTSGVHTFPA   VLQSSGLYSL
201    SSVVTVPSSN   FGTQTYTCNV   DHKPSNTKVD   KTVERKCCVE
241    CPPCPAPPVA   GPSVFLFPPK   PKDTLMISRT   PEVTCVVVDV
281    SHEDPEVQFN   WYVDGVEVHN   AKTKPREEQF   NSTFRVVSVL
321    TVVHQDWLNG   KEYKCKVSNK   GLPAPAIEKTI   SKTKGQPREP
361    QVYTLPPSRE   EMTKNQVSLT   CLVKGFYPSD   IAVEWESNGQ
401    PENNYKTTPP   MLDSDGSFFL   YSKLTVDKSR   WQQGNVFSCS
441    VMHEALHNHY   TQKSLCLSLG   K
```

FIG. 14

Humanised 323/A3 (IgG₁) Light Chain DNA Sequence
also 323/A3 (IgG4cys and IgG2cys light chain cDNA sequence) SEQ ID NOs: 1, 2 and 3

```
          10          20               30          40          50
  CGTAAGCTTC  ACAGGACCTC      ACC ATG GGA TGG AGC TGT ATC ATC CTC TTC TTG
  GCATTCGAAG  TGTCCTGGAG      TGG TAC CCT ACC TCG ACA TAG TAG GAG AAG AAC
                              Met Gly Trp Ser Cys Ile Ile Leu Phe Leu>

60          70          80          90          100
  GTA GCA ACA GCT ACA GGT GTC CAC TCC GAT ATT GTG ATG ACT CAG TCT
  CAT CGT TGT CGA TGT CCA CAG GTG AGG CTA TAA CAC TAC TGA GTC AGA
  Val Ala Thr Ala Thr Gly Val His Ser>
                                      Asp Ile Val Met Thr Gln Ser>

110         120         130         140
  CCA CTC TCC CTG CCC GTC ACC CCT GGA GAG CCG GCC TCC ATC TCC TGT
  GGT GAG AGG GAC GGG CAG TGG GGA CCT CTC GGC CGG AGG TAG AGG ACA
  Pro Leu Ser Leu Pro Val Thr Pro Gly Glu Pro Ala Ser Ile Ser Cys>

150         160         170         180         190
  AGG TCT AGT AAG AAT CTC CTG CAT AGT AAT GGC ATC ACT TAT TTG TAT
  TCC AGA TCA TTC TTA GAG GAC GTA TCA TTA CCG TAG TGA ATA AAC ATA
  Arg Ser Ser Lys Asn Leu Leu His Ser Asn Gly Ile Thr Tyr Leu Tyr>

200         210         220         230         240
  TGG TAC CTG CAG AAG CCA GGG CAG TCT CCA CAG CTC CTG ATC TAT CAG
  ACC ATG GAC GTC TTC GGT CCC GTC AGA GGT GTC GAG GAC TAG ATA GTC
  Trp Tyr Leu Gln Lys Pro Gly Gln Ser Pro Gln Leu Leu Ile Tyr Gln>

250         260         270         280         290
  ATG TCC AAC CTT GCC TCA GGG GTC CCT GAC AGG TTC AGT AGC AGT GGA
  TAC AGG TTG GAA CGG AGT CCC CAG GGA CTG TCC AAG TCA TCG TCA CCT
  Met Ser Asn Leu Ala Ser Gly Val Pro Asp Arg Phe Ser Ser Ser Gly>

300         310         320         330         340
  TCA GGC ACA GAT TTT ACA CTG AAA ATC AGC AGA GTG GAG GCT GAG GAT
  AGT CCG TGT CTA AAA TGT GAC TTT TAG TCG TCT CAC CTC CGA CTC CTA
  Ser Gly Thr Asp Phe Thr Leu Lys Ile Ser Arg Val Glu Ala Glu Asp>

350         360         370         380
  GTT GGG GTT TAT TAC TGT GCT CAA AAT CTA GAG ATT CCT CGG ACG TTC
  CAA CCC CAA ATA ATG ACA CGA GTT TTA GAT CTC TAA GGA GCC TGC AAG
  Val Gly Val Tyr Tyr Cys Ala Gln Asn Leu Glu Ile Pro Arg Thr Phe>
``` to FIG. 15A

FIG. 15

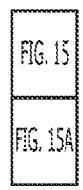

from FIG. 15

```
390            400            410            420            430
GGC CAA GGG ACC AAG GTG GAG ATC AAA CGT ACG GTG GCT GCA CCA TCT
CCG GTT CCC TGG TTC CAC CTC TAG TTT GCA TGC CAC CGA CGT GGT AGA
Gly Gla Gly Thr Lys Val Glu Ile Lys Arg>
                                        Thr Val Ala Ala Pro Ser>

440            450            460            470            480
GTC TTC ATC TTC CCG CCA TCT GAT GAG CAG TTG AAA TCT GGA ACT GCC
CAG AAG TAG AAG GGC GGT AGA CTA CTC GTC AAC TTT AGA CCT TGA CGG
Val Phe Ile Phe Pro Pro Ser Asp Glu Gln Leu Lys Ser Gly Thr Ala>

490            500            510            520            530
TCT GTT GTG TGC CTC CTG AAT AAC TTC TAT CCC AGA GAG GCC AAA GTA
AFA CAA CAC ACG GAC GAC TTA TTG AAG ATA GGG TCT CTC CGG TTT CAT
Ser Val Val Cys Leu Leu Asn Asn Phe Tyr Pro Arg Glu Ala Lys Val>

540            550            560            570            580
CAG TGG AAG GTG GAT AAC GCC CTC CAA TCG GGT AAC TCC CAG GAG AGT
GTC ACC TTC CAC CTA TTG CGG GAG GTT AGC CCA TTG AGG GTC CTC TCA
Gln Trp Lys Val Asp Asn Ala Leu Gln Ser Gly Asn Ser Gln Glu Ser>

590            600            610            620
GTC ACA GAG CAG GAC AGC AAG GAC AGC ACC TAC AGC CTC AGC AGC ACC
CAG TGT CTC GTC CTG TCG TTC CTG TCG TGG ATG TCG GAG TCG TCG TGG
Val Thr Glu Gln Asp Ser Lys Asp Ser Thr Tyr Ser Leu Ser Ser Thr>

630            640            650            660            670
CTG ACG CTG AGC AAA GCA GAC TAC GAG AAA CAC AAA GTC TAC GCC TGC
GAC TGC GAC TCG TTT CGT CTG ATG CTC TTT GTG TTT CAG ATG CGG ACG
Leu Thr Leu Ser Lys Ala Asp Tyr Glu Lys His Lys Val Tyr Ala Cys>

680            690            700            710            720
GAA GTC ACC CAT CAG GGC CTG AGC TCG CCC GTC ACA AAG AGC TTC AAC
CTT CAG TGG GTA GTC CCG GAC TCG AGC GGG CAG TGT TTC TCG AAG TTG
Glu Val Thr His Gln Gly Leu Ser Ser Pro Val Thr Lys Ser Phe Asn>

730            740
AGG GGA GAG TGT TAG
TCC CCT CTC ACA ATC
Arg Gly Gln Cys Ala>
```

FIG. 15A

Humanised 323/A3 (IgG$_1$) Heavy Chain DNA Sequence
SEQ ID NOs: 4 and 5

```
            10          20                  30           40              50
   CGTAAGCTTC  ACAGATCCTC    ACC ATG GGA TGG AGC TGT ATC ATC CTC TTT CTG
                                 Met Gly Trp Ser Cys Ile Ile Leu Phe Leu>

60          70          80           90              100
   GTG GCA ACA GCT ACA GGT GTC CAC TCC CAG GTA CAG CTA GTG CAA TCA
   Val Ala Thr Ala Thr Gly Val His Ser>
                                     Gln Val Gln Leu Val Gln Ser>

110         120         130         140
   GGG CCT GAA GTG AAG AAG CCT GGG GCC TCA GTG AAA GTT TCC TGC AAG
   Gly Pro Glu Val Lys Lys Pro Gly Ala Ser Val Lys Val Ser Cys Lys>

150         160         170         180             190
   GCT TCT GGC TAC ACC TTC ACC AAC TAT GGA ATG AAC TGG GTA AGG CAG
   Ala Ser Gly Tyr Thr Phe Thr Asn Tyr Gly Met Asn Trp Val Arg Gln>

200         210         220         230             240
   GCG CCT GGA CAG GGG CTT GAG TGG ATG GGG TGG ATA AAC ACC TAC ACT
   Ala Pro Gly Gln Gly Leu Glu Trp Met Gly Trp Ile Asn Thr Tyr Thr>

250         260         270         280             290
   GGA GAG CCA ACA TAT GGT GAA GAT TTC AAG GGA CGG TTT GCA TTC TCT
   Gly Glu Pro Thr Tyr Gly Glu Asp Phe Lys Gly Arg Phe Ala Phe Ser>

300         310         320         330             340
   CTA GAC ACA TCC GCC AGC ACA GCC TAT ATG GAG CTC AGC TCG CTG AGA
   Leu Asp Thr Ser Ala Ser Thr Ala Tyr Met Glu Leu Ser Ser Leu Arg>

350         360         370         380
   TCC GAG GAC ACT GCA GTC TAT TTC TGT GCG AGA TTT GGT AAC TAC GTA
   Ser Glu Asp Thr Ala Val Tyr Phe Cys Sla Arg Phe Gly Asn Tyr Val>

390         400         410         420             430
   GAC TAC TGG GGT CAA GGA TCA CTA GTC ACT GTC TCC TGA GCC TCC ACC
                                                           Ala Ser Thr>
   Asp Tyr Trp Gly Gln Gly Ser Leu Val Thr Val Ser Ser>
``` to FIG. 16A

FIG. 16

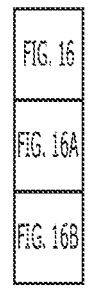

from FIG. 16

```
      440              450              460              470              480
AAG GGC CCA TCG GTC TTC CCC CTG GCA CCC TCC TCC AAG AGC ACC TCT
Lys Gly Pro Ser Val Phe Pro Leu Ala Pro Ser Ser Lys Ser Thr Ser>
      490              500              510              520              530
GGG GGC ACA GCG GCC CTG GGC TGC CTG GTC AAG GAC TAC TTC CCC GAA
Gly Gly Thr Ala Ala Leu Gly Cys Leu Val Lys Asp Tyr Phe Pro Glu>
      540              550              560              570              580
CCG GTG ACG GTG TCG TGG AAC TCA GGC GCC CTG ACC AGC GGC GTG CAC
Pro Val Thr Val Ser Trp Asn Ser Gly Ala Leu Thr Ser Gly Val His>
      590              600              610              620
ACC TTC CCG GCT GTC CTA CAG TCC TCA GGA CTC TAC TCC CTC AGC AGC
Thr Phe Pro Ala Val Leu Gln Ser Ser Gly Leu Tyr Ser Leu Ser Ser>
630           640              650              660              670
GTG GTG ACC GTG CCC TCC AGC AGC TTG GGC ACC CAG ACC TAC ATC TGC
Val Val Thr Val Pro Ser Ser Ser Leu Gly Thr Gln Thr Tyr Ile Cys>
680           690              700              710              720
AAC GTG AAT CAC AAG CCC AGC AAC ACC AAG GTG GAC AAG AAA GTT GAG
Asn Val Asn His Lys Pro Ser Asn Thr Lys Val Asp Lys Lys Val Glu>
      730              740              750              760              770
CCC AAA TCT TGT GAC AAA ACT CAC ACA TGC CCA CCG TGC CCA GCA CCT
Pro Lys Ser Cys Asp Lys Thr His Thr Cys Pro Pro Cys Pro Ala Pro>
      780              790              800              810              820
GAA CTC CTG GGG GGA CCG TCA GTC TTC CTC TTC CCC CCA AAA CCC AAG
Glu Leu Leu Gly Gly Pro Ser Val Phe Leu Phe Pro Pro Lys Pro Lys>
      830              840              850              860
GAC ACC CTC ATG ATC TCC CGG ACC CCT GAG GTC ACA TGC GTG GTG GTG
Asp Thr Leu Met Ile Ser Arg Thr Pro Glu Val Thr Cys Val Val Val>
870           880              890              900              910
GAC GTG AGC CAC GAA GAC CCT GAG GTC AAG TTC AAC TGG TAC GTG GAC
Asp Val Ser His Glu Asp Pro Glu Val Lys Phe Asn Trp Tyr Val Asp>
``` to FIG. 16B

FIG. 16A from FIG. 16A

```
       920             930             940             950             960
GGC GTG GAG GTG CAT AAT GCC AAG ACA AAG CCG CGG GAG GAG CAG TAC
Gly Val Glu Val His Asn Ala Lys Thr Lys Pro Arg Glu Glu Gln Tyr>

970             980             990            1000            1010
AAC AGC ACG TAC CGT GTG GTC AGC GTC CTC ACC GTC CTG CAC CAG GAC
Asn Ser Thr Tyr Arg Val Val Ser Val Leu Thr Val Leu His Gln Asp>

1020            1030            1040            1050            1060
TGG CTG AAT GGC AAG GAG TAC AAG TGC AAG GTC TCC AAC AAA GCC CTC
Trp Leu Asn Gly Lys Glu Tyr Lys Cys Lys Val Ser Asn Lys Ala Leu>

1070            1080            1090            1100
CCA GCC CCC ATC GAG AAA ACC ATC TCC AAA GCC AAA GGG CAG CCC CGA
Pro Ala Pro Ile Glu Lys Thr Ile Ser Lys Ala Lys Gly Gln Pro Arg>

1110            1120            1130            1140            1150
GAA CCA CAG GTG TAC ACC CTG CCC CCA TCC CGG GAT GAG CTG ACC AAG
Glu Pro Gln Val Tyr Thr Leu Pro Pro Ser Arg Asp Glu Leu Thr Lys>

1160            1170            1180            1190            1200
AAC CAG GTC AGC CTG ACC TGC CTG GTC AAA GGC TTC TAT CCC AGC GAC
Asn Gln Val Ser Leu Thr Cys Leu Val Lys Gly Phe Tyr Pro Ser Asp>

1210            1220            1230            1240            1250
ATC GCC GTG GAG TGG GAG AGC AAT GGG CAG CCG GAG AAC AAC TAC AAG
Ile Ala Val Glu Trp Glu Ser Asn Gly Gln Pro Glu Asn Asn Tyr Lys>

1260            1270            1280            1290            1300
ACC ACG CCT CCC GTG CTG GAC TCC GAC GGC TCC TTC TTC CTC TAC AGC
Thr Thr Pro Pro Val Leu Asp Ser Asp Gly Ser Phe Phe Leu Tyr Ser>

1310            1320            1330            1340
AAG CTC ACC GTG GAC AAG AGC AGG TGG CAG CAG GGG AAC GTC TTC TCA
Lys Leu Thr Val Asp Lys Ser Arg Trp Gln Gln Gly Asn Val Phe Ser>

1350            1360            1370            1380            1390
TGC TCC GTG ATG CAT GAG GCT CTG CAC AAC CAC TAC ACG CAG AAG AGC
Cys Ser Val Met His Glu Ala Leu His Asn His Tyr Thr Gln Lys Ser>

1400            1410
CTC TCC CTG TCT CCG GGT AAA
Leu Ser Leu Ser Pro Gly Lys>
```

FIG. 16B

Humanised 323/A3 (IgG4cys) Heavy Chain cDNA Sequence
SEQ ID NOs: 6 and 7

```
          10            20            30            40            50
CGTAAGCTTC  ACAGATCCTC  ACC ATG GGA TGG AGC TGT ATC ATC CTC TTT CTG
                            Met Gly Trp Ser Cys Ile Ile Leu Phe Leu>

60            70            80            90            100
GTG GCA ACA GCT ACA GGT GTC CAC TCC CAG GTA CAG CTA GTG CAA TCA
Val Ala Thr Ala Thr Gly Val His Ser>
                                    Gln Val Gln Leu Val Gln Ser>

110           120           130           140
GGG CCT GAA GTG AAG AAG CCT GGG GCC TCA GTG AAA GTT TCC TGC AAG
Gly Pro Glu Val Lys Lys Pro Gly Ala Ser Val Lys Val Ser Cys Lys>

150           160           170           180           190
GCT TCT GGC TAC ACC TTC ACC AAC TAT GGA ATG AAC TGG GTA AGG CAG
Ala Ser Gly Tyr Thr Phe Thr Asn Tyr Gly Met Asn Trp Val Arg Gln>

200           210           220           230           240
GCG CCT GGA CAG GGG CTT GAG TGG ATG GGG TGG ATA AAC ACC TAC ACT
Ala Pro Gly Gln Gly Leu Glu Trp Met Gly Trp Ile Asn Thr Tyr Thr>

250           260           270           280           290
GGA GAG CCA ACA TAT GGT GAA GAT TTC AAG GGA CGG TTT GCA TTC TCT
Gly Glu Pro Thr Tyr Gly Glu Asp Phe Lys Gly Arg Phe Ala Phe Ser>

300           310           320           330           340
CTA GAC ACA TCC GCC AGC ACA GCC TAT ATG GAG CTC AGC TCG CTG AGA
Leu Asp Thr Ser Ala Ser Thr Ala Tyr Met Glu Leu Ser Ser Leu Arg>

350           360           370           380
TCC GAG GAC ACT GCA GTC TAT TTC TGT GCG AGA TTT CGT AAC TAC GTA
Ser Glu Asp Thr Ala Val Tyr Phe Cys Ala Arg Phe Gly Asn Tyr Val>

390         400           410           420           430
GAC TAC TGG GGT CAA GGA TCA CTA GTC ACT GTC TCC TCA GCT TCC ACC
                                                        Ala Ser Thr>
Asp Tyr Trp Gly Gln Gly Ser Leu Val Thr Val Ser Ser>
440           450           460           470           480
AAG GGC CCA TCC GTC TTC CCC CTG GCG CCC TGC TCC AGG AGC ACC TCC
Lys Gly Pro Ser Val Phe Pro Leu Ala Pro Cys Ser Arg Ser Thr Ser>
``` to FIG. 17A

FIG. 17

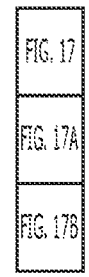

from FIG. 17

```
     490           500           510           520           530
GAG AGC ACA GCC GCC CTG GGC TGC CTG GTC AAG GAC TAC TTC CCC GAA
Glu Ser Thr Ala Ala Leu Gly Cys Leu Val Lys Asp Tyr Phe Pro Glu>
         540           550           560           570           580
CCG GTG ACG GTG TCG TGG AAC TCA GGC GCC CTG ACC AGC GGC GTG CAC
Pro Val Thr Val Ser Trp Asn Ser Gly Ala Leu Thr Ser Gly Val His>
             590           600           610           620
ACC TTC CCG GCT GTC CTA CAG TCC TCA GGA CTC TAC TCC CTC AGC AGC
Thr Phe Pro Ala Val Leu Gln Ser Ser Gly Leu Tyr Ser Leu Ser Ser>
 630           640           650           660           670
GTG GTG ACC GTG CCC TCC AGC AGC TTG GGC ACG AAG ACC TAC ACC TGC
Val Val Thr Val Pro Ser Ser Ser Leu Gly Thr Lys Thr Tyr Thr Cys>
 680           690           700           710           720
AAC GTA GAT CAC AAG CCC AGC AAC ACC AAG GTG GAC AAG AGA GTT GAG
Asn Val Asp His Lys Pro Ser Asn Thr Lys Val Asp Lys Arg Val Glu>
     730           740           750           760           770
TCC AAA TAT GGT CCC CCA TGC CCA CCG TGC CCT GCA CCT GAG TTC GCG
Ser Lys Tyr Gly Pro Pro Cys Pro Pro Cys Pro Ala Pro Glu Phe Ala>
         780           790           800           810           820
GGG GCA CCA TCA GTC TTC CTG TTC CCC CCA AAA CCC AAG GAC ACT CTC
Gly Ala Pro Ser Val Phe Leu Phe Pro Pro Lys Pro Lys Asp Thr Leu>
             830           840           850           860
ATG ATC TCC CGG ACC CCT GAG GTC ACG TGC GTG GTG GTG GAC GTG AGC
Met Ile Ser Arg Thr Pro Glu Val Thr Cys Val Val Val Asp Val Ser>
 870           880           890           900           910
CAG GAA GAC CCC GAG GTC CAG TTC AAC TGG TAC GTG GAT GGC GTG GAG
Gln Glu Asp Pro Glu Val Gln Phe Asn Trp Tyr Val Asp Gly Val Glu>
 920           930           940           950           960
GTG CAT AAT GCC AAG ACA AAG CCG CGG GAG GAG CAG TTC AAC AGC ACG
Val His Asn Ala Lys Thr Lys Pro Arg Glu Glu Gln Phe Asn Ser Thr>
``` to FIG. 17B

FIG. 17A from FIG. 17A

```
      970         980         990        1000        1010
TAC CGT GTG GTC AGC GTC CTC ACC GTC CTG CAC CAG GAC TGG CTG ACC
Tyr Arg Val Val Ser Val Leu Thr Val Leu His Gln Asp Trp Leu Asn>

1020        1030        1040        1050        1060
GGC AAG GCG TAC AAG TGC AAG GTC TCC AAC AAA GGC CTC CCG TCC TCC
Gly Lys Ala Tyr Lys Cys Lys Val Ser Asn Lys Gly Leu Pro Ser Ser>

1070        1080        1090        1100
ATC GAG AAA ACC ATC TCC AAA GCC AAA GGG CAG CCC CGA GAG CCA CAG
Ile Glu Lys Thr Ile Ser Lys Ala Lys Gly Gln Pro Arg Glu Pro Gln>

1110        1120        1130        1140        1150
GTG TAC ACC CTG CCC CCA TCC CAG GAG GAG ATG ACC AAG AAC CAG GTC
Val Tyr Thr Leu Pro Pro Ser Gln Glu Glu Met Thr Lys Asn Gln Val>

1160        1170        1180        1190        1200
AGC CTG ACC TGC CTG GTC AAA GGC TTC TAC CCC AGC GAC ATC GGG GTG
Ser Leu Thr Cys Leu Val Lys Gly Phe Tyr Pro Ser Asp Ile Ala Val>

1210        1220        1230        1240        1250
GAG TGG GAG AGC AAT GGG CAG CCG GAG AAC AAC TAC AAG ACC ACG CCT
Glu Trp Glu Ser Asn Gly Gln Pro Glu Asn Asn Tyr Lys Thr Thr Pro>

1260        1270        1280        1290        1300
CCC GTG CTG GAC TCC GAC GGC TCC TTC TTC CTC TAC AGC AGG CTA ACC
Pro Val Leu Asp Ser Asp Gly Ser Phe Phe Leu Tyr Ser Arg Leu Thr>

1310        1320        1330        1340
GTG GAC AAG AGC AGG TGG CAG GAG GGG AAT GTC TTC TCA TGC TCC GTG
Val Asp Lys Ser Arg Trp Gln Glu Gly Asn Val Phe Ser Cys Ser Val>

1350        1360        1370        1380        1390
ATG CAT GAG GCT CTG CAC AAC CAC TAC ACA CAG AAG AGC CTC TGC CTG
Met His Glu Ala Leu His Asn His Tyr Thr Gln Lys Ser Leu Cys Leu>

1400        1410
TCT CTG GGT AAA T  GAGAATTC
Ser Leu Gly Lys>
```

FIG. 17B

Humanised 323/A3 (IgG$_{2cys}$) Heavy Chain cDNA Sequence
SEQ ID NOs: 8, 9 and 10

```
          10          20          30          40          50          60
ATGGATTGGC  TGTGGAACTT  GCTATTCCTG  ATGGCAGCTG  CCCAAAGTAT  CCAAGCA CAG
TACCTAACCG  ACACCTTGAA  CGATAAGGAC  TACCGTCGAC  GGGTTTCATA  GGTTCGT GTC
                                                                    Gln>
          70          80          90         100
ATC CAG TTG GTG CAG TCT GGA CCT GAA CTG AAG AAG CCT GGA GAG ACA
TAG GTC AAC CAC GTC AGA CCT GGA CTT GAC TTC TTC GGA CCT CTC TGT
Ile Gln Leu Val Gln Ser Gly Pro Glu Leu Lys Lys Pro Gly Glu Thr>
110         120         130         140         150
GTC AAG ATC TCC TGC AAG GCT TCT GGA TAT ACC TTC ACA AAC TAT GGA
CAG TTC TAG AGG ACG TTC CGA AGA CCT ATA TGG AAG TGT TTG ATA CCT
Val Lys Ile Ser Cys Lys Ala Ser Gly Tyr Thr Phe Thr Asn Tyr Gly>
    160         170         180         190         200
ATG AAC TGG GTG AGG CAG GCT TCA GGA GAG GGT TTA AAG TGG ATG GGC
TAC TTG ACC CAC TCC GTC CGA AGT CCT CTC CCA AAT TTC ACC TAC CCG
Met Asn Trp Val Arg Gln Ala Ser Gly Glu Gly Leu Lys Trp Met Gly>
    210         220         230         240         250
TGG ATA AAC ACC TAC ACT GGA GAG CCA ACA TAT GGT GAA GAT TTC AAG
ACC TAT TTG TGG ATG TGA CCT CTC GGT TGT ATA CCA CTT CTA AAG TTC
Trp Ile Asn Thr Tyr Thr Gly Glu Pro Thr Tyr Gly Glu Asp Phe Lys>
    260         270         280         290         300
GGA CGG TTT GCC TTC TCT TTG GAA ACC TCT GCC AGC ACT GCC TAT TTG
CCT GCC AAA CGG AAG AGA AAC CTT TGG AGA CGG TCG TGA CGG ATA AAC
Gly Arg Phe Ala Phe Ser Leu Glu Thr Ser Ala Ser Thr Ala Tyr Leu>
    310         320         330         340
CAG ATC AAC AAC CTC AAA AAT GAA GAC ACG GCT ACA TAT TTC TGT GCA
GTC TAG TTG TTG GAG TTT TTA CTT CTG TGC CGA TGT ATA AAG ACA CGT
Gln Ile Asn Asn Leu Lys Asn Glu Asp Thr Ala Thr Tyr Phe Cys Ala>
350         360         370         380         390
AGA TTT GGT AAC TAC GTA GAC TAC TGG GGC CAA GGC ACC ACT CTC ACA
TCT AAA CCA TTG ATG CAT CTG ATG ACC CCG GTT CCG TGG TGA GAG TGT
Arg Phe Gly Asn Tyr Val Asp Tyr Trp Gly Gln Gly Thr Thr Leu Thr>
    400         410         420         430         440
GTC TCC TCA GCC TCC ACC AAG GGC CCA TCG GTC TTC CCC CTG GCG CCC
CAG AGG AGT CGG AGG TGG TTC CCG GGT AGC CAG AAG GGG GAC CGC GGG
Val Ser Ser>
            Ala Ser Thr Lys Gly Pro Ser Val Phe Pro Leu Ala Pro>
    450         460         470         480         490
TGC TCC AGG AGC ACC TCC GAG AGC ACA GCG GCC CTG GGC TGC CTG GTC
ACG AGG TCC TCG TGG AGG CTC TCG TGT CGC CGG GAC CCG ACG GAC CAG
Cys Ser Arg Ser Thr Ser Glu Ser Thr Ala Ala Leu Gly Cys Leu Val>
``` to FIG. 18A

FIG. 18

| FIG. 18 |
| FIG. 18A |
| FIG. 18B | from FIG. 18

```
       500              510              520              530              540
AAG GAC TAC TTC CCC GAA CCG GTG ACG GTG TCG TGG AAC TCA GGC GCT
TTC CTG ATG AAG GGG CTT GGC CAC TGC CAC AGC ACC TTG AGT CCG CGA
Lys Asp Tyr Phe Pro Glu Pro Val Thr Val Ser Trp Asn Ser Gly Ala>
            550              560              570              580
CTG ACC AGC GGC GTG CAC ACC TTC CCA GCT GTC CTA CAG TCC TCA GGA
GAC TGG TCG CCG CAC GTG TGG AAG GGT CGA CAG GAT GTC AGG AGT CCT
Leu Thr Ser Gly Val His Thr Phe Pro Ala Val Leu Gln Ser Ser Gly>
590              600              610              620              630
CTC TAC TCC CTC AGC AGC GTG GTG ACC GTG CCC TCC AGC AAC TTC GGC
GAG ATG AGG GAG TCG TCG CAC CAC TGG CAC GGG AGG TCG TTG AAG CCG
Leu Tyr Ser Leu Ser Ser Val Val Thr Val Pro Ser Ser Asn Phe Gly>
     640              650              660              670              680
ACC CAG ACC TAC ACC TGC AAC GTA GAT CAC AAG CCC AGC AAC ACC AAG
TGG GTC TGG ATG TGG ACG TTG CAT CAT GTG TTC GGG TCG TTG TGG TTC
Thr Gln Thr Tyr Thr Cys Asn Val Asp His Lys Pro Ser Asn Thr Lys>
         690              700              710              720              730
GTG GAC AAG ACA GTT GAG CGC AAA TGT TGT GTC GAG TGC CCA CCG TGC
CAC CTG TTC TGT CAA CTC GCG TTT ACA ACA CAG CTC ACG GGT GGC ACG
Val Asp Lys Thr Val Glu Arg Lys Cys Cys Val Glu Cys Pro Pro Cys>
             740              750              760              770              780
CCA GCA CCA CCT GTG GCA GGA CCG TCA GTC TTC CTC TTC CCC CCA AAA
GGT CGT GGT GGA CAC CGT CCT GGC AGT CAG AAG GAG AAG GGG GGT TTT
Pro Ala Pro Pro Val Ala Gly Pro Ser Val Phe Leu Phe Pro Pro Lys>
                 790              800              810              820
CCC AAG GAC ACC CTC ATG ATC TCC CGG ACC CCT GAG GTC ACG TGC GTG
GGG TTC CTG TGG GAG TAC TAG AGG GCC TGG GGA CTC CAG TGC ACG CAC
Pro Lys Asp Thr Leu Met Ile Ser Arg Thr Pro Glu Val Thr Cys Val>
830              840              850              860              870
GTG GTG GAC GTG AGC CAC GAA GAC CCC GAG GTC CAG TTC AAC TGG TAC
CAC CAC CTG CAC TCG GTG CTT CTG GGG CTC CAG GTC AAG TTG ACC ATG
Val Val Asp Val Ser His Glu Asp Pro Glu Val Gln Phe Asn Trp Tyr>
     880              890              900              910              920
GTG GAC GGC GTG GAG GTG CAT AAT GCC AAG ACA AAG CCA CGG GAG GAG
CAC CTG CCG CAC CTC CAC GTA TTA CGG TTC TGT TTC GGT GCC CTC CTC
Val Asp Gly Val Glu Val His Asn Ala Lys Thr Lys Pro Arg Glu Glu>
         930              940              950              960              970
CAG TTC AAC AGC ACG TTC CGT GTG GTC AGC GTC CTC ACC GTT GTG CAC
GTC AAG TTG TCG TGC AAG GCA CAC CAG TCG CAG GAG TGG CAA CAC GTG
Gln Phe Asn Ser Thr Phe Arg Val Val Ser Val Leu Thr Val Val His>
             980              990              1000             1010             1020
CAG GAC TGG CTG AAC GGC AAG GAG TAC AAG TGC AAG GTC TCC AAC AAA
GTC CTG ACC GAC TTG CCG TTC CTC ATG TTC ACG TTC CAG AGG TTG TTT
Gln Asp Trp Leu Asn Gly Lys Glu Tyr Lys Cys Lys Val Ser Asn Lys>
``` to FIG. 18B

FIG. 18A from FIG. 18A

```
         1030              1040              1050              1060
   GGC CTC CCA GCC CCC ATC GAG AAA ACC ATC TCC AAA ACC AAA GGG CAG
   CCG GAG GGT CGG GGG TAG CTC TTT TGG TAG AGG TTT TGG TTT CCC GTC
   Gly Leu Pro Ala Pro Ile Glu Lys Thr Ile Ser Lys Thr Lys Gly Gln>
1070          1080              1090              1100          1110
   CCC CGA GAA CCA CAG GTG TAC ACC CTG CCC CCA TCC CGG GAG GAG ATG
   GGG GCT CTT GGT GTC CAC ATG TGG GAC GGG GGT AGG GCC CTC CTC TAC
   Pro Arg Glu Pro Gln Val Tyr Thr Leu Pro Pro Ser Arg Glu Glu Met>
1120          1130              1140              1150          1160
   ACC AAG AAC CAG GTC AGC CTG ACC TGC CTG GTC AAA GGC TTC TAC CCC
   TGG TTC TTG GTC CAG TCG GAC TGG ACG GAC CAG TTT CCG AAG ATG GGG
   Thr Lys Asn Gln Val Ser Leu Thr Cys Leu Val Lys Gly Phe Tyr Pro>
          1170           1180              1190         1200          1210
   AGC GAC ATC GCC GTG GAG TGG GAG AGC AAT GGG CAG CCG GAG AAC AAC
   TCG CTG TAG CGG CAC CTC ACC CTC TCG TTA CCC GTC GGC CTC TTG TTG
   Ser Asp Ile Ala Val Glu Trp Glu Ser Asn Gly Gln Pro Glu Asn Asn>
            1220              1230              1240          1250          1260
   TAC AAG ACC ACA CCT CCC ATG CTG GAC TCC GAC GGC TCC TTC TTC CTC
   ATG TTC TGG TGT GGA GGG TAC GAC CTG AGG CTG CCG AGG AAG AAG GAG
   Tyr Lys Thr Thr Pro Pro Met Leu Asp Ser Asp Gly Ser Phe Phe Leu>
            1270              1280              1290          1300
   TAC AGC AAG CTC ACC GTG GAC AAG AGC AGG TGG CAG CAG GGG AAC GTC
   ATG TCG TTC GAG TGG CAC CTG TTC TCG TCC ACC GTC GTC CCC TTG CAG
   Tyr Ser Lys Leu Thr Val Asp Lys Ser Arg Trp Gln Gln Gly Asn Val>
1310          1320              1330              1340          1350
   TTC TCA TGC TCC GTG ATG CAT GAG GCT CTG CAC AAC CAC TAC ACA CAG
   AAG AGT ACG AGG CAC TAC GTA CTC CGA GAC GTG TTG GTG ATG TGT GTC
   Phe Ser Cys Ser Val Met His Glu Ala Leu His Asn His Tyr Thr Gln>
      1360              1370              1380              1390
   AAG AGC CTC TGC CTG TCT CTG GGT AAA TGAGAAT TC
   TTC TCG GAG ACG GAC AGA GAC CCA TTT ACTCTTA AG
   Lys Ser Leu Cys Leu Ser Leu Gly Lys>
```

FIG. 18B

COMBINATION OF AN ANTI-EP-CAM ANTIBODY WITH A CHEMOTHERAPEUTIC AGENT

This application is a continuation of U.S. patent application Ser. No. 11/034,655 filed Jan. 13, 2005, now granted as U.S. Pat. No. 7,648,703, which is a continuation of U.S. application Ser. No. 10/031,355 filed Jan. 18, 2002, now abandoned, which was filed pursuant to 35 U.S.C. §371 as a United States National Phase application of International Application No. PCT/EP99/05271 filed Jul. 23, 1999.

This present invention relates to the combination of antibodies that specifically bind to the EP-CAM antigen with chemotherapeutic agents that affect cell growth by blocking progression of the cell cycle in $G_2/M$ and their use in therapy of cancers which express the antigen.

The conventional therapeutic approaches to cancer include surgery, radiotherapy and chemotherapy in various combinations; however, response rates have not improved significantly in the last 20 years. The major limitation of chemotherapy and radiotherapy is the non-selective targeting of both normal and tumour cells that results in toxic side effects. In the search for less toxic and more specific treatment alternatives, various types of immunotherapy have been investigated. Among these modalities, strategies based on monoclonal antibodies have been applied to a broad spectrum of malignancies (Riethmüller et al., Curr Opin Immun 1992, 4, 647-655 and Riethmüller et al., Curr Opin Immunol 1993, 5, 732-739). The utility of monoclonal antibodies is based upon their clonal antigen specificity, i.e., molecular recognition of specific epitopes which may comprise an antigen and to bind to these antigens with high affinity. Monoclonal antibodies can bind to antigens expressed uniquely or preferentially on the surface of malignant cells, and hence can be used to specifically target and destroy tumour cells. Antibodies may be constructed as delivery vehicles for drugs or DNA, or as conjugates with radionuclides. Binding of naked antibody to target cells may also activate innate antitumour immune functions such as antibody-dependent cell-mediated cytotoxicity (ADCC) and complement-mediated cytotoxicity (CMC), either of which may result in lysis or phagocytosis of the targeted cell. Both ADCC and CMC are antibody-dose-related immune functions and it is therefore desirable to get as much antibody bound to target cells as possible. One way of achieving this objective is to increase the level of expression of the relevant antigen which may effectively increase antibody functions such as, for example, ADCC of the target cells by virtue of getting more antibody bound to the cells (Fogler et al., Cancer Research 48:6303-6308 (1988)).

One antigen of importance in cancer therapy is the Ep-CAM antigen (human pan-carcinoma antigen). This antigen is a transmembrane glycoprotein which has been reported to function as a cell adhesion molecule (Litvinow et al., J. Cell Biology 125:437-446, 1994) and is also known as the 17-1A antigen, 40 kD antigen, EGP40, GA733-2, KSA and ESA but may be known by other names or descriptions in the literature as well. It is expressed on the baso-lateral surface of a majority of simple cuboidal or columnar, pseudo stratified columnar and transitional epithelia and at generally higher levels in tumour cells. Epithelial cells are known to be the most important cell type in the development of human malignancies. Thus more than 90% of all malignant tumours are carcinomas, and therefore of epithelial origin (Acta Anatomica; 156 (3):217-226 (1996)). Although the Ep-CAM antigen is expressed on most tumour cells of epithelial origin there are examples of cells of epithelal origin that do not express Ep-CAM such as adult epithelial tissues, epidermal adult keratinocytes, gastric parietal cells, thymic cortical epithelium, myoepithelial cells and hepatocytes. The phenotype of a malignant cell plays an important role in the efficacy of monoclonal antibodies. While tumour specific antigens have proven to be elusive, differences in expression of the antigens between normal cells and tumour cells have provided a means to target antibodies to tumours. It would be clinically advantageous to improve on these differences by enhancement of antigen homogeneity and density of expression on tumour cells.

Interferons are well-known to alter cell phenotypes by increasing expression of tumour antigens as well as many normal antigens, e.g., Class I HLA. For example, human recombinant interferon-α and interferon-γ can increase the expression of human tumour antigens TAG-72 and CEA (Greiner et al., Cancer Res 44:3208-3214 (1984)). Interferon exposure induced a more homogeneous CEA-positive tumour cell population which shed more CEA from the cells surface, which was confirmed by in vivo studies with human carcinoma xenografts in athymic mice. Treatment with interferon-γ enhanced TAG-72 and CEA expression on ovarian or gastrointestinal tumour cells in patients' malignant ascites (Greiner et al., J Clin Oncol 10:735-746 (1992)).

The effects of interferons on cells are myriad and range from direct cytotoxicity to immunopotentiation to antiproliferative activity. None of the effects of interferons on antigen expression have been directly ascribed to interference with cell cycle progression.

Briefly, cell cycle progression refers to the sequence of events between one mitotic division and another in a cell. A quiescent resting phase ($G_0$) is followed by a growth phase ($G_1$), then by a DNA synthesis phase (S). A second growth phase of cell enlargement ($G_2$) and DNA replication (M phase) is followed by division of the cell into two progeny cells. Any interference with the cell machinery may inhibit all cycle progression at any phase of the cell cycle. For example, specific chemotherapeutic agents may block progression in either $G_2$ or M or in both $G_2$ and M ($G_2/M$). In other words exposure to certain drugs e.g., chemotherapeutic agents will for example, arrest individual cells in $G_2$ and/or M until eventually most, or all of the cells in a population become arrested in $G_2$ and/or M ($G_2/M$). In HeLa cells, for example, the $G_1$, S, $G_2$ and M phase take 8.2, 6.2, 4.6 and 0.6 hours, respectively. The period between mitoses is called interphase. Cells may have different doubling times, depending on their developmental stage or tissue type. The variation in doubling times is usually a function of the time spent in $G_1$ (A Dictionary of Genetics, 5th edition, R C King and W D Stansfield, Oxford University Press, 1997).

While a few proteins have been identified as produced solely at certain phases of the cell cycle, and therefore can serve as markers of cell cycle status, most others are produced across the cell cycle but at higher or lower levels at certain points. Variation of antigen density across the cell cycle is typical for the sarcoma antigens p102 and p200 (Song S, Anticancer Research 16(3A):1171-5 (1996)), the leukaemia/lymphoma-associated antigen JD118 (Czuczman et al., Cancer Immunology, Immunotherapy 36(6):387-96 (1993)), and the gastric tumour antigen PC1 (Wei et al., J of Oncology 9(3):179-82 (1987)). A few tumour antigens have been reported to be cell-cycle independent, e.g., liver metastases 3H4 (Wulf et al., J. Cancer Research and Clinical Oncology 122(8):476-82 (1996)) and small cell lung cancer antigens (Fargion et al., Cancer Research 46:2633-2638 (1986)).

Surprisingly, it has been found that pre-treatment with a drug, for example a chemotherapeutic agent known to block cell cycle progression at S and/or $G_2/M$ results in a significant increase in the density of the Ep-CAM antigen population and thus in greater targeting of anti-Ep-CAM antibodies to Ep-CAM expressing tumours. In lytic antibodies this translates into an increased susceptibility to antibody-dependent cytolysis. This perturbation of tumour cell phenotype has a significant impact on the biological effectiveness of therapeutic antibodies, and provides synergistic benefit to standard chemotherapeutic regimens. Furthermore, this increase in Ep-CAM antigen expression appears to be tumour specific. In other words, pre-treatment with chemotherapeutic agents that block the cell cycle at S and/or $G_2$/M does not seem to affect Ep-CAM antigen expression in non-tumour cells.

Accordingly, the present invention provides a combination of an Ep-CAM antibody and a chemotherapeutic agent that is capable of arresting Ep-CAM antigen expressing cells in S or $G_2$/M, preferably in $G_2$/M.

Examples of anti-Ep-CAM antibodies are ING1 (Colcher et al., Proc. Natl. Acad. Sci. USA, 78 (5), 3199 to 3203 (1981) and Laio et al., Human Antibody Hybridomas 1(2), 66-76 (1990)); 17-1A e.g., PANOREX® (Herlyn et al., Proc. Natl. Acad. Sci. USA 76:1438-1452 (1979) and Herlyn et al., Hybridoma 1985; 5 (suppl. 1) S3 to S10); and NR-LU-10 (Okabe et al., Cancer Research, 44, 5273 to 5278 (1984)).

PANOREX® (ADJUQUAL®) is a 17.1A mouse monoclonal antibody. It is marketed by Glaxo Wellcome in Germany for the post-operative adjuvant therapy of colorectal cancer.

An example of an anti-Ep-CAM antibody is one with the variable light chain cDNA sequence as set out in FIG. 15 and the heavy chain cDNA sequence as set out in FIG. 16. (known as humanised 323/A3/IgG$_1$). Two further preferred examples of anti-Ep-CAM antibodies are those with the variable light chain cDNA sequence as set out in FIG. 15 and heavy chain cDNA sequences as set out in FIG. 17 or 18 respectively (known as humanised 323/A3 IgG$_4$ and IgG$_2$cys respectively).

A preferred example of an anti-Ep-CAM antibody is 17.1A, most preferably PANOREX®.

Specific anti-Ep-CAM antibodies can be given on their own or in combination with other anti-Ep-CAM antibodies. Examples of such anti-Ep-CAM antibody combinations are an anti-Ep-CAM antibody with the variable light chain cDNA sequence as set out in FIG. 15 and the heavy chain cDNA sequence as set out in FIG. 16 in combination with ING1. Thus throughout the specification reference to an anti-Ep-CAM antibody includes antibody combinations of various anti-Ep-CAM antibodies, preferably non-competing anti-Ep-CAM antibodies targeting different epitopes on the same Ep-CAM antigen. Examples of chemotherapeutic agents which are capable of arresting Ep-CAM antigen expressing cells in $G_2$/M are vinorelbine, cisplatin, mytomycin, paclitaxel, carboplatin, oxaliplatin and CPT-11 (camptothecin 11).

Vinorelbine tartrate is a semisynthetic vinca alkaloid with the chemical name 3',4'-didehydro-4'-deoxy-C'-norvincaleukoblastine [R-(R*,R*)-2,3-dihydroxybutanedioate (1:2) (salt)]. Vinorelbine tartrate is used in combination with other chemotherapy agents such as cisplatin or as a single agent in the treatment of various solid tumours particularly non-small cell lung, advanced breast, and hormone refractory prostate cancers. The brand name NAVELBINE® is used in North America and Europe. NAVELBINE® is administered intravenously as a single-agent or in combination therapy typically at doses of 20-30 mg/m$^2$ on a weekly basis. An oral formulation of vinorelbine is in clinical development.

Cisplatin has the chemical name cis-diamminedichloroplatinum. Cisplatin is used in the treatment of metastatic testicular tumours as a combination therapy, as single and combination therapy in metastatic ovarian tumours, as well as a single agent in advanced bladder cancer. Cisplatin is manufactured by Bristol-Myers Squibb under the brand names of PLATINOL® and PLATINOL-AQ®. Cisplatin is also used in the following types of cancer, typically in combination therapy: non-small cell and small cell lung cancers, head and neck, endometrial, cervical, and non-Hodgkin's lymphoma. Cisplatin is typically administered intravenously in doses ranging from 15-150 mg/m$^2$ once every 3 to 4 weeks, or daily for 5 days repeated every 3 or 4 weeks. However, higher and more frequent doses are occasionally administered and the route of administration could be different than intravenous, such as intra-arterial or intraperitoneal.

Carboplatin has the chemical name platinum, diammine [1,1-cyclobutane-dicarboxylato(2)-O,O']-(SP-4-2). Carboplatin is usually administered in combination with other cytotoxics such as paclitaxel and etoposide. It is used in the treatment of advanced ovarian cancer, non-small cell lung cancer as well as in many of the same types of cancer as cisplatin is used. The brand name of carboplatin manufactured by Bristol-Myers Squibb is PARAPLATIN®. Carboplatin is typically administered intravenously at 300-400 mg/m$^2$, or to a target area under the drug concentration versus time curve (AUC) of 4-6 mg/ml-min using the patient's estimated glomerular filtration rate (GFR). Higher doses up to around 1600 mg/m$^2$ divided over several, usually five, days may also be administered.

Paclitaxel has the chemical name 5β,20 epoxy-1,2α,4,7β, 10β,13α-hexahydroxytax-11-en-9-one 4,10-diacetate 2-benzoate 13-ester with (2R,3S)-N-benzoyl-3-phenylisoserine. Paclitaxel is manufactured by Bristol-Myers Squibb as TAXOL®. It is used to treat a variety of carcinomas including ovarian, breast, non-small cell lung, head and neck. Typical doses include 135-175 mg/m$^2$ as either a 3 or 24 hour intravenous infusion given every 3 or 4 weeks. Higher doses up to around 300 mg/m$^2$ have also been administered.

Besides the active ingredient, the drug products provided by manufacturers typically contain a diluent such as sterile water, dextrose 5% in water or 0.9% sodium chloride in water with additional excipients such as CREMOPHOR® vehicle added to make for example, paclitaxel soluble.

More detailed information on treatment regimes, dosages and compositions etc. can be obtained from standard reference books such as: Martindale, The Extra Pharmacopoeia, 31st edition, edited by JEF Reynolds, London, Royal Pharmaceutical Society, 1996 and the Physicians Desk reference, 49th Edition, 1995, Medical Economics Data Production Company, Montvale.

Other chemotherapeutic agents that may cause cells to accumulate in $G_2$/M include anthracyclines e.g., doxorubicin and aclarubicin; carmustine (BCNU), camptothecin, 9-nitrocamptothecin, cyclophosphamide and its derivatives, docetaxel, etoposide, razoxane (ICRF-187), alkyllyso-phospholipids e.g., ilmofosine; methotrexate, MST-16, taxanes, vinblastine, vincristine and teniposide (VM-26) (again see Martindale, The Extra Pharmacopoeia, 31st edition, edited by JEF Reynolds, London, Royal Pharmaceutical Society, 1996,) and flavonoids e.g., apigenin and genistein (see The Merck Index, 12th edition, Merck Research Laboratories, Merck and Co Inc, 1996). In addition, adozelesin (a class of pyrazole compounds) (Cancer Research 1992, Oct. 15; 52(2): 5687 to 5692)), bistratene A (Mutation Research 1996, Mar. 1; 367 (3):169 to 175), cycloxazoline (Cancer Chemotherapy & Pharmacology 1994; 33 (5):399 to 409), imidazoarcridinone, melephan (Experimental Cell Biology 1986; 54 (3):138 to 148 and International Journal of Cancer 1995, Jul. 17; 62 (2):170 to 175), merbarone (Environmental & Molecular Mutagenesis 1997; 29 (1):16 to 27 and Cancer Research 1995, Apr. 1; 55 (7):1509 to 1516) and oracin (FEBS Letters 1997, Jan. 2; 400 (1):127 to 130) are also believed to cause cells to accumulate in $G_2/M$ generally all topo II inhibitors, e.g., to potecan (ABPI, 1998-1999), all vinca derivatives and all DNA damaging agents including radiation are also believed to arrest cells in $G_2/M$.

Moreover, 5FU has been reported to arrest cells in $G_2/M$ (Oncology Research 1994; 6(7):303-309) and it is therefore believed that 5FU and compounds similar to 5FU such as UFT, methotrexate, capecitabine and gemcitabine will increase Ep-Cam expression in some tissues. Similarly, TOMUDEX® (raltitrexed) which is known to arrest cells in the S phase is believed to increase Ep-Cam expression.

The term "chemotherapeutic agent" throughout the specification is therefore not limited to cytotoxic therapy, but also encompasses cytostatic therapy and any other drugs capable of stopping cells in $G_2/M$. It should be further noted that radiotherapy is capable of arresting cells in $G_2/M$ and that throughout the specification the term chemotherapeutic can therefore be substituted with "radiotherapy".

Throughout the specification reference to a chemotherapeutic agent includes combinations of one or more specific chemotherapeutic agents which arrest Ep-CAM expressing tumour cells in $G_2/M$. Examples of typical combinations are vinorelbine with cisplatin and paclitaxel with carboplatin; oxaliplatin with 5FU; cyclophosphamide with methotrexate and 5FU; cyclophosphamide with doxorubicin and 5FU.

While it is possible for the chemotherapeutic agent to be administered alone it is preferable to present it as a pharmaceutical composition comprising an active ingredient, as defined above, together with an acceptable carrier therefor. Each carrier must be "acceptable" in the sense of being compatible with the other ingredients of the composition and not injurious to the recipient.

Preferred combinations of an Ep-Cam antibody and a chemotherapeutic agent(s) that are capable of arresting Ep-CAM antigen expressing cells in S or $G_2/M$ are: PANOREX® in combination with any of the following chemotherapeutic agents: UFT, capecitabine, CPT-11, oxaliplatin, 5FU, 5FU continuous infusion, paclitaxel, docetaxel, cyclophosphamide, methotrexate, doxorubicin, NAVELBINE® (iv and oral), epirubicin, mitoxantrone, raloxifen, cisplatin, mitomycin, carboplatinum, gemcitabine, etoposide and topotecan.

Particularly preferred combinations are PANOREX® with CPT-11, 5FU (continuous infusion), oxaliplatin, capecitibine, UFT and TOMUDEX® (raltitrexed).

These PANOREX® combinations are useful in the treatment of cancer, particualrly in the treatment of colorectal cancer, breast cancer, gastric cancer, prostate cancer and non-small-cell lung cancer.

Specifically, the following combinations are particualrly preferred for colorectal cancer: PANOREX® in combination with: UFT (optionally with leucovorin); capecitabine; oxaliplatin (optionally with 5FU); CPT-11, 5FU (optionally with eniluracil or levamisole or leucovorin); 5FU protacted continuous infusion; and mitomycin.

Preferred combinations for the treatment of breast cancer are: PANOREX® in combination with paclitaxel; docetaxel; cyclophosphamide (optionally with 5FU and either methotrexate or doxorubicin); NAVELBINE® (iv and/or oral); doxorubicine; epirubicin; mitoxantrone; and raloxifin.

Preferred combinations for the treatment of gastric cancer are: PANOREX® in combination with cisplatin; 5FU; mitomycin; and carboplatinum.

A preferred combination for the treatment of prostatic cancer is: PANOREX® in combination with mitoxantrone.

Preferred combinations for the treatment of non-small-cell lung cancer are: PANOREX® in combination with: NAVELBINE®; cisplatin; carboplatin; paclitaxel; docetaxel; gemcitabine; topotecan; and etoposide.

Information regarding dosing of PANOREX® and the above chemotherapeutic agents given in combination with PANOREX® can be found in standard reference books such as ABPI, Compendium of Data Sheets and Summaries of Product Characteristics, Datapharm Publications Limited, 1998-1999.

The compositions include those suitable for oral, rectal, nasal, topical (including buccal and sublingual), vaginal, parenteral (including subcutaneous, intramuscular, intravenous and intradermal) or transdermal administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Compositions of the chemotherapeutic agent suitable for oral administration may be presented as discrete units such as capsules, cachets or tablets each containing a predetermined amount of the active ingredient; as a powder or granules; as a solution or suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricants, inert diluent, preservative, disintegrant (e.g., sodium starch glycollate, cross-linked povidone, cross-linked sodium carboxymethyl cellullose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating to provide release in parts of the gut other than the stomach.

Compositions suitable for oral use as described above may also include buffering agents designed to neutralise stomach acidity. Such buffers may be chosen from a variety of organic or inorganic agents such as weak acids or bases admixed with their conjugated salts.

Composition suitable for topical administration in the mouth include lozenges comprising the active ingredient in a flavoured basis, usually sucrose and acacia or tragacanth; pastilles comprising the active ingredient in an inert basis such as gelatine and glycerin, or sucrose and acacia and mouthwashes comprising the active ingredient in a suitable carrier.

Compositions for rectal administration may be presented as a suppository with suitable base comprising for example cocoa butter or a salicylate.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bacteriostats and solutes which render the compositions isotonic with the blood of the intended recipient; and aqueous and non-aqueous sterile suspensions which may include suspending agents and thickening agents, such as liposomes or other microparticulate systems which are designed to target the compounds to blood components or one or more organs. The compositions may be presented in unit-dose or multi-dose sealed containers, for example, ampoules and vials, and may be stored in a freeze-dried (lyophilized) condition requiring only the addition of sterile liquid carrier, for example water for injections, immediately prior to use. Extemporaneous injection solutions and suspensions may be prepared from sterile powders, granules and tablets of the kind previously described.

Compositions suitable for transdermal administration may be presented as discrete patches adapted to remain in intimate contact with the epidermis of the recipient for a prolonged period of time. Such patches suitably contain the active ingredient as an optionally buffered, aqueous solution of, for example, 0.1 to 0.2 M concentration with respect to said compound. As one particular possibility, the active ingredient may be delivered from the patch by iontophoresis as generally described in Pharmaceutical Research, 3 (6), 318 (1986).

It should be understood that in addition to the ingredients particularly mentioned above the compositions in question, for example, those suitable for oral administration may include such further agents as sweeteners, thickeners and flavouring agents.

The dosage range of the chemotherapeutic agent to be co-administered with the antibody may typically be between about 1 to 1000 mg/m$^2$ (based on patient body surface area) or about 2 to 30 mg/kg (based on patient body weight), depending on the chemotherapeutic agent(s) used. Thus, for example, vinorelbine (NAVELBINE®) would typically be administered at a dosage of about 20 to 30 mg/m$^2$, cisplatin at about 15 to 100 mg/m$^2$ carboplatin at about 300 to 600 mg/m$^2$ and paclitaxel at about 100 to 300 mg/m$^2$, preferably around 135 to 175 mg/m$^2$. Another way of expressing dosage is by their AUC value. For example carboplatin would typically be administered at a dose calculated as AUC=4 to 6 mg/ml-min. Generally, the doses of chemotherapeutic agents are lower when given in combination with another chemotherapeutic agent and/or antibody than if given on their own as the single chemotherapeutic agent. The doses of chemotherapeutic agents that will be co-administered with anti Ep-CAM antibody(ies) will likely be the standard doses for the type of carcinoma treated or lower doses. In general the highest tolerated doses of the chemotherapeutic agents are administered either alone or in combination.

The anti-Ep-CAM antibodies of the present invention preferably have the structure of a natural antibody or a fragment thereof. Antibodies typically comprise two heavy chains linked together by disulphide bonds and two light chains. Each light chain is linked to a respective heavy chain by disulphide bonds. Each heavy chain has at one end a variable domain followed by a number of constant domains. Each light chain has a variable domain at one end and a constant domain at its other end. The light chain variable domain is aligned with the variable domain of the heavy chain. The light chain constant domain is aligned with the first constant domain of the heavy chain. The constant domains in the light and heavy chains are not involved directly in binding the antibody to antigen.

The variable domains of each pair of light and heavy chains form the antigen binding site. The domains on the light and heavy chains have the same general structure and each domain comprises a framework of four regions, whose sequences are relatively conserved, connected by three complementarity determining regions (CDRs). The four framework regions largely adopt a beta-sheet conformation and the CDRs form loops connecting, and in some cases forming part of the beta-sheet structure. The CDRs are held in close proximity by the framework regions and with the CDRs from the other domain, contribute to the formation of the antigen binding site, which in the case of the present invention is the formation of an anti-Ep-CAM binding site. CDRs and framework regions of antibodies may be determined by reference to Kabat et al., ("Sequences of proteins of immunological interest" US Dept. of Health and Human Services, US Government Printing Office, 1987).

The preparation of an antibody in which the CDRs are derived from a different species than the framework of the antibody's variable domains is disclosed in EP-A-0239400. The CDR's may be derived from a rodent or primate monoclonal antibody. The framework of the variable domains and the constant domains of such altered antibodies are usually derived from a human antibody. Such a humanised antibody should not elicit as great an immune response when administered to a human compared to the immune response mounted by a human against a wholly foreign antibody such as one derived from a rodent.

The antibody preferably has the structure of a natural antibody or a fragment thereof. Throughout the specification reference to antibody therefore comprises not only a complete antibody but also fragments such as a (Fab') 2 fragment, a Fab fragment, a light chain dimer or a heavy chain dimer. The antibody may be an IgG such as $IgG_1$, $IgG_2$, $IgG_3$ or $IgG_4$; or IgM, IgA, IgE or IgD or a modified variant thereof, including those that may be conjugated to other molecules such as radionuclides, enzymes, etc. Typically, the constant region is selected according to the functionality required. Normally an $IgG_1$ will demonstrate lytic ability through binding to complement and will mediate ADCC (antibody dependent cell cytotoxicity). An $IgG_4$ antibody will be preferred if a non-cytotoxic antibody is required. Antibodies according to the present invention also include bispecific antibodies such as, for example, the 17-1A antibody disclosed in Mack et al. The Journal of Immunology, 1997, 158:3965-3970. Antibodies of the present invention may be murine, chimaeric or humanised with the preferred antibody being humanised antibody.

There are four general steps to humanise a monoclonal antibody. These are:
(1) determining the nucleotide and predicted amino acid sequence of the starting antibody light and heavy variable domains;
(2) designing the humanised antibody, i.e., deciding which antibody framework region to use during the humanising process;
(3) the actual humanising methodologies/techniques; and
(4) the transfection and expression of the humanised antibody.

More specifically,
Step 1: Determining the Nucleotide and Predicted Amino Acid Sequence of the Antibody Light and Heavy Chain Variable Domains To humanise an antibody only the amino acid sequence of the antibody's heavy and light chain variable domains needs to be known. The sequence of the constant domains is irrelevant because these do not contribute to the reshaping strategy. The simplest method of determining an antibody variable domain amino acid sequence is from cloned cDNA encoding the heavy and light variable domain.

There are two general methods for cloning a given antibody's heavy and light chain variable domain cDNAs: (1) via a conventional cDNA library, or (2) via the polymerase chain reaction (PCR). Both of these methods are widely known. Given the nucleotide sequence of the cDNAs, it is a simple matter to translate this information into the predicted amino acid sequence of the antibody variable domains.

Step 2: Designing the Humanised Antibody

There are several factors to consider in deciding which human antibody sequence to use during the humanisation. The humanisation of light and heavy chains are considered independently of one another, but the reasoning is basically similar for each.

This selection process is based on the following rationale: a given antibody's antigen specificity and affinity is primarily determined by the amino acid sequence of the variable region CDRs. Variable domain framework residues have little or no direct contribution. The primary function of the framework regions is to hold the CDRs in their proper spatial orientation to recognise the antigen. Thus the substitution of rodent CDRs into a human variable domain framework is most likely to result in retention of their correct spatial orientation if the human variable domain framework is highly homologous to the rodent variable domain from which they originated. A human variable domain should preferably be chosen therefore that is highly homologous to the rodent variable domain(s).

A suitable human antibody variable domain sequence can be selected as follows:

1. Using a computer program, search all available protein (and DNA) databases for those human antibody variable domain sequences that are most homologous to the rodent antibody variable domains. The output of a suitable program is a list of sequences most homologous to the rodent antibody, the percent homology to each sequence, and an alignment of each sequence to the rodent sequence. This is done independently for both the heavy and light chain variable domain sequences. The above analyses are more easily accomplished if only human immunoglobulin sequences are included.
2. List the human antibody variable domain sequences and compare for homology. Primarily the comparison is performed on lengths of CDRs, except CDR 3 of the heavy chain which is quite variable. Human heavy chains and Kappa and Lambda light chains are divided into subgroups; Heavy chain 3 subgroups, Kappa chain 4 subgroups, Lambda chain 6 subgroups. The CDR sizes within each subgroup are similar but vary between subgroups. It is usually possible to match a rodent antibody CDR to one of the human subgroups as a first approximation of homology. Antibodies bearing CDRs of similar length are then compared for amino acid sequence homology, especially within the CDRs, but also in the surrounding framework regions. The human variable domain which is most homologous is chosen as the framework for humanisation.

Step 3: The Actual Humanising Methodologies/Techniques

An antibody may be humanised by grafting the desired CDRs onto a human framework according to EP-A-0239400. (see also P. T. Jones et al., Nature 321:522 (1986); L. Reichman et al., Nature 332:323 (1988); Verhoeyen M. et al., Science 239:1534 (1988) and J. Ellis et al., The Journal of Immunology, 155:925-937 (1995)). A DNA sequence encoding the desired reshaped antibody can therefore be made beginning with the human DNA whose CDRs it is wished to reshape. The rodent variable domain amino acid sequence containing the desired CDRs is compared to that of the chosen human antibody variable domain sequence. The residues in the human variable domain are marked that need to be changed to the corresponding residue in the rodent to make the human variable region incorporate the rodent CDRs. There may also be residues that need substituting in, adding to or deleting from the human sequence.

Oligonucleotides are synthesised that can be used to mutagenise the human variable domain framework to contain the desired residues. Those oligonucleotides can be of any convenient size. One is normally only limited in length by the capabilities of the particular synthesiser one has available. The method of oligonucleotide-directed in vitro mutagenesis is well known.

Alternatively humanisation may be achieved using the recombinant polymerase chain reaction (PCR) methodology of WO92/07075. Using this methodology, a CDR may be spliced between the framework regions of a human antibody.

In general, the technique of WO92/07075 can be performed using a template comprising two human framework regions, AB and CD and between them, the CDR which is to be replaced by a donor CDR. Primers A and B are used to amplify the framework region AB, and primers C and D used to amplify the framework region CD. However, the primers B and C each also contain, at their 5' ends, an additional sequence corresponding to all or at least part of the donor CDR sequence. Primers B and C overlap by a length sufficient to permit annealing of their 5' ends to each other under conditions which allow a PCR to be performed. Thus, the amplified regions AB and CD may undergo gene splicing by overlap extension to produce the humanised product in a single reaction.

Step 4: The Transfection and Expression of the Reshaped Antibody

Following the mutagenesis reactions to reshape the antibody, the mutagenised DNAs can be linked to an appropriate DNA encoding a light or heavy chain constant region, cloned into an expression vector, and transfected into host cells, preferably mammalian cells. These steps can be carried out in routine fashion. A reshaped antibody may therefore be prepared by a process comprising:

(a) preparing a first replicable expression vector including a suitable promoter operably linked to a DNA sequence which encodes at least a variable domain of an Ig heavy or light chain, the variable domain comprising framework regions from a human antibody and the CDRs required for the humanised antibody of the invention.
(b) preparing a second replicable expression vector including a suitable promoter operably linked to a DNA sequence which encodes at least the variable domain of a complementary Ig light or heavy chain respectively;
(c) transforming a cell line with the first or both prepared vectors; and
d) culturing said transformed cell line to produce said altered antibody.

Preferably the DNA sequence in step (a) encodes both the variable domain and the or each constant domain of the human antibody chain. The humanised antibody can be recovered and purified. The cell line which is transformed to produce the altered antibody may be Chinese Hamster Ovary (CHO) cell line or an immortalised mammalian cell line, which is advantageously of lymphoid origin, such as a myeloma, hybridoma, trioma or quadroma cell line. The cell line may also comprise a normal lymphoid cell, such as a B-cell, which has been immortalised by transformation with a virus, such as the Epstein-Barr virus. Most preferably, the immortalised cell line is a myeloma cell line or a derivative thereof. The expression system of choice is the glutamine synthetase expression system described in WO87/00462 (see also, P. E. Stephens et al., Nucleic Acid Res. 17:7110 (1989) and C. R. Bebbington et al., Bio/Technology 10:169 (1992)).

Although the cell line used to produce the humanised antibody is preferably a mammalian cell line, any other suitable cell line, such as a bacterial cell line or a yeast cell line, may alternatively be used. For single antibody chains, it is envisaged that *E. coli*-derived bacterial strains could be used. The antibody obtained is checked for functionality. If functionality is lost, it is necessary to return to step (2) and alter the framework of the antibody.

Once expressed, the whole antibodies, their dimers, individual light and heavy chains, or other immunoglobulin forms of the present invention can be purified according to standard procedures of the art, including ammonium sulfate precipitation, affinity columns, column chromatography, gel electrophoresis and the like (see generally, Scopes, R., Protein Purification, Springer-Verlag, N.Y. (1982)). Substantially pure immunoglobulins of at least about 90 to 95% homogeneity are preferred and 98 to 99% or more homogeneity most preferred, for pharmaceutical uses. Once purified, partially or to homogeneity as desired, an antibody may then be used therapeutically.

Antibodies are typically provided as a pharmaceutical composition comprising a pharmaceutically acceptable carrier or diluent and, as active ingredient, an antibody according to the invention. The antibody and pharmaceutical compositions thereof are particularly useful for parenteral administration i.e., subcutaneously, intramuscularly or intravenously.

The compositions for parenteral administration will commonly comprise a solution of the antibody or a cocktail thereof dissolved in an acceptable carrier, preferably an aqueous carrier. A variety of aqueous carriers can be used, e.g., sterile water for injection, 0.9% sodium chloride in water, 5% dextrose in water and Lactated Ringers solution. These solutions are sterile and generally free of particulate matter. These compositions may be sterilised by conventional, well known sterilisation techniques. The compositions may contain pharmaceutically acceptable auxiliary substances as required to approximate physiological conditions such as pH adjusting and buffering agents, toxicity adjustment agents and the like, for example sodium acetate, sodium chloride, potassium chloride, calcium chloride, sodium lactate, etc. The concentration of antibody in these formulations can vary widely, for example from less than about 0.5%, usually at or at least about 1% to as much as 15 or 20% by weight and will be selected primarily based on fluid volumes, viscosities, etc. in accordance with particular mode of administration selected.

Thus, a typical pharmaceutical composition for intramuscular injection could be made to contain 1 ml sterile buffered water, and 50 mg of antibody. A typical composition for intravenous infusion could be made up to contain 250 ml of sterile Ringers solution and 150 mg of antibody. Actual methods for preparing parenterally administrable compositions will be known or apparent to those skilled in the art, particularly, those trained in the preparation of parenteral products and are described in more detail in, for example, *Remmington's Pharmaceutical Science*, 15th Ed., Mack Publishing Company, Easton, Pa. (1990).

The antibodies of this invention can be lyophilised for storage and reconstituted in a suitable carrier prior to use. This technique has been shown to be effective with conventional immunoglobulins. Any suitable lyophilisation and reconstitution techniques can be employed. It will be appreciated by those skilled in the art that lyophilization and reconstitution can lead to varying degrees of antibody activity loss (e.g., with conventional immune globulins, IgM antibodies tend to have greater activity loss than IgG antibodies) and that use levels may have to be adjusted to compensate.

The dosage range of the antibody in accordance with the invention is about 0.5 to 1000 mg/m$^2$, preferably about 0.5 to 250 mg/m$^2$, more preferably, between 0.5 and 100 mg/m$^2$ and 0.5 and 50 mg/m$^2$ and most preferably between 5 and 25 mg/m$^2$ such as for example, 15 mg/m$^2$.

Similarly, expressed in mg per dose, the dosages of the antibody may be about 1 to 2000 mg per dose, preferably about 1 to 500 mg per dose, more preferably between 1 to 200 mg per dose and between 1 to 100 mg per dose and most preferably between 10 and 50 mg per dose such as, for example 30 mg per dose.

Single or multiple administrations of the compositions can be carried out with dose levels and pattern being selected by the treating physician. In any event, the pharmaceutical formulations should provide a quantity of the antibody(ies) sufficient to effectively treat the patient.

Typically, the chemotherapeutic agent and antibody will be presented as separate pharmaceutical compositions for co-administration, but they may also be formulated as a single pharmaceutical formulation. In this way both the antibody and the chemotherapeutic agent are presented to the patient within one and the same composition.

One or more distinct chemotherapeutic agents and one or more distinct anti-Ep-CAM antibodies may be co-administered in all aspects of the present invention. Thus reference to a chemotherapeutic agent comprises one or more distinct chemotherapeutic agent(s). If there is more than one chemotherapeutic agent, these may be administered either individually each on its own and/or together as a chemotherapeutic agent cocktail. Similarly, reference to antibody comprises one or more distinct anti-Ep-CAM antibody(ies). If there is more than one antibody, these may again be administered either individually each on its own and/or together as a cocktail. Additionally, the chemotherapeutic agent(s) are typically administered separately from the antibody(ies) but they may also be administered together as a chemotherapeutic agent(s)/antibody(ies) cocktail.

Co-administration of the chemotherapeutic agent/radiotherapy with the antibody comprehends administration substantially simultaneously of both the chemotherapeutic agent/radiotherapy and the antibody. Essentially, the rational behind co-administration is to allow sufficient exposure of Ep-CAM expressing tumour cells to a chemotherapeutic agent/radiotherapy known to block cell cycle progression at G$_2$/M to achieve the desired increase in Ep-CAM antigen density prior to exposure of the same tumour cells to an anti-Ep-CAM antibody thereby achieving greater targeting of anti-Ep-CAM antibodies to Ep-CAM expressing tumours. Co-administration therefore comprises any mode of administering a chemotherapeutic agent/radiotherapy in conjunction with an anti-Ep-CAM antibody that will achieve this result.

Throughout the specification the term "combination of an anti-Ep-CAM antibody with a chemotherapeutic agent" refers to one wherein the chemotherapeutic agent/radiotherapy and the anti-Ep-CAM antibody have been co-administered.

Preferably the chemotherapeutic agent is administered simultaneously with the antibody or more preferably before the antibody. Thus the chemotherapeutic agent may be administered on the same day as the antibody, either together or within hours of each other but may also be administered up to about two months beforehand, typically, about one or two weeks beforehand and more typically less than a week beforehand, say one to three days beforehand.

Additionally, co-administration also includes administering more than one dose of antibody within several weeks after one or more doses of chemotherapeutic agent, in other words the chemotherapeutic agent need not be re-administered again with every subsequent administration of the antibody, but may be administered just once or intermittently during the course of antibody treatment. Co-administration also comprises administration of the chemotherapeutic agent up to 3 weeks after the antibody, preferably within a week and more preferably within a few days such as one to five days.

The antibody may be administered several times daily. Similarly the chemotherapeutic agent may be infused continuously over several hours or even days.

The present invention also provides a method of treating mammalian patients, preferably humans, afflicted with cancer which comprises co-administering a chemotherapeutic agent which is capable of arresting Ep-CAM antigen expressing cells in $G_2/M$ in combination with an anti-Ep-CAM antibody. Preferably, the chemotherapeutic agent is given simultaneously and more preferably prior to administration of the antibody.

The cancers which may be treated particularly effectively with this combination therapy are primary or metastatic cancers of any histologic or histogenetic origin that express the Ep-CAM antigen. This includes, for example, prostate cancers, lung cancers, breast cancers, colon cancers, pancreatic cancers and ovarian cancers.

Dosing schedules for the treatment method of the present invention can be adjusted to account for the patient characteristics, disease state, characteristics of the chemotherapeutic agent and characteristics of the anti-Ep-CAM antibody. The goal of dosing schedules under this invention will be to administer anti-Ep-CAM antibody in a manner that will expose the Ep-CAM expressing tumour cells to the anti-Ep-CAM antibody at a time when antigen expression is likely to be increased due to exposure to chemotherapy which is known to block cell cycle progression at $G_2/M$. Additionally, as much as possible a dosing schedule convenient for the patient must be maintained.

Preferred dosing schedules for administration of the anti-Ep-CAM antibody and chemotherapy include: administering the anti-Ep-CAM antibody once every one or two weeks, preferably once every three or four weeks or a combination thereof for as long as necessary. The chemotherapeutic agent is given according to the established regimen for that agent or a regimen which will allow exposure of Ep-CAM expressing tumour cells to be arrested in $G_2/M$. Preferred dosing schedules vary with the chemotherapy agent and disease state but include, for example, once weekly, once every three or four weeks, or daily for several (e.g., 3-5) days repeated every three or four weeks for as long as necessary. Dosing of the anti-Ep-CAM antibody may take place on the same day or different days as indicated for the chemotherapeutic agent. Adjustment of the dosing schedule or strength of dose to prevent or decrease toxicity or side effects may take place with either the anti-Ep-CAM antibody or the chemotherapy agent.

For example, the preferred dosing schedule for co-administration of vinorelbine and cisplatin in combination with humanised 323/A3 ($IgG_1$) is administration of humanised 323/A3 ($IgG_1$) at a dose of 30 mg/m$^2$ once a week for as long as necessary but typically for a period of 3 to 4 weeks, followed by a 30 mg/m$^2$ dose every other week thereafter for as long as necessary. Vinorelbine is administered at a dose 25 mg/m$^2$ on day 1, 8, 15 and 22. Cisplatin is given only once at a dose of 100 mg/m$^2$ on day 1. Thereafter the vinorelbine/cisplatin regime is repeated every 28 days for as long as necessary. Preferably, vinorelbine, cisplatin and humanised 323/A3 ($IgG_1$) are administered at the same time on day one over a period of about 2 to 3 hours.

Another example of a preferred dosing schedule is the administration of paclitaxel/carboplatin in combination with humanised 323/A3 ($IgG_1$), wherein 323/A3 ($IgG_1$) is administered as for the vinorelbine/cisplatin example above and paclitaxel and carboplatin are given at a dose of 225 mg/m$^2$ and AUC=6.0 respectively, on day 1, with a repeat dosage every 28 days thereafter for as long as necessary. Again, paclitaxel, carboplatin and humanised 323/A3 ($IgG_1$) are preferably administered together on day 1 over a period of about 2 to 3 hours.

Other preferred dosage schedules which comprise the combination of 323/A3 ($IgG_1$) with any of NAVELBINE®, cisplatin or TAXOL® on their own would comprise similar dosages and administration schedules, using just one anticancer agent instead of two.

When the preferred anti-Ep-CAM antibody is PANOREX®, the dosage of antibody is between 10 to 500 mg per dose, preferably 100 mg per dose.

A further aspect of the present invention is a method of increasing antibody binding of anti-Ep-CAM antibodies to Ep-CAM expressing cells by co-administering to a patient a chemotherapeutic agent capable of arresting cells in $G_2/M$ together with said anti-Ep-CAM antibody.

By co-administering a chemotherapeutic agent according to the present invention together with an Ep-CAM antibody, it is possible to increase antibody binding by about 2 to 10 fold, preferably by more than 4 fold, more preferably by more than 6 fold and most preferably by more than 8 fold.

FIGURES

FIG. 1.

Ep-CAM is expressed across the cell cycle, but at higher density and greater homogeneity on cells in S (dotted line) and in $G_2/M$ (dashed line) phases than in $G_0/G_1$ cells (solid line). This pattern of expression has been documented in a number of other human colon, prostate, and lung tumour cell lines.

FIG. 2.

Cell cycle arrest is a prominent feature of adenocarcinoma cells exposed in vitro to NAVELBINE® (NVB; 30 nM) plus Cisplatin (CDDP; 5 or TAXOL® (TAX; 80 nM) plus Carboplatin (CPBDA; 100 µM), compared to media alone, 5-Fluorouracil (5FU), interferon-alpha (IFN-alpha; 100 U/ml), or interferon-gamma (IFN-gamma; 100 U/ml). The area of each bar is divided to indicate the percentage of cells in $G_0/G_1$ and in $S+G_2/M$ phases; the height of each bar indicates the average number of Ep-CAM molecules per cell within the population. Cells in S phase and in $G_2/M$ phase express higher levels of Ep-CAM (FIG. 1), and the agents which blocked cell cycle progression had overall increased Ep-CAM expression.

FIG. 3.

The expression of Ep-CAM antigen was quantified on a variety of adenocarcinoma cell lines as well as primary cultures of normal human cells. Cultured cells were exposed sequentially to media, or to 30 nM NAVELBINE® followed by 5 µM Cisplatin (NVB+CDDP), or to 80 nM TAXOL® followed by 100 µM Carboplatin (TAX+CPBDA). The 4 adenocarcinoma cells expressed higher antigen levels subsequent to exposure to cycle-specific drug combinations, whereas the 4 normal cells did not show any increase in antigen expression, which remained undetectable in 2 of the normal cell populations.

FIG. 3a.

The binding of PANOREX®, a related murine monoclonal antibody with specificity for the Ep-CAM antigen, was evaluated after a 15 minute incubation with HT29 adenocarcinoma cells which had been cultured with NAVELBINE® plus Cisplatin or with TAXOL® as previously described. A significant increase (34%) in antibody binding was seen on the cells treated with NAVELBINE® plus Cisplatin; 82% of these cells were arrested in S or $G_2$/M cycle phase compared to 21% of the control cells. (A smaller increase (8%) in antibody binding was seen for cells treated with TAXOL®, but in this experiment only 57% of the cells were cycle-arrested) as is shown in FIG. 3a.

FIG. 4.

The ability of human peripheral blood ADCC effector cells to lyse tumour target cells incubated with humanized 323/A3 (IgG) (a humanized monoclonal antibody having specificity for the Ep-CAM antigen and capable of interacting with Fc receptors on human effector cells) in vitro was improved when the target cells had been pre-treated with NAVELBINE® (30 nM) plus cisplatin (5 µM).

FIG. 5.

Treatment of human tumour xenograft-bearing mice with a cell-cycle-specific cytotoxic agent promoted improved localization of antibody specific for Ep-CAM to the tumours.

FIG. 6.

Humanised 323/A3 (IgG$_1$) kappa light chain amino acid sequence SEQ ID NO:11.

FIG. 7.

Humanised 323/A3 (IgG$_1$) heavy chain amino acid sequence SEQ ID NO:12.

FIG. 8.

Vector map of pEE6.

FIG. 9.

Vector map of pEE12.

FIG. 10.

Vector map of pEE18.

FIG. 11.

Humanised 323/A3 (IgG$_{4cys}$) kappa light chain amino acid sequence SEQ ID NO: 13.

FIG. 12.

Humanised 323/A3 (IgG$_{4cys}$) variant heavy chain amino acid sequence SEQ ID NO: 14.

FIG. 13.

Humanised 323/A3 (IgG$_{2cys}$) kappa light chain amino acid sequence SEQ ID NO: 15.

FIG. 14.

Humanised 323/A3 (IgG$_{2\ cys}$) heavy chain amino acid sequence SEQ ID NO:16.

FIG. 15.

Humanised 323/A3 (IgG$_1$) light chain cDNA sequence (also 323/A3 (IgG4cys and IgG$_{2cys}$ light chain cDNA sequence) and corresponding amino acid sequence, SEQ ID NO:1, SEQ ID NO:2 and SEQ ID NO:3.

FIG. 16.

Humanised 323/A3 (IgG$_1$) heavy chain cDNA sequence and corresponding amino acid sequence, SEQ ID NO:4 and SEQ ID NO:5.

FIG. 17.

Humanised 323/A3 (IgG$_4$) heavy chain cDNA sequence and corresponding amino acid sequence, SEQ ID NO:6 and SEQ ID NO:7.

FIG. 18.

Humanised 323/A3 (IgG$_{2cys}$) heavy chain cDNA sequence and corresponding amino acid sequence SEQ ID NO:8, SEQ ID NO: 9 and SEQ ID NO:10.

The following examples illustrate the invention.

EXAMPLE 1

Ep-CAM Antigen Expression Varied by Phase Across the Cell Cycle on PC-3 Prostatic Adenocarcinoma Cells Populations of PC-3 prostatic adenocarcinoma cells were evaluated for distribution in $G_0/G_1$, S, and $G_2$/M phases of the cell cycle as well as Ep-CAM expression. Cells were gently trypsinized and mechanically detached from the culture flasks and resuspended in calcium and magnesium-free phosphate-buffered saline containing bovine serum albumin and NaN$_3$. Exactly 2×10$^5$ cells were stained with FITC-323/A3 murine IgG antibody or FITC-murine IgG (control). Cells were fixed with cold paraformaldehyde, then permeabilized for DNA staining with Tween-20. Cellular DNA was stained with propidium iodide and RNase A. Listmode data were acquired on a FACScan flow cytometer (Becton Dickinson Immunocytometry Systems) equipped with a 488 nm laser using Cell Fit software. Cell cycle analysis was done using SOBR modelling (where possible, otherwise manual estimations were employed) on Cell Fit. Ep-CAM antigen expression as detected by 323/A3 binding was evaluated separately using histogram analysis in WINLIST™ (Verity Software House).

FIG. 1 shows that Ep-CAM is expressed across the cell cycle, but at higher density and greater homogeneity on cells in S (dotted line) and in $G_2$/M (dashed line) phases than in $G_0/G_1$ cells (solid line). This pattern of expression has been documented in a number of other human colon, prostate, and lung tumor cell lines.

EXAMPLE 2

Figure 2:
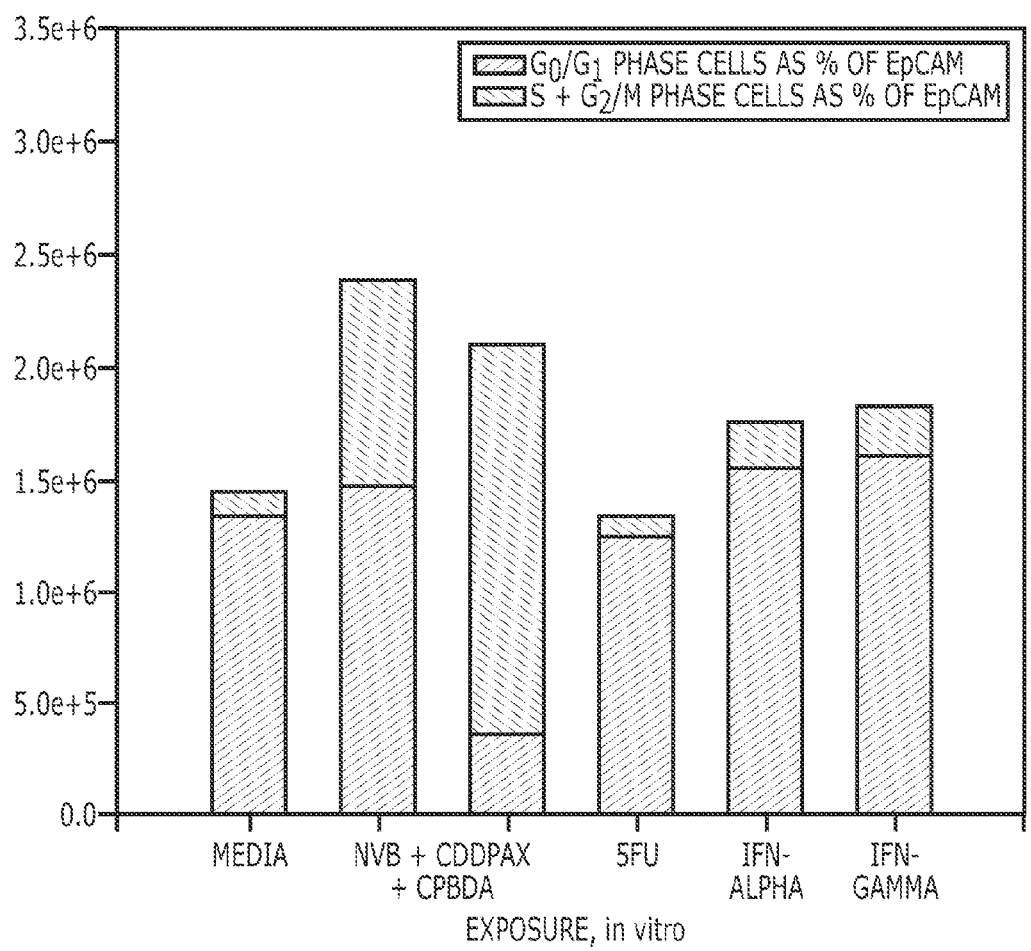

Increased Expression of Ep-CAM Antigen on Adenocarcinoma Cells was Associated with Arrest of Cell Cycle Progression and Accumulation of Cells in S and $G_2$/M Phases Adenocarcinoma cell lines were exposed to the various drugs or combinations of drugs as indicated in FIG. 2. Subconfluent cells were exposed to NAVELBINE® or TAXOL® for up to 24 hours, then washed and exposed to cisplatin or carboplatin, respectively, overnight. Cells were exposed to 5FU for 24 hours, and for 2-5 days to the interferons. Cells were washed and cultured for another 2-5 days prior to analysis for antigen expression and cell cycle status as described in Example 1. Antigen expression was quantified by comparison of the binding of fluorescein-conjugated 323/A3 to cultured cells with binding to calibrated microbead standards.

Cell cycle analysis demonstrated that only 6.3% of the media control cells were in S and $G_2$/M phases combined, compared to 39.4% of NVB+CDDP and 82.6% of TAX+CPBDA cells, both combinations of which caused significant increases in Ep-CAM antigen expression (as demonstrated in FIG. 2). Antigen expression was not significantly increased in cells exposed to 5FU, IFN-α, or IFN-γ, which had only 7.9%, 12%, and 11.5%, respectively, of cells in S+$G_2$/M phase. Thus, only the drugs which caused accumulation of cells in S or $G_2$/M phases were able to cause a significant increase in Ep-CAM antigen expression.

EXAMPLE 2a

The binding of PANOREX®, a related murine monoclonal antibody with specificity for the Ep-CAM antigen, was evaluated after a 15 minute incubation with HT29 adenocarcinoma cells which had been cultured with NAVELBINE® plus Cisplatin or with TAXOL® as previously described. A significant increase (34%) in antibody binding was seen on the cells treated with NAVELBINE® plus Cisplatin; 82% of these cells were arrested in S or $G_2$/M cycle phase compared to 21% of the control cells. (A smaller increase (8%) in antibody binding was seen for cells treated with TAXOL®, but in this experiment only 57% of the cells were cycle-arrested) as is shown in FIG. 3a.

EXAMPLE 3

Increased Ep-CAM Antigen Expression was Observed on Tumour Cells but not Normal Cells Exposed to Cytotoxic Drugs In Vitro The expression of Ep-CAM antigen was quantified on a variety of adenocarcinoma cell lines as well as primary cultures of normal human cells. Cultured subconfluent cells were exposed sequentially to media, or to 30 nM NAVELBINE® followed by 5 µM cisplatin (NVB+CDDP), or to 80 nM TAXOL® followed by 100 µM carboplatin (TAX+CPBDA). Cells were washed with media and cultured for another 2-5 days prior to analysis for antigen expression as described in Examples 1 and 2.

Figure 3:
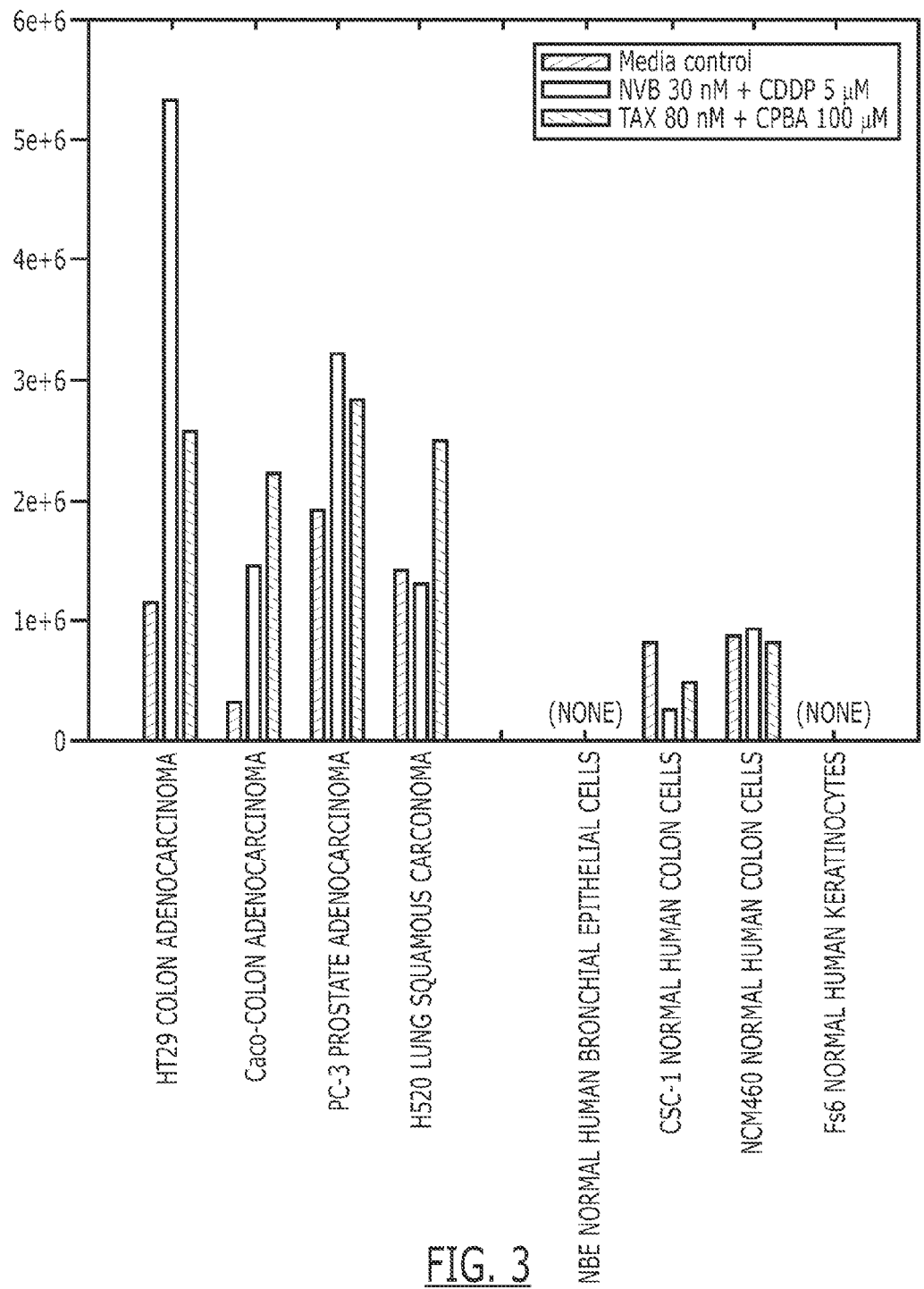
Figure 3A:
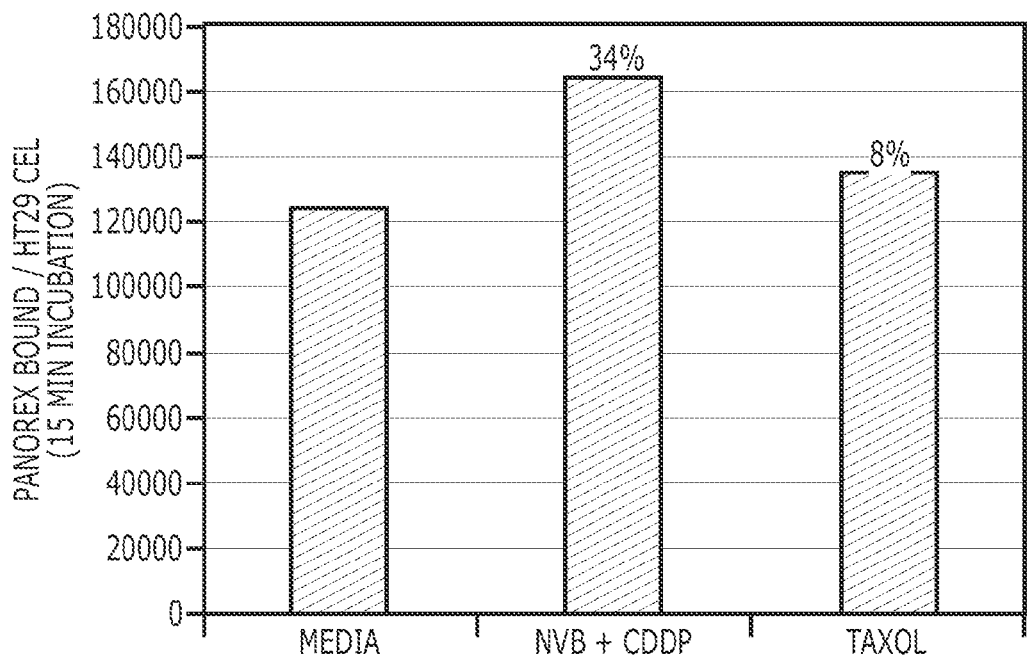

FIG. 3 clearly shows that the adenocarcinoma cells expressed higher antigen levels subsequent to exposure to cycle-specific drug combinations, whereas the normal cells did not show any increase in antigen expression, which remained undetectable in 2 of the normal cell populations.

EXAMPLE 4

Cells Exposed to NAVELBINE® Plus Cisplatin were Better Targets for Human ADCC Activity than Control Cells Adenocarcinoma cells were exposed to drugs as described in Examples 1 and 2 above, and then harvested and seeded into 96-well plates for use as target cells in a $^{51}$Cr-release cytotoxicity assay. Target cells were cultured overnight with $^{51}$Cr, and then washed. Human peripheral blood mononuclear cells which had been allowed to adhere overnight were added at a 50:1 effector:target ratio, and the ADCC cultures were incubated for 6 hours. Supernatants were collected and counted for radioactivity, and the percentage specific release was calculated. (see FIG. 4).

Figure 4:
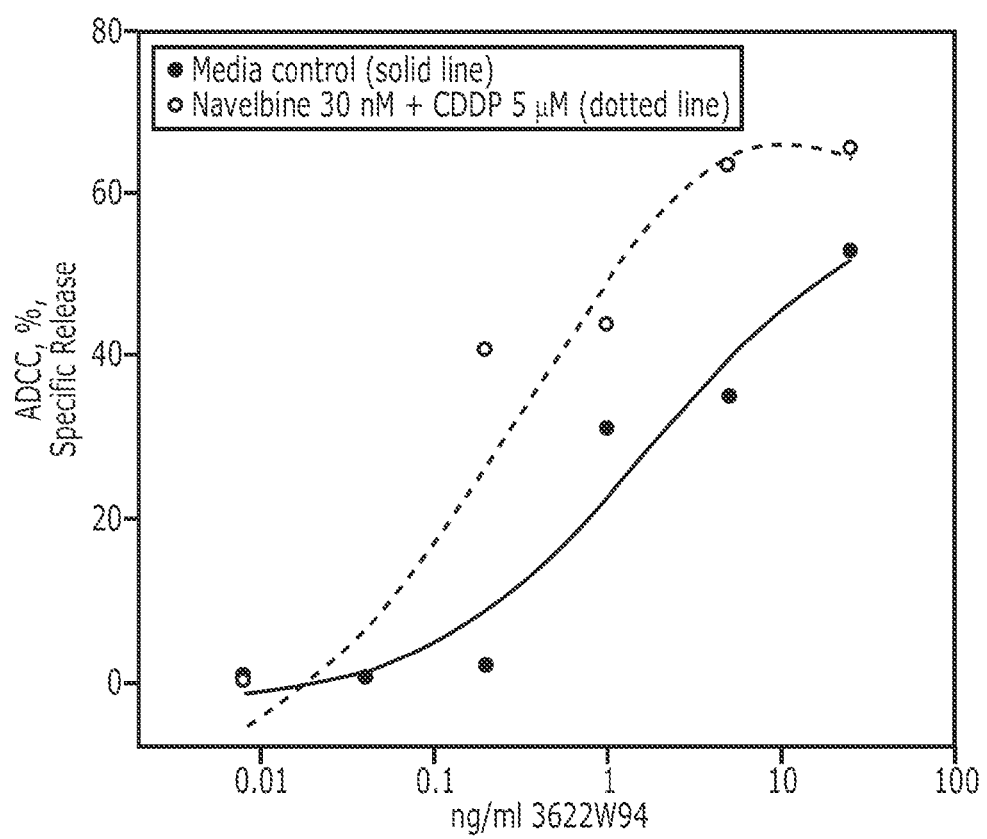

FIG. 4 clearly shows that PC-3 prostatic adenocarcinoma cells are better targets for human ADCC activity after exposure to NAVELBINE®/cisplatin compared to controls which have not been exposed to these chemotherapeutic agents. This effect may be due directly to increased antigen expression and thereby increased antibody binding, decreased modulation of the Ep-CAM antigen, increased fragility of the target cells, or a combination of the above.

EXAMPLE 5

Antibody Targeting to Ep-CAM-Positive Tumours was Significantly Improved by Pre-Treatment of the Mice with NAVELBINE®

Human colon adenocarcinoma (HT-29) tumours were initiated by subcutaneous implantation into female CD-1 nude mice (Charles River). When the tumours reached 200-300 mg, animals were divided into groups of five. NAVELBINE® was injected intravenously at a dosage of 28 mg/kg on days 1 and 5. A control group was dosed with 5-fluorouracil (5-FU) intraperitoneally at 20 mg/kg on days 1 and 5. On day 6, humanised 323/A3 $IgG_{4Cys-TMT}$ (a humanized monoclonal antibody chelator conjugate with specificity for the Ep-CAM antigen) was labelled with lutetium-177 and injected intravenously via the lateral tail vein. Each mouse received 4.1 protein/2.09 µCi lutetium-177/0.2 ml injection. Blood, spleen, liver, lung, kidney, femur and tumour were harvested on days 1, 3 and 5 post-antibody for direct gamma counting (see FIG. 5 for results).

Figure 5:
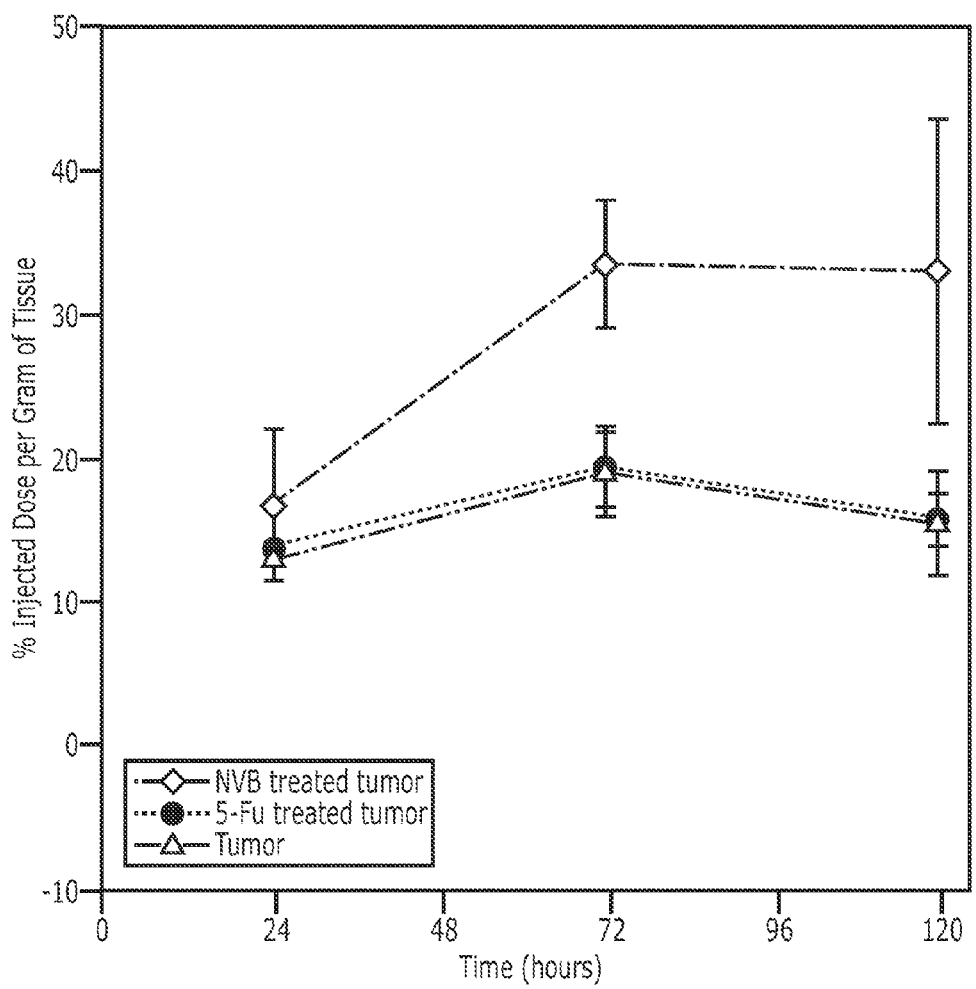

FIG. 5 shows that pre-treatment with NAVELBINE® increases antibody targeting to Ep-CAM positive tumours whilst pre-treatment with 5-FU does not.

EXAMPLE 6

Expression of the Humanized Antibody 323/A3 ($IgG_1$) Variant in NSO Cells

1. Purpose/Summary

Figure 10:
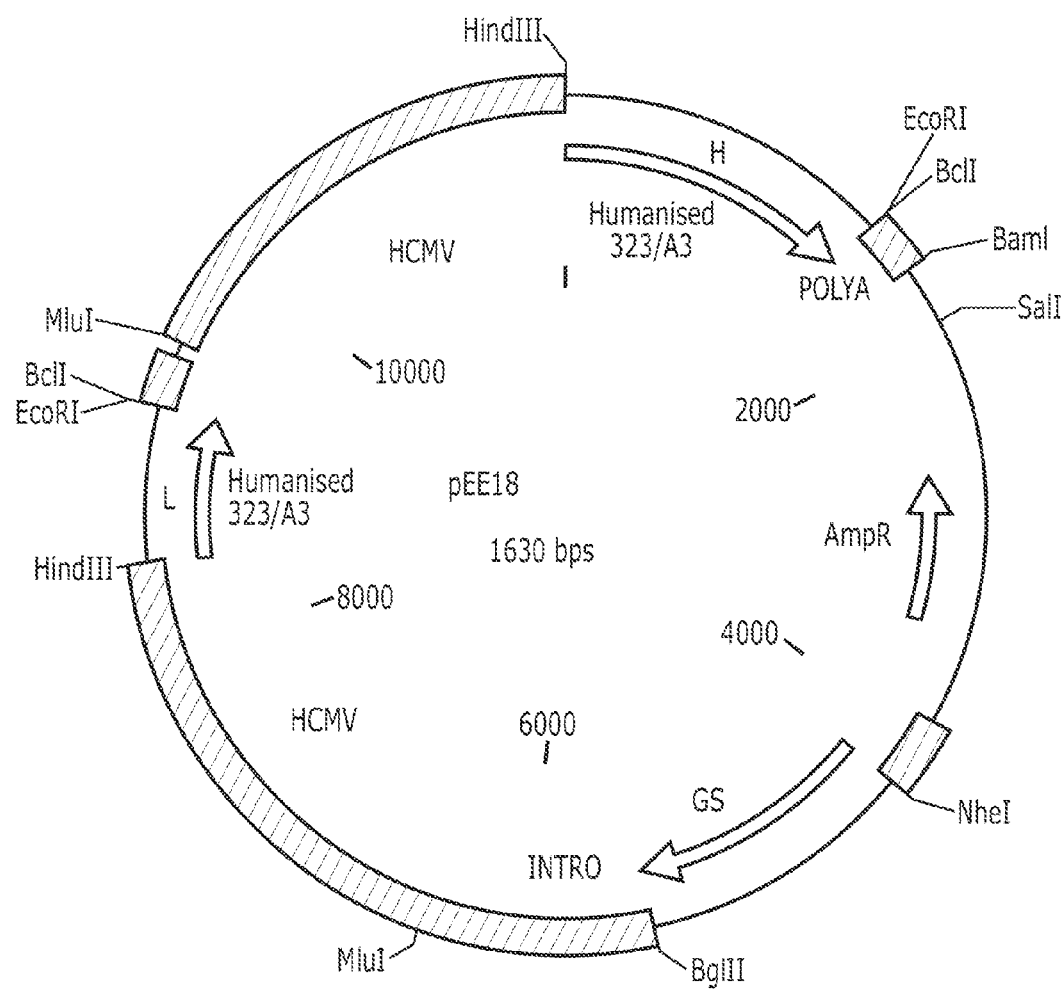

The cDNAs encoding the humanized 323/A3 antibody light and heavy chains (see FIGS. 15 and 16 respectively) were genetically engineered into a single Celltech glutamine synthetase (GS) expression plasmid, pEE18 (see FIG. 10), and used to transfect murine NSO cells.

2. Materials and Methods 2.1 Materials

Figure 8:
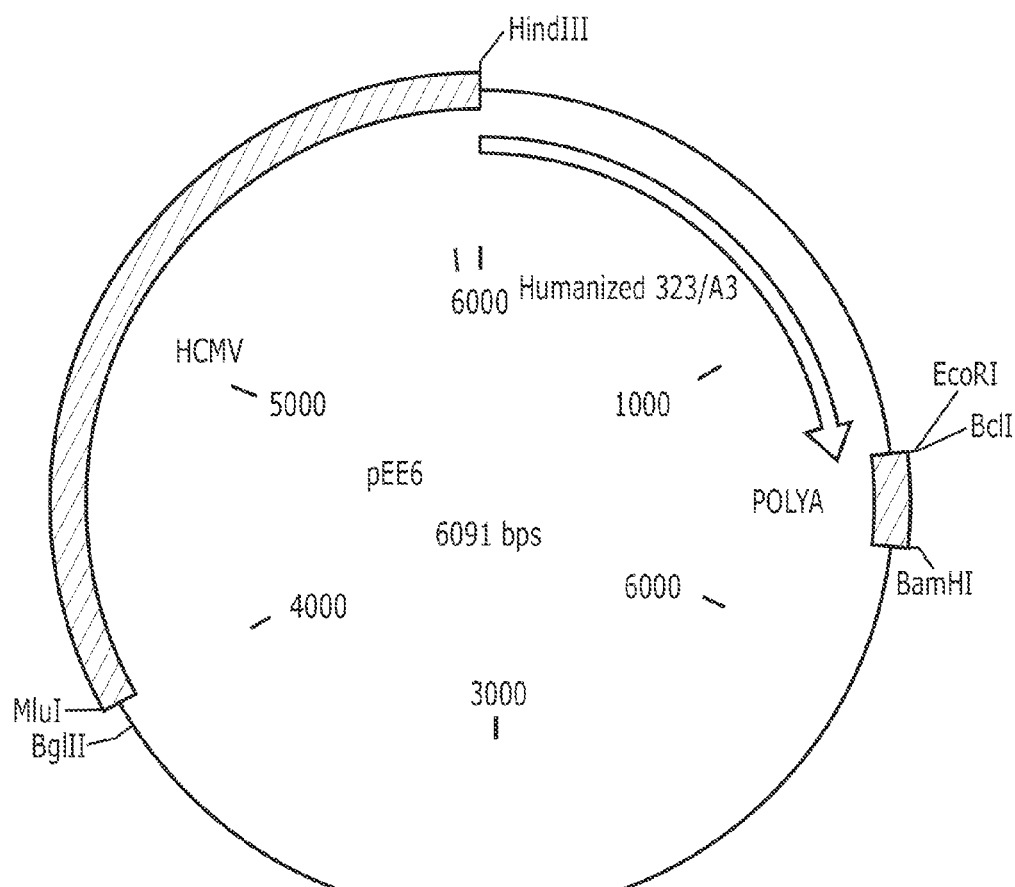
Figure 9:
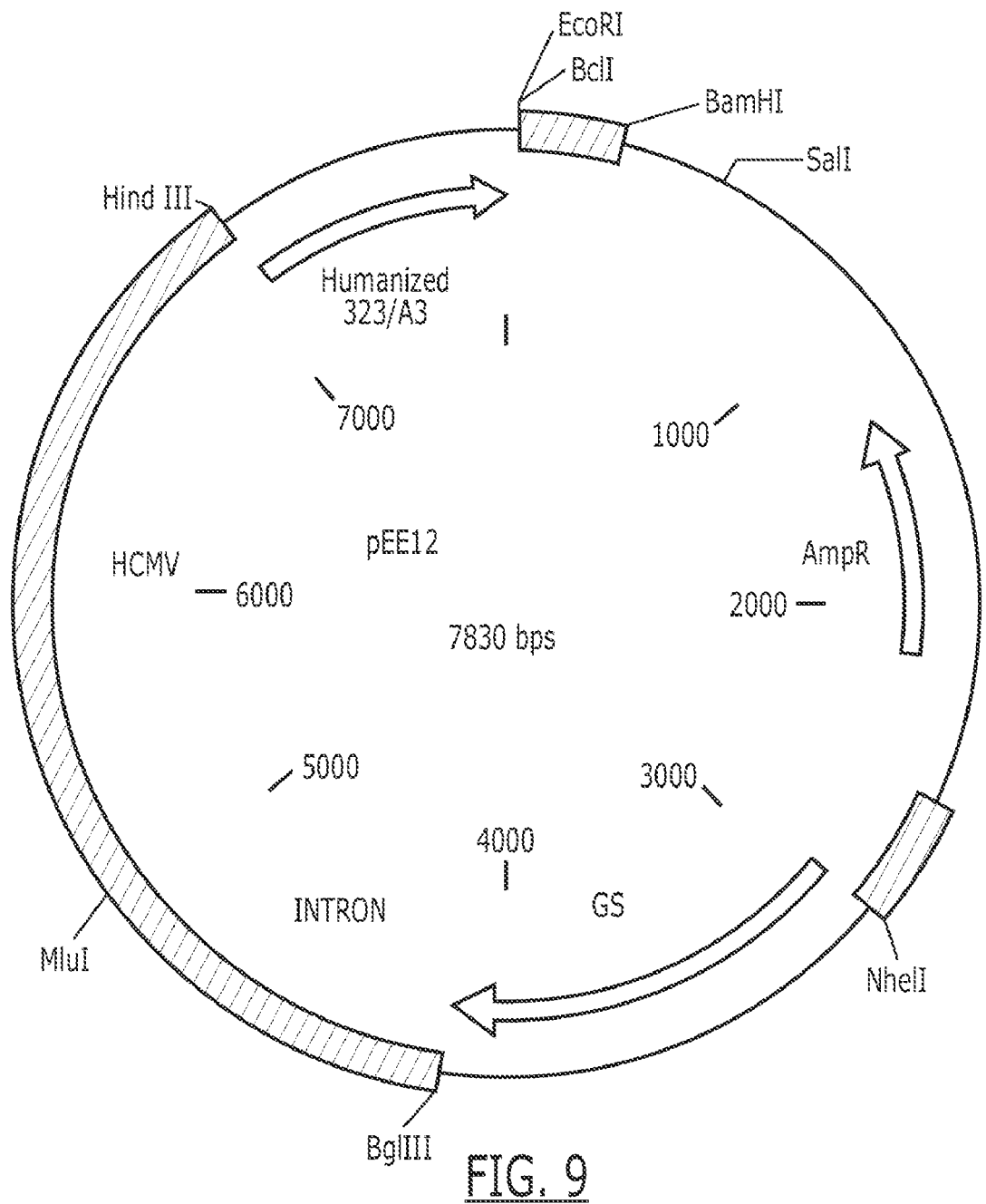

NSO cells were obtained from Celltech Biologics plc, Slough, SL1 4EN, Berkshire, UK. The expression plasmids pEE6HCMV and pEE12 (see FIGS. 8 and 9) were obtained from Celltech Biologics plc, Slough.

2.2 The pEE6hmcv plasmid (see FIG. 8) encoding full length humanised heavy chain DNA was digested with Bam HI and Bgl II to liberate the 3.2 kb fragment that contained the DNA encoding the heavy chain under the transcriptional control of the major immediate early promoter of the human cytomegalovirus. This fragment was cloned into the Bam HI site of pEE12 (FIG. 9) that contained the DNA encoding the humanised light chain. See FIG. 6 for humanised 323/A3 ($IgG_1$) kappa light chain amino acid sequence and FIG. 7 for the humanised 323/A3($IgG_1$) Heavy chain amino acid sequence. See FIG. 10 for schematic representation of the pEE18 plasmid encoding 323/A3 ($IgG_1$) heavy and light chains.

2.2.2 Transfection and Selection of NSO Cells 2.2.2.1 Tissue Culture

All single cell culture activities were performed in isolated rooms that contained a single laminar flow hood and single incubator dedicated solely to the use of NSO cells in the production of stable cell lines secreting humanised 323/A3($IgG_1$). No other NSO cells lines, human cell lines or virus transformed cell lines were used within this environment.

A vial of NSO cells was revived and grown in 1:1:1 medium composed of DMEM:RPMI-1640:Sigma PFHM (1:1:1) to a cell density between 0.5 and $1\times10^6$ mL. For electroporation, the cells were harvested by centrifugation and washed once with PBS. pEE18 plasmid DNA encoding 323/A3 ($IgG_1$) was digested with Sal I, heat inactivated at 65° C. for 15 minutes, precipitated with ethanol and air-dried. The dried DNA pellet was resuspended in PBS to a concentration of 0.5 µg/mL and 100 µL aliquoted into a 2 mm electroporation cuvette (BTX). Washed NSO cells were resuspended at $1.2\times10^7$/ml and 400 µL added to the cuvette to give a final density of $10^6$ mL in a final volume of 0.5 mL. Electroporation was at 300 V for 1 msec in a BTX 8209 GenePulser followed by incubation on ice for 5-10 minutes. The electroporation mixture was resuspended at $10^5$ cells/mL with 1:1:1 medium and distributed over 96-well plates at 50 μL/well. The following day, wells were fed with 150 μL GS medium (Gln-free IMDM, 1=X GS and nucleoside supplement, 5% DFBS) to begin the GS selection process such that all wells had a final concentration of 3% DFBS.

2.2.2.2 Specific Production Rate (SPR)

Selected cell lines grown in GS media (3% DFBS) were seeded at a density of $0.2 \times 10^6$ cells/mL in T-25 flasks (Costar) that contained 5 mL of GS media (3% DFBS). Cells were incubated overnight at 37° C. for 24 hours after which an aliquot of each culture supernatant was removed. The supernatants were used in the human IgG ELISA assay to determine the concentration of secreted humanised 323/A3(IgG$_1$). The SPR value was derived by multiplying the concentration of 323/A3 (IgG) antibody in the supernatant times the volume (5.0) and is expressed as μg/$10^6$ cells/24 hours.

2.2.2.3 Cryopreservation of Cells

Selected cell lines were routinely harvested when cell density was greater than $0.2 \times 10^6$ cells/mL. An appropriate volume of cells was removed and subjected to centrifugation at 1,000×g for 5 minutes at 22° C. The cell pellet was gently resuspended to 1-4×$10^6$ cells/mL with ice-cold freezing media consisting of 20% (v/v) FBS/10% (v/v) DMSO/GS Media (sterile filtered). Each 1.0 mL of the cell suspension was aliquoted into a 1.8 ml cryopreservation vial (NUNC) and gradually frozen overnight in a Cryo 1° C. Freezing Container (Nalgene) that had been placed in a −70° C. freezer. The vials were then removed from the container and stored in the vapour phase of a liquid nitrogen freezer.

Twenty vials of each cell line, including a low humanised 323/A3(IgG$_1$) producer were frozen down as described above and stored initially in the vapour phase of an MVE Cryogenics XLC440 liquid nitrogen freezer. The cells were subsequently transferred and stored in the vapour phase of an MVE Cryogenics XLC500 liquid nitrogen freezer.

EXAMPLE 7

Expression of the Humanized Antibody 323/A3(IgG$_{4cys}$) in NSO Cells

1. Purpose Summary

The cDNAs encoding the humanized antibody 323/A3 (IgG$_{4cys}$) (a humanised 323/A3 antibody) antibody light and heavy chains (see FIGS. 15 and 17 were genetically engineered into a single Celltech glutamine synthetase (GS) expression plasmid, pEE18, and used to transfect murine NSO cells.

2. Materials and Methods 2.1 Materials (as for Example 6 above)

2.2 Creation of humanised 323/A3 (IgG$_{4cys}$ pEE18 expression plasmid

The pEE6HMCV plasmid (see FIG. 8) encoding full length humanized heavy chain DNA was digested with Bam HI and Bgl II to liberate a 3.2 kb fragment that contained the DNA encoding the heavy chain under the transcriptional control of the major immediate early promoter of the human cytomeglovirus. This fragment was cloned into the Bam HI site of pEE12 that contained the DNA encoding the humanized light chain. See FIG. 11 for humanised 323/A3(IgG$_4$) kappa light chain amino acid sequence and FIG. 12 for the 323/A3 IgG$_{4cys}$ variant heavy chain amino acid sequence. See FIG. 10 for schematic representation of the pEE18 plasmid encoding 323/A3 heavy and light chains.

2.2.2 Transfection and Selection of NSO Cells: see Example 6 above.

EXAMPLE 8

Expression of the Humanized Antibody 323/A3(IgG$_{2cys}$) in NSO Cells

1. Purpose/Summary

The cDNAs encoding the humanized 323/A3(IgG$_{2cys}$) antibody heavy and light chains were genetically engineered into a single Celltech glutamine synthethase (GS) expression plamid, pEE18, and used to transfect murine NSO cells.

2. Materials and Methods 2.1 Materials as for Examples 6 and 7 above 2.2 Creation of 323/A3 (IgG$_{2cys}$) pEE18 Expression for Plasmid The pEEE6 hcmv plasmid encoding full length humanized heavy chain DNA was digested with Bam HI and Bgl II to liberate a 3.2 kb fragment that contained the DNA encoding the heavy chain under the transcriptional control of the major immediate early promoter of the human cytomegalovirus. This fragment was cloned into the Bam II site of pEE12 that contained the DNA encoding the humanized light chain. See FIG. 13 for 323/A3 (IgG$_{2cys}$) Kappa Light Chain Amino Acid Sequence and FIG. 14 for the 323/A3(IgG$_{ays}$) Heavy Chain Amino Acid Sequence. See FIG. 10 for schematic representation of the pEE18 plasmid encoding 323/A3 (IgG$_{2cys}$) heavy and light chains.

2.2.2 Transfection and Selection of NSO Cells—See Examples 6 and 7 above.

---

The invention claimed is:

1. A method of treating an Ep-CAM expressing tumor in a subject comprising administering an anti-Ep-CAM antibody and a chemotherapeutic agent that is capable of arresting Ep-CAM antigen expressing cells in S or $G_2/M$ to a subject with an Ep-CAM expressing tumor, wherein the chemotherapeutic agent is selected from the group consisting of camptothecin-11, oxaliplatin, paclitaxel, docetaxel, cyclophosphamide, vinorelbine tartrate, epirubicin, mitoxantrone, raltitrexed, carboplatinum, etoposide and topotecan, and is administered to the subject prior to, or simultaneously with, the anti-Ep-CAM antibody; whereby the Ep-CAM expressing tumor in the subject is treated.

2. The method of claim 1, wherein the anti-Ep-CAM antibody is humanized.

3. A method of treating an Ep-CAM expressing tumor in a subject comprising administering an anti-Ep-CAM antibody and a chemotherapeutic agent that is capable of arresting Ep-CAM antigen expressing cells in S or $G_2/M$ to a subject with an Ep-CAM expressing tumor, wherein the chemotherapeutic agent is docetaxel, and is administered to the subject prior to, or simultaneously with, the anti-Ep-CAM antibody; whereby the Ep-CAM expressing tumor in the subject is treated.

4. The method of claim 3, wherein the anti-Ep-CAM antibody is humanized.

5. A method of treating an Ep-CAM expressing tumor in a subject comprising administering an anti-Ep-CAM antibody and a chemotherapeutic agent that is capable of arresting Ep-CAM antigen expressing cells in S or $G_2/M$ to a subject with an Ep-CAM expressing tumor, wherein the chemotherapeutic agent is paclitaxel, and is administered to the subject prior to, or simultaneously with, the anti-Ep-CAM antibody; whereby the Ep-CAM expressing tumor in the subject is treated.

6. The method of claim 5, wherein the anti-Ep-CAM antibody is humanized.

* * * * *

SEQUENCE LISTING

```
<160> NUMBER OF SEQ ID NOS: 16

<210> SEQ ID NO 1
<211> LENGTH: 740
<212> TYPE: DNA
<213> ORGANISM: Artificial Sequence
<220> FEATURE:
<221> NAME/KEY: CDS
<222> LOCATION: (24)..(740)
<220> FEATURE:
<223> OTHER INFORMATION: Description of Artificial Sequence: Synthetic
```

-continued sequence

<400> SEQUENCE: 1

```
cgtaagcttc acaggacctc acc atg gga tgg agc tgt atc atc ctc ttc ttg        53
                        Met Gly Trp Ser Cys Ile Ile Leu Phe Leu
                         1               5                  10 gta gca aca gct aca ggt gtc cac tcc gat att gtg atg act cag tct         101
Val Ala Thr Ala Thr Gly Val His Ser Asp Ile Val Met Thr Gln Ser
             15                  20                  25 cca ctc tcc ctg ccc gtc acc cct gga gag ccg gcc tcc atc tcc tgt         149
Pro Leu Ser Leu Pro Val Thr Pro Gly Glu Pro Ala Ser Ile Ser Cys
         30                  35                  40 agg tct agt aag aat ctc ctg cat agt aat ggc atc act tat ttg tat         197
Arg Ser Ser Lys Asn Leu Leu His Ser Asn Gly Ile Thr Tyr Leu Tyr
     45                  50                  55 tgg tac ctg cag aag cca ggg cag tct cca cag ctc ctg atc tat cag         245
Trp Tyr Leu Gln Lys Pro Gly Gln Ser Pro Gln Leu Leu Ile Tyr Gln
 60                  65                  70 atg tcc aac ctt gcc tca ggg gtc cct gac agg ttc agt agc agt gga         293
Met Ser Asn Leu Ala Ser Gly Val Pro Asp Arg Phe Ser Ser Ser Gly
 75                  80                  85                  90 tca ggc aca gat ttt aca ctg aaa atc agc aga gtg gag gct gag gat         341
Ser Gly Thr Asp Phe Thr Leu Lys Ile Ser Arg Val Glu Ala Glu Asp
                 95                 100                 105 gtt ggg gtt tat tac tgt gct caa aat cta gag att cct cgg acg ttc         389
Val Gly Val Tyr Tyr Cys Ala Gln Asn Leu Glu Ile Pro Arg Thr Phe
            110                 115                 120 ggc caa ggg acc aag gtg gag atc aaa cgt acg gtg gct gca cca tct         437
Gly Gln Gly Thr Lys Val Glu Ile Lys Arg Thr Val Ala Ala Pro Ser
        125                 130                 135 gtc ttc atc ttc ccg cca tct gat gag cag ttg aaa tct gga act gcc         485
Val Phe Ile Phe Pro Pro Ser Asp Glu Gln Leu Lys Ser Gly Thr Ala
    140                 145                 150 tct gtt gtg tgc ctg ctg aat aac ttc tat ccc aga gag gcc aaa gta         533
Ser Val Val Cys Leu Leu Asn Asn Phe Tyr Pro Arg Glu Ala Lys Val
155                 160                 165                 170 cag tgg aag gtg gat aac gcc ctc caa tcg ggt aac tcc cag gag agt         581
Gln Trp Lys Val Asp Asn Ala Leu Gln Ser Gly Asn Ser Gln Glu Ser
                175                 180                 185 gtc aca gag cag gac agc aag gac agc acc tac agc ctc agc agc acc         629
Val Thr Glu Gln Asp Ser Lys Asp Ser Thr Tyr Ser Leu Ser Ser Thr
            190                 195                 200 ctg acg ctg agc aaa gca gac tac gag aaa cac aaa gtc tac gcc tgc         677
Leu Thr Leu Ser Lys Ala Asp Tyr Glu Lys His Lys Val Tyr Ala Cys
        205                 210                 215 gaa gtc acc cat cag ggc ctg agc tcg ccc gtc aca aag agc ttc aac         725
Glu Val Thr His Gln Gly Leu Ser Ser Pro Val Thr Lys Ser Phe Asn
    220                 225                 230 agg gga gag tgt tag                                                      740
Arg Gly Glu Cys
235
```

<210> SEQ ID NO 2
<211> LENGTH: 238
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 2

Met Gly Trp Ser Cys Ile Ile Leu Phe Leu Val Ala Thr Ala Thr Gly

|   | 1 |   |   |   | 5 |   |   |   |   | 10 |   |   |   |   | 15 |
|---|---|---|---|---|---|---|---|---|---|---|---|---|---|---|---|

Val His Ser Asp Ile Val Met Thr Gln Ser Pro Leu Ser Leu Pro Val
                  20                       25                     30

Thr Pro Gly Glu Pro Ala Ser Ile Ser Cys Arg Ser Ser Lys Asn Leu
         35                       40                      45

Leu His Ser Asn Gly Ile Thr Tyr Leu Tyr Trp Tyr Leu Gln Lys Pro
     50                       55                     60

Gly Gln Ser Pro Gln Leu Leu Ile Tyr Gln Met Ser Asn Leu Ala Ser
65                    70                    75                     80

Gly Val Pro Asp Arg Phe Ser Ser Gly Ser Gly Thr Asp Phe Thr
             85                       90                   95

Leu Lys Ile Ser Arg Val Glu Ala Glu Asp Val Gly Val Tyr Tyr Cys
               100                 105                 110

Ala Gln Asn Leu Glu Ile Pro Arg Thr Phe Gly Gln Gly Thr Lys Val
         115                      120                125

Glu Ile Lys Arg Thr Val Ala Ala Pro Ser Val Phe Ile Phe Pro Pro
     130                     135                 140

Ser Asp Glu Gln Leu Lys Ser Gly Thr Ala Ser Val Val Cys Leu Leu
145                  150                  155               160

Asn Asn Phe Tyr Pro Arg Glu Ala Lys Val Gln Trp Lys Val Asp Asn
               165                 170                 175

Ala Leu Gln Ser Gly Asn Ser Gln Glu Ser Val Thr Glu Gln Asp Ser
         180                      185                190

Lys Asp Ser Thr Tyr Ser Leu Ser Ser Thr Leu Thr Leu Ser Lys Ala
     195                     200                 205

Asp Tyr Glu Lys His Lys Val Tyr Ala Cys Glu Val Thr His Gln Gly
         210                      215                220

Leu Ser Ser Pro Val Thr Lys Ser Phe Asn Arg Gly Glu Cys
225                  230                  235

<210> SEQ ID NO 3
<211> LENGTH: 740
<212> TYPE: DNA
<213> ORGANISM: Artificial Sequence
<220> FEATURE:
<223> OTHER INFORMATION: Description of Artificial Sequence: Synthetic
     sequence

<400> SEQUENCE: 3

| | | | | | |
|---|---|---|---|---|---|
| ctaacactct | cccctgttga | agctctttgt | gacgggcgag | ctcaggccct | gatgggtgac | 60 |
| ttcgcaggcg | tagactttgt | gtttctcgta | gtctgctttg | ctcagcgtca | gggtgctgct | 120 |
| gaggctgtag | gtgctgtcct | tgctgtcctg | ctctgtgaca | ctctcctggg | agttacccga | 180 |
| ttggagggcg | ttatccacct | tccactgtac | tttggcctct | ctgggataga | agttattcag | 240 |
| caggcacaca | acagaggcag | ttccagattt | caactgctca | tcagatggcg | ggaagatgaa | 300 |
| gacagatggt | gcagccaccg | tacgtttgat | ctccaccttg | gtcccttggc | cgaacgtccg | 360 |
| aggaatctct | agattttgag | cacagtaata | aaccccaaca | tcctcagcct | ccactctgct | 420 |
| gattttcagt | gtaaaatctg | tgcctgatcc | actgctactg | aacctgtcag | ggaccccctga | 480 |
| ggcaaggttg | gacatctgat | agatcaggag | ctgtggagac | tgccctggct | tctgcaggta | 540 |
| ccaatacaaa | taagtgatgc | cattactatg | caggagattc | ttactagacc | tacaggagat | 600 |
| ggaggccggc | tctccagggg | tgacgggcag | ggagagtgga | gactgagtca | tcacaatatc | 660 |
| ggagtggaca | cctgtagctg | ttgctaccaa | gaagaggatg | atacagctcc | atcccatggt | 720 |
| gaggtcctgt | gaagcttacg | | | | | 740 |

<210> SEQ ID NO 4
<211> LENGTH: 1418
<212> TYPE: DNA
<213> ORGANISM: Artificial Sequence
<220> FEATURE:
<221> NAME/KEY: CDS
<222> LOCATION: (24)..(1418)
<220> FEATURE:
<223> OTHER INFORMATION: Description of Artificial Sequence: Synthetic
    sequence

<400> SEQUENCE: 4

```
cgtaagcttc acagatcctc acc atg gga tgg agc tgt atc atc ctc ttt ctg      53
                         Met Gly Trp Ser Cys Ile Ile Leu Phe Leu
                          1               5                  10 gtg gca aca gct aca ggt gtc cac tcc cag gta cag cta gtg caa tca        101
Val Ala Thr Ala Thr Gly Val His Ser Gln Val Gln Leu Val Gln Ser
                 15                  20                  25 ggg cct gaa gtg aag aag cct ggg gcc tca gtg aaa gtt tcc tgc aag        149
Gly Pro Glu Val Lys Lys Pro Gly Ala Ser Val Lys Val Ser Cys Lys
         30                  35                  40 gct tct ggc tac acc ttc acc aac tat gga atg aac tgg gta agg cag        197
Ala Ser Gly Tyr Thr Phe Thr Asn Tyr Gly Met Asn Trp Val Arg Gln
     45                  50                  55 gcg cct gga cag ggg ctt gag tgg atg ggg tgg ata aac acc tac act        245
Ala Pro Gly Gln Gly Leu Glu Trp Met Gly Trp Ile Asn Thr Tyr Thr
 60                  65                  70 gga gag cca aca tat ggt gaa gat ttc aag gga cgg ttt gca ttc tct        293
Gly Glu Pro Thr Tyr Gly Glu Asp Phe Lys Gly Arg Phe Ala Phe Ser
 75                  80                  85                  90 cta gac aca tcc gcc agc aca gcc tat atg gag ctc agc tcg ctg aga        341
Leu Asp Thr Ser Ala Ser Thr Ala Tyr Met Glu Leu Ser Ser Leu Arg
                 95                 100                 105 tcc gag gac act gca gtc tat ttc tgt gcg aga ttt ggt aac tac gta        389
Ser Glu Asp Thr Ala Val Tyr Phe Cys Ala Arg Phe Gly Asn Tyr Val
             110                 115                 120 gac tac tgg ggt caa gga tca cta gtc act gtc tcc tca gcc tcc acc        437
Asp Tyr Trp Gly Gln Gly Ser Leu Val Thr Val Ser Ser Ala Ser Thr
         125                 130                 135 aag ggc cca tcg gtc ttc ccc ctg gca ccc tcc tcc aag agc acc tct        485
Lys Gly Pro Ser Val Phe Pro Leu Ala Pro Ser Ser Lys Ser Thr Ser
     140                 145                 150 ggg ggc aca gcg gcc ctg ggc tgc ctg gtc aag gac tac ttc ccc gaa        533
Gly Gly Thr Ala Ala Leu Gly Cys Leu Val Lys Asp Tyr Phe Pro Glu
155                 160                 165                 170 ccg gtg acg gtg tcg tgg aac tca ggc gcc ctg acc agc ggc gtg cac        581
Pro Val Thr Val Ser Trp Asn Ser Gly Ala Leu Thr Ser Gly Val His
                 175                 180                 185 acc ttc ccg gct gtc cta cag tcc tca gga ctc tac tcc ctc agc agc        629
Thr Phe Pro Ala Val Leu Gln Ser Ser Gly Leu Tyr Ser Leu Ser Ser
             190                 195                 200 gtg gtg acc gtg ccc tcc agc agc ttg ggc acc cag acc tac atc tgc        677
Val Val Thr Val Pro Ser Ser Ser Leu Gly Thr Gln Thr Tyr Ile Cys
         205                 210                 215 aac gtg aat cac aag ccc agc aac acc aag gtg gac aag aaa gtt gag        725
Asn Val Asn His Lys Pro Ser Asn Thr Lys Val Asp Lys Lys Val Glu
     220                 225                 230 ccc aaa tct tgt gac aaa act cac aca tgc cca ccg tgc cca gca cct        773
Pro Lys Ser Cys Asp Lys Thr His Thr Cys Pro Pro Cys Pro Ala Pro
235                 240                 245                 250 gaa ctc ctg ggg gga ccg tca gtc ttc ctc ttc ccc cca aaa ccc aag        821
Glu Leu Leu Gly Gly Pro Ser Val Phe Leu Phe Pro Pro Lys Pro Lys
```

```
                                    -continued
Glu Leu Leu Gly Gly Pro Ser Val Phe Leu Phe Pro Pro Lys Pro Lys
                    255                 260                 265 gac acc ctc atg atc tcc cgg acc cct gag gtc aca tgc gtg gtg gtg      869
Asp Thr Leu Met Ile Ser Arg Thr Pro Glu Val Thr Cys Val Val Val
                270                 275                 280 gac gtg agc cac gaa gac cct gag gtc aag ttc aac tgg tac gtg gac      917
Asp Val Ser His Glu Asp Pro Glu Val Lys Phe Asn Trp Tyr Val Asp
            285                 290                 295 ggc gtg gag gtg cat aat gcc aag aca aag ccg cgg gag gag cag tac      965
Gly Val Glu Val His Asn Ala Lys Thr Lys Pro Arg Glu Glu Gln Tyr
        300                 305                 310 aac agc acg tac cgt gtg gtc agc gtc ctc acc gtc ctg cac cag gac     1013
Asn Ser Thr Tyr Arg Val Val Ser Val Leu Thr Val Leu His Gln Asp
315                 320                 325                 330 tgg ctg aat ggc aag gag tac aag tgc aag gtc tcc aac aaa gcc ctc     1061
Trp Leu Asn Gly Lys Glu Tyr Lys Cys Lys Val Ser Asn Lys Ala Leu
                335                 340                 345 cca gcc ccc atc gag aaa acc atc tcc aaa gcc aaa ggg cag ccc cga     1109
Pro Ala Pro Ile Glu Lys Thr Ile Ser Lys Ala Lys Gly Gln Pro Arg
            350                 355                 360 gaa cca cag gtg tac acc ctg ccc cca tcc cgg gat gag ctg acc aag     1157
Glu Pro Gln Val Tyr Thr Leu Pro Pro Ser Arg Asp Glu Leu Thr Lys
        365                 370                 375 aac cag gtc agc ctg acc tgc ctg gtc aaa ggc ttc tat ccc agc gac     1205
Asn Gln Val Ser Leu Thr Cys Leu Val Lys Gly Phe Tyr Pro Ser Asp
380                 385                 390 atc gcc gtg gag tgg gag agc aat ggg cag ccg gag aac aac tac aag     1253
Ile Ala Val Glu Trp Glu Ser Asn Gly Gln Pro Glu Asn Asn Tyr Lys
395                 400                 405                 410 acc acg cct ccc gtg ctg gac tcc gac ggc tcc ttc ttc ctc tac agc     1301
Thr Thr Pro Pro Val Leu Asp Ser Asp Gly Ser Phe Phe Leu Tyr Ser
                415                 420                 425 aag ctc acc gtg gac aag agc agg tgg cag cag ggg aac gtc ttc tca     1349
Lys Leu Thr Val Asp Lys Ser Arg Trp Gln Gln Gly Asn Val Phe Ser
            430                 435                 440 tgc tcc gtg atg cat gag gct ctg cac aac cac tac acg cag aag agc     1397
Cys Ser Val Met His Glu Ala Leu His Asn His Tyr Thr Gln Lys Ser
        445                 450                 455 ctc tcc ctg tct ccg ggt aaa                                         1418
Leu Ser Leu Ser Pro Gly Lys
    460                 465

<210> SEQ ID NO 5
<211> LENGTH: 465
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 5

Met Gly Trp Ser Cys Ile Ile Leu Phe Leu Val Ala Thr Ala Thr Gly
1               5                   10                  15

Val His Ser Gln Val Gln Leu Val Gln Ser Gly Pro Glu Val Lys Lys
            20                  25                  30

Pro Gly Ala Ser Val Lys Val Ser Cys Lys Ala Ser Gly Tyr Thr Phe
        35                  40                  45

Thr Asn Tyr Gly Met Asn Trp Val Arg Gln Ala Pro Gly Gln Gly Leu
    50                  55                  60

Glu Trp Met Gly Trp Ile Asn Thr Tyr Thr Gly Glu Pro Thr Tyr Gly
65                  70                  75                  80
```

```
Glu Asp Phe Lys Gly Arg Phe Ala Phe Ser Leu Asp Thr Ser Ala Ser
                85                  90                  95
Thr Ala Tyr Met Glu Leu Ser Ser Leu Arg Ser Glu Asp Thr Ala Val
            100                 105                 110
Tyr Phe Cys Ala Arg Phe Gly Asn Tyr Val Asp Tyr Trp Gly Gln Gly
        115                 120                 125
Ser Leu Val Thr Val Ser Ser Ala Ser Thr Lys Gly Pro Ser Val Phe
130                 135                 140
Pro Leu Ala Pro Ser Ser Lys Ser Thr Ser Gly Gly Thr Ala Ala Leu
145                 150                 155                 160
Gly Cys Leu Val Lys Asp Tyr Phe Pro Glu Pro Val Thr Val Ser Trp
                165                 170                 175
Asn Ser Gly Ala Leu Thr Ser Gly Val His Thr Phe Pro Ala Val Leu
            180                 185                 190
Gln Ser Ser Gly Leu Tyr Ser Leu Ser Ser Val Val Thr Val Pro Ser
        195                 200                 205
Ser Ser Leu Gly Thr Gln Thr Tyr Ile Cys Asn Val Asn His Lys Pro
210                 215                 220
Ser Asn Thr Lys Val Asp Lys Lys Val Glu Pro Lys Ser Cys Asp Lys
225                 230                 235                 240
Thr His Thr Cys Pro Pro Cys Pro Ala Pro Glu Leu Leu Gly Gly Pro
                245                 250                 255
Ser Val Phe Leu Phe Pro Pro Lys Pro Lys Asp Thr Leu Met Ile Ser
            260                 265                 270
Arg Thr Pro Glu Val Thr Cys Val Val Val Asp Val Ser His Glu Asp
        275                 280                 285
Pro Glu Val Lys Phe Asn Trp Tyr Val Asp Gly Val Glu Val His Asn
290                 295                 300
Ala Lys Thr Lys Pro Arg Glu Glu Gln Tyr Asn Ser Thr Tyr Arg Val
305                 310                 315                 320
Val Ser Val Leu Thr Val Leu His Gln Asp Trp Leu Asn Gly Lys Glu
                325                 330                 335
Tyr Lys Cys Lys Val Ser Asn Lys Ala Leu Pro Ala Pro Ile Glu Lys
            340                 345                 350
Thr Ile Ser Lys Ala Lys Gly Gln Pro Arg Glu Pro Gln Val Tyr Thr
        355                 360                 365
Leu Pro Pro Ser Arg Asp Glu Leu Thr Lys Asn Gln Val Ser Leu Thr
370                 375                 380
Cys Leu Val Lys Gly Phe Tyr Pro Ser Asp Ile Ala Val Glu Trp Glu
385                 390                 395                 400
Ser Asn Gly Gln Pro Glu Asn Asn Tyr Lys Thr Thr Pro Pro Val Leu
                405                 410                 415
Asp Ser Asp Gly Ser Phe Phe Leu Tyr Ser Lys Leu Thr Val Asp Lys
            420                 425                 430
Ser Arg Trp Gln Gln Gly Asn Val Phe Ser Cys Ser Val Met His Glu
        435                 440                 445
Ala Leu His Asn His Tyr Thr Gln Lys Ser Leu Ser Leu Ser Pro Gly
450                 455                 460
Lys
465

<210> SEQ ID NO 6
<211> LENGTH: 1418
<212> TYPE: DNA
```

<213> ORGANISM: Artificial Sequence
<220> FEATURE:
<221> NAME/KEY: CDS
<222> LOCATION: (24)..(1412)
<220> FEATURE:
<223> OTHER INFORMATION: Description of Artificial Sequence: Synthetic sequence

<400> SEQUENCE: 6

```
cgtaagcttc acagatcctc acc atg gga tgg agc tgt atc atc ctc ttt ctg      53
                         Met Gly Trp Ser Cys Ile Ile Leu Phe Leu
                          1               5                  10 gtg gca aca gct aca ggt gtc cac tcc cag gta cag cta gtg caa tca        101
Val Ala Thr Ala Thr Gly Val His Ser Gln Val Gln Leu Val Gln Ser
                 15                  20                  25 ggg cct gaa gtg aag aag cct ggg gcc tca gtg aaa gtt tcc tgc aag        149
Gly Pro Glu Val Lys Lys Pro Gly Ala Ser Val Lys Val Ser Cys Lys
             30                  35                  40 gct tct ggc tac acc ttc acc aac tat gga atg aac tgg gta agg cag        197
Ala Ser Gly Tyr Thr Phe Thr Asn Tyr Gly Met Asn Trp Val Arg Gln
         45                  50                  55 gcg cct gga cag ggg ctt gag tgg atg ggg tgg ata aac acc tac act        245
Ala Pro Gly Gln Gly Leu Glu Trp Met Gly Trp Ile Asn Thr Tyr Thr
     60                  65                  70 gga gag cca aca tat ggt gaa gat ttc aag gga cgg ttt gca ttc tct        293
Gly Glu Pro Thr Tyr Gly Glu Asp Phe Lys Gly Arg Phe Ala Phe Ser
 75                  80                  85                  90 cta gac aca tcc gcc agc aca gcc tat atg gag ctc agc tcg ctg aga        341
Leu Asp Thr Ser Ala Ser Thr Ala Tyr Met Glu Leu Ser Ser Leu Arg
                 95                 100                 105 tcc gag gac act gca gtc tat ttc tgt gcg aga ttt ggt aac tac gta        389
Ser Glu Asp Thr Ala Val Tyr Phe Cys Ala Arg Phe Gly Asn Tyr Val
             110                 115                 120 gac tac tgg ggt caa gga tca cta gtc act gtc tcc tca gct tcc acc        437
Asp Tyr Trp Gly Gln Gly Ser Leu Val Thr Val Ser Ser Ala Ser Thr
         125                 130                 135 aag ggc cca tcc gtc ttc ccc ctg gcg ccc tgc tcc agg agc acc tcc        485
Lys Gly Pro Ser Val Phe Pro Leu Ala Pro Cys Ser Arg Ser Thr Ser
     140                 145                 150 gag agc aca gcc gcc ctg ggc tgc ctg gtc aag gac tac ttc ccc gaa        533
Glu Ser Thr Ala Ala Leu Gly Cys Leu Val Lys Asp Tyr Phe Pro Glu
155                 160                 165                 170 ccg gtg acg gtg tcg tgg aac tca ggc gcc ctg acc agc ggc gtg cac        581
Pro Val Thr Val Ser Trp Asn Ser Gly Ala Leu Thr Ser Gly Val His
                 175                 180                 185 acc ttc ccg gct gtc cta cag tcc tca gga ctc tac tcc ctc agc agc        629
Thr Phe Pro Ala Val Leu Gln Ser Ser Gly Leu Tyr Ser Leu Ser Ser
             190                 195                 200 gtg gtg acc gtg ccc tcc agc agc ttg ggc acg aag acc tac acc tgc        677
Val Val Thr Val Pro Ser Ser Ser Leu Gly Thr Lys Thr Tyr Thr Cys
         205                 210                 215 aac gta gat cac aag ccc agc aac acc aag gtg gac aag aga gtt gag        725
Asn Val Asp His Lys Pro Ser Asn Thr Lys Val Asp Lys Arg Val Glu
     220                 225                 230 tcc aaa tat ggt ccc cca tgc cca ccg tgc cct gca cct gag ttc gcg        773
Ser Lys Tyr Gly Pro Pro Cys Pro Pro Cys Pro Ala Pro Glu Phe Ala
235                 240                 245                 250 ggg gca cca tca gtc ttc ctg ttc ccc cca aaa ccc aag gac act ctc        821
Gly Ala Pro Ser Val Phe Leu Phe Pro Pro Lys Pro Lys Asp Thr Leu
                 255                 260                 265 atg atc tcc cgg acc cct gag gtc acg tgc gtg gtg gtg gac gtg agc        869
Met Ile Ser Arg Thr Pro Glu Val Thr Cys Val Val Val Asp Val Ser
```

|  |  |  |  |  |  |  |  |  |  |  |  |  |  |  |  |
|---|---|---|---|---|---|---|---|---|---|---|---|---|---|---|---|
|  |  |  | 270 |  |  |  | 275 |  |  |  | 280 |  |  |  |  |
| cag | gaa | gac | ccc | gag | gtc | cag | ttc | aac | tgg | tac | gtg | gat | ggc | gtg | gag | 917 |
| Gln | Glu | Asp | Pro | Glu | Val | Gln | Phe | Asn | Trp | Tyr | Val | Asp | Gly | Val | Glu |  |
|  |  | 285 |  |  |  |  | 290 |  |  |  |  | 295 |  |  |  |  |
| gtg | cat | aat | gcc | aag | aca | aag | ccg | cgg | gag | gag | cag | ttc | aac | agc | acg | 965 |
| Val | His | Asn | Ala | Lys | Thr | Lys | Pro | Arg | Glu | Glu | Gln | Phe | Asn | Ser | Thr |  |
|  | 300 |  |  |  |  | 305 |  |  |  |  | 310 |  |  |  |  |  |
| tac | cgt | gtg | gtc | agc | gtc | ctc | acc | gtc | ctg | cac | cag | gac | tgg | ctg | acc | 1013 |
| Tyr | Arg | Val | Val | Ser | Val | Leu | Thr | Val | Leu | His | Gln | Asp | Trp | Leu | Thr |  |
| 315 |  |  |  |  | 320 |  |  |  |  | 325 |  |  |  |  | 330 |  |
| ggc | aag | gcg | tac | aag | tgc | aag | gtc | tcc | aac | aaa | ggc | ctc | ccg | tcc | tcc | 1061 |
| Gly | Lys | Ala | Tyr | Lys | Cys | Lys | Val | Ser | Asn | Lys | Gly | Leu | Pro | Ser | Ser |  |
|  |  |  |  | 335 |  |  |  |  | 340 |  |  |  |  | 345 |  |  |
| atc | gag | aaa | acc | atc | tcc | aaa | gcc | aaa | ggg | cag | ccc | cga | gag | cca | cag | 1109 |
| Ile | Glu | Lys | Thr | Ile | Ser | Lys | Ala | Lys | Gly | Gln | Pro | Arg | Glu | Pro | Gln |  |
|  |  |  | 350 |  |  |  |  | 355 |  |  |  |  | 360 |  |  |  |
| gtg | tac | acc | ctg | ccc | cca | tcc | cag | gag | gag | atg | acc | aag | aac | cag | gtc | 1157 |
| Val | Tyr | Thr | Leu | Pro | Pro | Ser | Gln | Glu | Glu | Met | Thr | Lys | Asn | Gln | Val |  |
|  |  | 365 |  |  |  |  | 370 |  |  |  |  | 375 |  |  |  |  |
| agc | ctg | acc | tgc | ctg | gtc | aaa | ggc | ttc | tac | ccc | agc | gac | atc | gcc | gtg | 1205 |
| Ser | Leu | Thr | Cys | Leu | Val | Lys | Gly | Phe | Tyr | Pro | Ser | Asp | Ile | Ala | Val |  |
|  | 380 |  |  |  |  | 385 |  |  |  |  | 390 |  |  |  |  |  |
| gag | tgg | gag | agc | aat | ggg | cag | ccg | gag | aac | aac | tac | aag | acc | acg | cct | 1253 |
| Glu | Trp | Glu | Ser | Asn | Gly | Gln | Pro | Glu | Asn | Asn | Tyr | Lys | Thr | Thr | Pro |  |
| 395 |  |  |  |  | 400 |  |  |  |  | 405 |  |  |  |  | 410 |  |
| ccc | gtg | ctg | gac | tcc | gac | ggc | tcc | ttc | ttc | ctc | tac | agc | agg | cta | acc | 1301 |
| Pro | Val | Leu | Asp | Ser | Asp | Gly | Ser | Phe | Phe | Leu | Tyr | Ser | Arg | Leu | Thr |  |
|  |  |  |  | 415 |  |  |  |  | 420 |  |  |  |  | 425 |  |  |
| gtg | gac | aag | agc | agg | tgg | cag | gag | ggg | aat | gtc | ttc | tca | tgc | tcc | gtg | 1349 |
| Val | Asp | Lys | Ser | Arg | Trp | Gln | Glu | Gly | Asn | Val | Phe | Ser | Cys | Ser | Val |  |
|  |  |  | 430 |  |  |  |  | 435 |  |  |  |  | 440 |  |  |  |
| atg | cat | gag | gct | ctg | cac | aac | cac | tac | aca | cag | aag | agc | ctc | tgc | ctg | 1397 |
| Met | His | Glu | Ala | Leu | His | Asn | His | Tyr | Thr | Gln | Lys | Ser | Leu | Cys | Leu |  |
|  |  | 445 |  |  |  |  | 450 |  |  |  |  | 455 |  |  |  |  |
| tct | ctg | ggt | aaa | tga | gaattc |  |  |  |  |  |  |  |  |  |  | 1418 |
| Ser | Leu | Gly | Lys |  |  |  |  |  |  |  |  |  |  |  |  |  |
|  |  | 460 |  |  |  |  |  |  |  |  |  |  |  |  |  |  |

<210> SEQ ID NO 7
<211> LENGTH: 462
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 7

Met Gly Trp Ser Cys Ile Ile Leu Phe Leu Val Ala Thr Ala Thr Gly
 1               5                  10                  15

Val His Ser Gln Val Gln Leu Val Gln Ser Gly Pro Glu Val Lys Lys
             20                  25                  30

Pro Gly Ala Ser Val Lys Val Ser Cys Lys Ala Ser Gly Tyr Thr Phe
         35                  40                  45

Thr Asn Tyr Gly Met Asn Trp Val Arg Gln Ala Pro Gly Gln Gly Leu
     50                  55                  60

Glu Trp Met Gly Trp Ile Asn Thr Tyr Thr Gly Glu Pro Thr Tyr Gly
 65                  70                  75                  80

Glu Asp Phe Lys Gly Arg Phe Ala Phe Ser Leu Asp Thr Ser Ala Ser
                 85                  90                  95

Thr Ala Tyr Met Glu Leu Ser Ser Leu Arg Ser Glu Asp Thr Ala Val

```
            100                 105                 110
Tyr Phe Cys Ala Arg Phe Gly Asn Tyr Val Asp Tyr Trp Gly Gln Gly
        115                 120                 125

Ser Leu Val Thr Val Ser Ser Ala Ser Thr Lys Gly Pro Ser Val Phe
130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Lys Thr Tyr Thr Cys Asn Val Asp His Lys Pro
    210                 215                 220

Ser Asn Thr Lys Val Asp Lys Arg Val Glu Ser Lys Tyr Gly Pro Pro
225                 230                 235                 240

Cys Pro Pro Cys Pro Ala Pro Glu Phe Ala Gly Ala Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser Gln Glu Asp Pro Glu Val
        275                 280                 285

Gln Phe Asn Trp Tyr Val Asp Gly Val Glu Val His Asn Ala Lys Thr
    290                 295                 300

Lys Pro Arg Glu Glu Gln Phe Asn Ser Thr Tyr Arg Val Val Ser Val
305                 310                 315                 320

Leu Thr Val Leu His Gln Asp Trp Leu Thr Gly Lys Ala Tyr Lys Cys
                325                 330                 335

Lys Val Ser Asn Lys Gly Leu Pro Ser Ser Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Gln Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Arg Leu Thr Val Asp Lys Ser Arg Trp
            420                 425                 430

Gln Glu Gly Asn Val Phe Ser Cys Ser Val Met His Glu Ala Leu His
        435                 440                 445

Asn His Tyr Thr Gln Lys Ser Leu Cys Leu Ser Leu Gly Lys
    450                 455                 460

<210> SEQ ID NO 8
<211> LENGTH: 1392
<212> TYPE: DNA
<213> ORGANISM: Artificial Sequence
<220> FEATURE:
<221> NAME/KEY: CDS
<222> LOCATION: (58)..(1386)
<220> FEATURE:
<223> OTHER INFORMATION: Description of Artificial Sequence: Synthetic
      sequence
```

<400> SEQUENCE: 8

```
atggattggc tgtggaactt gctattcctg atggcagctg cccaaagtat ccaagca        57 cag atc cag ttg gtg cag tct gga cct gaa ctg aag aag cct gga gag      105
Gln Ile Gln Leu Val Gln Ser Gly Pro Glu Leu Lys Lys Pro Gly Glu
  1               5                  10                  15 aca gtc aag atc tcc tgc aag gct tct gga tat acc ttc aca aac tat      153
Thr Val Lys Ile Ser Cys Lys Ala Ser Gly Tyr Thr Phe Thr Asn Tyr
             20                  25                  30 gga atg aac tgg gtg agg cag gct tca gga gag ggt tta aag tgg atg      201
Gly Met Asn Trp Val Arg Gln Ala Ser Gly Glu Gly Leu Lys Trp Met
         35                  40                  45 ggc tgg ata aac acc tac act gga gag cca aca tat ggt gaa gat ttc      249
Gly Trp Ile Asn Thr Tyr Thr Gly Glu Pro Thr Tyr Gly Glu Asp Phe
     50                  55                  60 aag gga cgg ttt gcc ttc tct ttg gaa acc tct gcc agc act gcc tat      297
Lys Gly Arg Phe Ala Phe Ser Leu Glu Thr Ser Ala Ser Thr Ala Tyr
 65                  70                  75                  80 ttg cag atc aac aac ctc aaa aat gaa gac acg gct aca tat ttc tgt      345
Leu Gln Ile Asn Asn Leu Lys Asn Glu Asp Thr Ala Thr Tyr Phe Cys
                 85                  90                  95 gca aga ttt ggt aac tac gta gac tac tgg ggc caa ggc acc act ctc      393
Ala Arg Phe Gly Asn Tyr Val Asp Tyr Trp Gly Gln Gly Thr Thr Leu
            100                 105                 110 aca gtc tcc tca gcc tcc acc aag ggc cca tcg gtc ttc ccc ctg gcg      441
Thr Val Ser Ser Ala Ser Thr Lys Gly Pro Ser Val Phe Pro Leu Ala
        115                 120                 125 ccc tgc tcc agg agc acc tcc gag agc aca gcg gcc ctg ggc tgc ctg      489
Pro Cys Ser Arg Ser Thr Ser Glu Ser Thr Ala Ala Leu Gly Cys Leu
    130                 135                 140 gtc aag gac tac ttc ccc gaa ccg gtg acg gtg tcg tgg aac tca ggc      537
Val Lys Asp Tyr Phe Pro Glu Pro Val Thr Val Ser Trp Asn Ser Gly
145                 150                 155                 160 gct ctg acc agc ggc gtg cac acc ttc cca gct gtc cta cag tcc tca      585
Ala Leu Thr Ser Gly Val His Thr Phe Pro Ala Val Leu Gln Ser Ser
                165                 170                 175 gga ctc tac tcc ctc agc agc gtg gtg acc gtg ccc tcc agc aac ttc      633
Gly Leu Tyr Ser Leu Ser Ser Val Val Thr Val Pro Ser Ser Asn Phe
            180                 185                 190 ggc acc cag acc tac acc tgc aac gta gat cac aag ccc agc aac acc      681
Gly Thr Gln Thr Tyr Thr Cys Asn Val Asp His Lys Pro Ser Asn Thr
        195                 200                 205 aag gtg gac aag aca gtt gag cgc aaa tgt tgt gtc gag tgc cca ccg      729
Lys Val Asp Lys Thr Val Glu Arg Lys Cys Cys Val Glu Cys Pro Pro
    210                 215                 220 tgc cca gca cca cct gtg gca gga ccg tca gtc ttc ctc ttc ccc cca      777
Cys Pro Ala Pro Pro Val Ala Gly Pro Ser Val Phe Leu Phe Pro Pro
225                 230                 235                 240 aaa ccc aag gac acc ctc atg atc tcc cgg acc cct gag gtc acg tgc      825
Lys Pro Lys Asp Thr Leu Met Ile Ser Arg Thr Pro Glu Val Thr Cys
                245                 250                 255 gtg gtg gtg gac gtg agc cac gaa gac ccc gag gtc cag ttc aac tgg      873
Val Val Val Asp Val Ser His Glu Asp Pro Glu Val Gln Phe Asn Trp
            260                 265                 270 tac gtg gac ggc gtg gag gtg cat aat gcc aag aca aag cca cgg gag      921
Tyr Val Asp Gly Val Glu Val His Asn Ala Lys Thr Lys Pro Arg Glu
        275                 280                 285 gag cag ttc aac agc acg ttc cgt gtg gtc agc gtc ctc acc gtt gtg      969
Glu Gln Phe Asn Ser Thr Phe Arg Val Val Ser Val Leu Thr Val Val
    290                 295                 300
```

```
cac cag gac tgg ctg aac ggc aag gag tac aag tgc aag gtc tcc aac    1017
His Gln Asp Trp Leu Asn Gly Lys Glu Tyr Lys Cys Lys Val Ser Asn
305                 310                 315                 320 aaa ggc ctc cca gcc ccc atc gag aaa acc atc tcc aaa acc aaa ggg    1065
Lys Gly Leu Pro Ala Pro Ile Glu Lys Thr Ile Ser Lys Thr Lys Gly
                325                 330                 335 cag ccc cga gaa cca cag gtg tac acc ctg ccc cca tcc cgg gag gag    1113
Gln Pro Arg Glu Pro Gln Val Tyr Thr Leu Pro Pro Ser Arg Glu Glu
            340                 345                 350 atg acc aag aac cag gtc agc ctg acc tgc ctg gtc aaa ggc ttc tac    1161
Met Thr Lys Asn Gln Val Ser Leu Thr Cys Leu Val Lys Gly Phe Tyr
        355                 360                 365 ccc agc gac atc gcc gtg gag tgg gag agc aat ggg cag ccg gag aac    1209
Pro Ser Asp Ile Ala Val Glu Trp Glu Ser Asn Gly Gln Pro Glu Asn
370                 375                 380 aac tac aag acc aca cct ccc atg ctg gac tcc gac ggc tcc ttc ttc    1257
Asn Tyr Lys Thr Thr Pro Pro Met Leu Asp Ser Asp Gly Ser Phe Phe
385                 390                 395                 400 ctc tac agc aag ctc acc gtg gac aag agc agg tgg cag cag ggg aac    1305
Leu Tyr Ser Lys Leu Thr Val Asp Lys Ser Arg Trp Gln Gln Gly Asn
                405                 410                 415 gtc ttc tca tgc tcc gtg atg cat gag gct ctg cac aac cac tac aca    1353
Val Phe Ser Cys Ser Val Met His Glu Ala Leu His Asn His Tyr Thr
            420                 425                 430 cag aag agc ctc tgc ctg tct ctg ggt aaa tga gaattc                 1392
Gln Lys Ser Leu Cys Leu Ser Leu Gly Lys
        435                 440

<210> SEQ ID NO 9
<211> LENGTH: 442
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 9

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Arg Gln Ala Ser Gly Glu Gly Leu Lys Trp Met
        35                  40                  45

Gly Trp Ile Asn Thr Tyr Thr Gly Glu Pro Thr Tyr Gly Glu Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Phe Gly Asn Tyr Val Asp Tyr Trp Gly Gln Gly Thr Thr Leu
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175
```

```
Gly Leu Tyr Ser Leu Ser Ser Val Val Thr Val Pro Ser Ser Asn Phe
            180                 185                 190

Gly Thr Gln Thr Tyr Thr Cys Asn Val Asp His Lys Pro Ser Asn Thr
        195                 200                 205

Lys Val Asp Lys Thr Val Glu Arg Lys Cys Cys Val Glu Cys Pro Pro
    210                 215                 220

Cys Pro Ala Pro Pro Val Ala Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Phe Arg Val Val Ser Val Leu Thr Val Val
    290                 295                 300

His Gln Asp Trp Leu Asn Gly Lys Glu Tyr Lys Cys Lys Val Ser Asn
305                 310                 315                 320

Lys Gly Leu Pro Ala Pro Ile Glu Lys Thr Ile Ser Lys Thr Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Met Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Cys Leu Ser Leu Gly Lys
        435                 440

<210> SEQ ID NO 10
<211> LENGTH: 1392
<212> TYPE: DNA
<213> ORGANISM: Artificial Sequence
<220> FEATURE:
<223> OTHER INFORMATION: Description of Artificial Sequence: Synthetic
      sequence

<400> SEQUENCE: 10
gaattctcat ttacccagag acaggcagag gctcttctgt gtgtagtggt tgtgcagagc      60
ctcatgcatc acggagcatg agaagacgtt ccccctgctgc cacctgctct tgtccacggt    120
gagcttgctg tagaggaaga aggagccgtc ggagtccagc atgggaggtg tggtcttgta    180
gttgttctcc ggctgccat tgctctccca ctccacggcg atgtcgctgg ggtagaagcc     240
tttgaccagg caggtcaggc tgacctggtt cttggtcatc tcctcccggg atgggggcag    300
ggtgtacacc tgtggttctc ggggctgccc tttggttttg agatggtttt tctcgatggg    360
ggctgggagg cctttgttgg agaccttgca cttgtactcc ttgccgttca gccagtcctg    420
gtgcacaacg gtgaggacgc tgaccacacg gaacgtgctg ttgaactgct cctcccgtgg    480
ctttgtcttg gcattatgca cctccacgcc gtccacgtac agttgaact ggacctcggg     540
```

```
gtcttcgtgg ctcacgtcca ccaccacgca cgtgacctca ggggtccggg agatcatgag    600
ggtgtccttg ggttttgggg ggaagaggaa gactgacggt cctgccacag gtggtgctgg    660
gcacggtggg cactcgacac aacatttgcg ctcaactgtc ttgtccacct tggtgttgct    720
gggcttgtga tctacgttgc aggtgtaggt ctgggtgccg aagttgctgg agggcacggt    780
caccacgctg ctgagggagt agagtcctga ggactgtagg acagctggga aggtgtgcac    840
gccgctggtc agagcgcctg agttccacga caccgtcacc ggttcgggga agtagtcctt    900
gaccaggcag cccagggccg ctgtgctctc ggaggtgctc ctggagcagg gcgccagggg    960
gaagaccgat gggcccttgg tggaggctga ggagactgtg agagtggtgc cttggcccca   1020
gtagtctacg tagttaccaa atcttgcaca gaaatatgta gccgtgtctt cattttttgag   1080 gttgttgatc tgcaaatagg cagtgctggc agaggtttcc aaagagaagg caaaccgtcc   1140
cttgaaatct tcaccatatg ttggctctcc agtgtaggtg tttatccagc ccatccactt   1200
taaaccctct cctgaagcct gcctcaccca gttcattcca tagtttgtga aggtatatcc   1260
agaagccttg caggagatct tgactgtctc tccaggcttc ttcagttcag gtccagactg   1320
caccaactgg atctgtgctt ggatactttg ggcagctgcc atcaggaata gcaagttcca   1380
cagccaatcc at                                                        1392
```

<210> SEQ ID NO 11
<211> LENGTH: 238
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 11

```
Met Gly Trp Ser Cys Ile Ile Leu Phe Leu Val Ala Thr Ala Thr Gly
  1               5                  10                  15

Val His Ser Asp Ile Val Met Thr Gln Ser Pro Leu Ser Leu Pro Val
             20                  25                  30

Thr Pro Gly Glu Pro Ala Ser Ile Ser Cys Arg Ser Ser Lys Asn Leu
         35                  40                  45

Leu His Ser Asn Gly Ile Thr Tyr Leu Tyr Trp Tyr Leu Gln Lys Pro
     50                  55                  60

Gly Gln Ser Pro Gln Leu Leu Ile Tyr Gln Met Ser Asn Leu Ala Ser
 65                  70                  75                  80

Gly Val Pro Asp Arg Phe Ser Ser Gly Ser Gly Thr Asp Phe Thr
                 85                  90                  95

Leu Lys Ile Ser Arg Val Glu Ala Glu Asp Val Gly Val Tyr Tyr Cys
                100                 105                 110

Ala Gln Asn Leu Glu Ile Pro Arg Thr Phe Gly Gln Gly Thr Lys Val
            115                 120                 125

Glu Ile Lys Arg Thr Val Ala Ala Pro Ser Val Phe Ile Phe Pro Pro
        130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205
```

Asp Tyr Glu Lys His Lys Val Tyr Ala Cys Glu Val Thr His Gln Gly
            210                 215                 220

Leu Ser Ser Pro Val Thr Lys Ser Phe Asn Arg Gly Glu Cys
225                 230                 235

<210> SEQ ID NO 12
<211> LENGTH: 465
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 12

Met Gly Trp Ser Cys Ile Ile Leu Phe Leu Val Ala Thr Ala Thr Gly
 1               5                  10                  15

Val His Ser Gln Val Gln Leu Val Gln Ser Gly Pro Glu Val Lys Lys
                20                  25                  30

Pro Gly Ala Ser Val Lys Val Ser Cys Lys Ala Ser Gly Tyr Thr Phe
            35                  40                  45

Thr Asn Tyr Gly Met Asn Trp Val Arg Gln Ala Pro Gly Gln Gly Leu
         50                 55                  60

Glu Trp Met Gly Trp Ile Asn Thr Tyr Thr Gly Glu Pro Thr Tyr Gly
 65                 70                  75                  80

Glu Asp Phe Lys Gly Arg Phe Ala Phe Ser Leu Asp Thr Ser Ala Ser
                85                  90                  95

Thr Ala Tyr Met Glu Leu Ser Ser Leu Arg Ser Glu Asp Thr Ala Val
            100                 105                 110

Tyr Phe Cys Ala Arg Phe Gly Asn Tyr Val Asp Tyr Trp Gly Gln Gly
        115                 120                 125

Ser Leu Val Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

```
Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Asp Glu Leu Thr Lys Asn Gln Val Ser Leu Thr
370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465

<210> SEQ ID NO 13
<211> LENGTH: 238
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 13

Met Gly Trp Ser Cys Ile Ile Leu Phe Leu Val Ala Thr Ala Thr Gly
1               5                   10                  15

Val His Ser Asp Ile Val Met Thr Gln Ser Pro Leu Ser Leu Pro Val
            20                  25                  30

Thr Pro Gly Glu Pro Ala Ser Ile Ser Cys Arg Ser Ser Lys Asn Leu
        35                  40                  45

Leu His Ser Asn Gly Ile Thr Tyr Leu Tyr Trp Tyr Leu Gln Lys Pro
    50                  55                  60

Gly Gln Ser Pro Gln Leu Leu Ile Tyr Gln Met Ser Asn Leu Ala Ser
65                  70                  75                  80

Gly Val Pro Asp Arg Phe Ser Ser Ser Gly Ser Gly Thr Asp Phe Thr
                85                  90                  95

Leu Lys Ile Ser Arg Val Glu Ala Glu Asp Val Gly Val Tyr Tyr Cys
            100                 105                 110

Ala Gln Asn Leu Glu Ile Pro Arg Thr Phe Gly Gln Gly Thr Lys Val
        115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220
```

Leu Ser Ser Pro Val Thr Lys Ser Phe Asn Arg Gly Glu Cys
225                 230                 235

<210> SEQ ID NO 14
<211> LENGTH: 462
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 14

Met Gly Trp Ser Cys Ile Ile Leu Phe Leu Val Ala Thr Ala Thr Gly
1               5                   10                  15

Val His Ser Gln Val Gln Leu Val Gln Ser Gly Pro Glu Val Lys Lys
            20                  25                  30

Pro Gly Ala Ser Val Lys Val Ser Cys Lys Ala Ser Gly Tyr Thr Phe
        35                  40                  45

Thr Asn Tyr Gly Met Asn Trp Val Arg Gln Ala Pro Gly Gln Gly Leu
    50                  55                  60

Glu Trp Met Gly Trp Ile Asn Thr Tyr Thr Gly Glu Pro Thr Tyr Gly
65                  70                  75                  80

Glu Asp Phe Lys Gly Arg Phe Ala Phe Ser Leu Asp Thr Ser Ala Ser
                85                  90                  95

Thr Ala Tyr Met Glu Leu Ser Ser Leu Arg Ser Glu Asp Thr Ala Val
            100                 105                 110

Tyr Phe Cys Ala Arg Phe Gly Asn Tyr Val Asp Tyr Trp Gly Gln Gly
        115                 120                 125

Ser Leu Val Thr Val Ser Ser Ala Ser Thr Lys Gly Pro Ser Val Phe
    130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Lys Thr Tyr Thr Cys Asn Val Asp His Lys Pro
    210                 215                 220

Ser Asn Thr Lys Val Asp Lys Arg Val Glu Ser Lys Tyr Gly Pro Pro
225                 230                 235                 240

Cys Pro Pro Cys Pro Ala Pro Glu Phe Ala Gly Ala Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser Gln Glu Asp Pro Glu Val
        275                 280                 285

Gln Phe Asn Trp Tyr Val Asp Gly Val Glu Val His Asn Ala Lys Thr
    290                 295                 300

Lys Pro Arg Glu Glu Gln Phe Asn Ser Thr Tyr Arg Val Val Ser Val
305                 310                 315                 320

Leu Thr Val Leu His Gln Asp Trp Leu Asn Gly Lys Ala Tyr Lys Cys
                325                 330                 335

Lys Val Ser Asn Lys Gly Leu Pro Ser Ser Ile Glu Lys Thr Ile Ser
            340                 345                 350

```
Lys Ala Lys Gly Gln Pro Arg Glu Pro Gln Val Tyr Thr Leu Pro Pro
            355                 360                 365

Ser Gln Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Arg Leu Thr Val Asp Lys Ser Arg Trp
            420                 425                 430

Gln Glu Gly Asn Val Phe Ser Cys Ser Val Met His Glu Ala Leu His
        435                 440                 445

Asn His Tyr Thr Gln Lys Ser Leu Cys Leu Ser Leu Gly Lys
    450                 455                 460

<210> SEQ ID NO 15
<211> LENGTH: 238
<212> TYPE: PRT
<213> ORGANISM: Artificial Sequence
<220> FEATURE:
<223> OTHER INFORMATION: Description of Artificial Sequence: Synthetic
      sequence

<400> SEQUENCE: 15

Met Gly Trp Ser Cys Ile Ile Leu Phe Leu Val Ala Thr Ala Thr Gly
 1               5                  10                  15

Val His Ser Asp Ile Val Met Thr Gln Ser Pro Leu Ser Leu Pro Val
            20                  25                  30

Thr Pro Gly Glu Pro Ala Ser Ile Ser Cys Arg Ser Ser Lys Asn Leu
        35                  40                  45

Leu His Ser Asn Gly Ile Thr Tyr Leu Tyr Trp Tyr Leu Gln Lys Pro
    50                  55                  60

Gly Gln Ser Pro Gln Leu Leu Ile Tyr Gln Met Ser Asn Leu Ala Ser
65                  70                  75                  80

Gly Val Pro Asp Arg Phe Ser Ser Ser Gly Ser Gly Thr Asp Phe Thr
                85                  90                  95

Leu Lys Ile Ser Arg Val Glu Ala Glu Asp Val Gly Val Tyr Tyr Cys
            100                 105                 110

Ala Gln Asn Leu Glu Ile Pro Arg Thr Phe Gly Gln Gly Thr Lys Val
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 16
<211> LENGTH: 461
```

<212> TYPE: PRT
<213> ORGANISM: Artificial Sequence
<220> FEATURE:
<223> OTHER INFORMATION: Description of Artificial Sequence: Synthetic sequence

<400> SEQUENCE: 16

Met Gly Trp Ser Cys Ile Ile Leu Phe Leu Val Ala Thr Ala Thr Gly
1               5                   10                  15

Val His Ser Gln Val Gln Leu Val Gln Ser Gly Pro Glu Val Lys Lys
            20                  25                  30

Pro Gly Ala Ser Val Lys Val Ser Cys Lys Ala Ser Gly Tyr Thr Phe
        35                  40                  45

Thr Asn Tyr Gly Met Asn Trp Val Arg Gln Ala Pro Gly Gln Gly Leu
    50                  55                  60

Glu Trp Met Gly Trp Ile Asn Thr Tyr Thr Gly Glu Pro Thr Tyr Gly
65                  70                  75                  80

Glu Asp Phe Lys Gly Arg Phe Ala Phe Ser Leu Asp Thr Ser Ala Ser
                85                  90                  95

Thr Ala Tyr Met Glu Leu Ser Ser Leu Arg Ser Glu Asp Thr Ala Val
            100                 105                 110

Tyr Phe Cys Ala Arg Phe Gly Asn Tyr Val Asp Tyr Trp Gly Gln Gly
        115                 120                 125

Ser Leu Val Thr Val Ser Ser Ala Ser Thr Lys Gly Pro Ser Val Phe
    130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Asn Phe Gly Thr Gln Thr Tyr Thr Cys Asn Val Asp His Lys Pro
    210                 215                 220

Ser Asn Thr Lys Val Asp Lys Thr Val Glu Arg Lys Cys Cys Val Glu
225                 230                 235                 240

Cys Pro Pro Cys Pro Ala Pro Pro Val Ala Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Gln
        275                 280                 285

Phe Asn Trp Tyr Val Asp Gly Val Glu Val His Asn Ala Lys Thr Lys
    290                 295                 300

Pro Arg Glu Glu Gln Phe Asn Ser Thr Phe Arg Val Val Ser Val Leu
305                 310                 315                 320

Thr Val Val His Gln Asp Trp Leu Asn Gly Lys Glu Tyr Lys Cys Lys
                325                 330                 335

Val Ser Asn Lys Gly Leu Pro Ala Pro Ile Glu Lys Thr Ile Ser Lys
            340                 345                 350

Thr Lys Gly Gln Pro Arg Glu Pro Gln Val Tyr Thr Leu Pro Pro Ser
        355                 360                 365

Arg Glu Glu Met Thr Lys Asn Gln Val Ser Leu Thr Cys Leu Val Lys
    370                 375                 380

```
Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Met Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Cys Leu Ser Leu Gly Lys
    450                 455                 460
```